US009492523B2

(12) United States Patent
Picking et al.

(10) Patent No.: US 9,492,523 B2
(45) Date of Patent: Nov. 15, 2016

(54) **BROADLY PROTECTIVE *SHIGELLA* VACCINE BASED ON TYPE III SECRETION APPARATUS PROTEINS**

(71) Applicant: The Board of Regents for Oklahoma State University, Stillwater, OK (US)

(72) Inventors: Wendy L. Picking, Stillwater, OK (US); William D. Picking, Stillwater, OK (US)

(73) Assignee: THE BOARD OF REGENTS FOR OKLAHOMA STATE UNIVERSITY, Stillwater, OK (US)

( * ) Notice: Subject to any disclaimer, the term of this patent is extended or adjusted under 35 U.S.C. 154(b) by 174 days.

(21) Appl. No.: 13/709,689

(22) Filed: Dec. 10, 2012

(65) Prior Publication Data

US 2013/0149329 A1    Jun. 13, 2013

Related U.S. Application Data

(60) Provisional application No. 61/568,918, filed on Dec. 9, 2011.

(51) Int. Cl.
| *A61K 39/395* | (2006.01) |
| *A61K 39/112* | (2006.01) |
| *C07K 14/25* | (2006.01) |
| *A61K 39/00* | (2006.01) |

(52) U.S. Cl.
CPC .......... *A61K 39/0283* (2013.01); *C07K 14/25* (2013.01); *A61K 2039/54* (2013.01); *A61K 2039/543* (2013.01); *A61K 2039/55544* (2013.01); *A61K 2039/58* (2013.01)

(58) Field of Classification Search
None
See application file for complete search history.

(56) References Cited

U.S. PATENT DOCUMENTS

| 7,094,410 B2 | 8/2006 | Reisfeld et al. |
| 7,927,870 B2 | 4/2011 | Volkin et al. |
| 8,039,007 B2 | 10/2011 | Rappuoli et al. |
| 2007/0202124 A1* | 8/2007 | Picking et al. ............ 424/190.1 |

OTHER PUBLICATIONS

Picking et al.( Protein Expression and purification vol. 8, pp. 401-408, 1996).*
Birket et al. Biochemistry vo.46, pp. 8128-8137, 2007.*
Samer El-Kamary et al., "Adjuvanted Intranasal Norwalk Virus-Like Particle Vaccine Elicits Antibodies . . . ", Oct. 2010, pp. 1649-1658, vol. 202, No. 11, Publisher: Journal of Infectious Diseases, Published in: US.
Way, et al., "An Essential Role for Gamma Interferon in Innate Resistance to Shigella Flexneri Infection", Apr. 1998, pp. 1342-1348, vol. 66, No. 4, Publisher: Infection and Immunity, Published in: US.
Who, "Diarrhoeal Diseases (Updated Feb. 2009)", Feb. 2009.

(Continued)

*Primary Examiner* — Gary Nickol
*Assistant Examiner* — Khatol Shahnan Shah
(74) *Attorney, Agent, or Firm* — Fellers, Snider, Blankenship, Bailey & Tippens, P.C.; Terry L. Watt

(57) ABSTRACT

Broad-based, cross-protective, O-serotype independent vaccines against *Shigella* and related pathogenic organisms are provided. The vaccines comprise one or more of the type III secretion (TTS) apparatus needle proteins IpaD and IpaB, and/or the IpaB cognate chaperone protein IpgC. Chimeric proteins of IpaD and IpaB, and/or IpgC are also encompassed.

6 Claims, 35 Drawing Sheets

(56) References Cited

OTHER PUBLICATIONS

Figure 1:
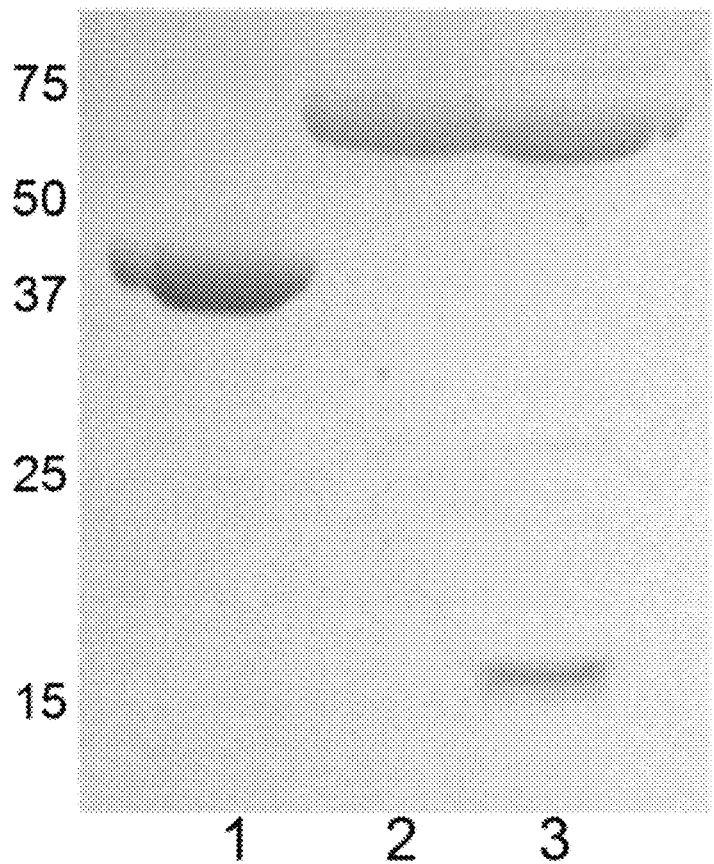

World Health Organization, "Shigellosis in Sudan", 2004, Publisher: World Health Organization.

Wong, et al., "Antimicrobial Resistance Trends of Shigella Serotypes in New York City, 2006-2009", 2010, pp. 155-161, vol. 16, No. 2, Publisher: Microbial Drug Resistance, Published in: US.

Ye, et al., "Emergence ofa New Multidrug-Resistant Serotype X Variant in an Epidemic Clone of Shigella Flexneri", Feb. 12, 2009, Published in: US.

Katz, David, et al., "Two Studies Evaluating the Safety and Immunogenicity of a Live, Attenuated Shigella Flexneri 2a Vaccine (SC602) and EXCR", Feb. 2004, pp. 923-930, Publisher: Inspection and Immunity, Published in: US.

Tribble, et al., "Safety and Immunogenicity of a Shigella Flexneri 2a Invaplex 50 Intransasal Vaccine in Adult Volunteers", Jun. 25, 2010, Publisher: Vaccine 28, Published in: US.

Barnoy, et al., "Characterization of WRSs2 and WRSs3, New Second-Generation virG(icsA)-Based Shigella Sonnei Vaccine . . . ", Nov. 20, 2009, pp. 1642-1654, vol. 28, Publisher: Vaccine, Published in: US.

Barta, et al., "Identification of the Bile Salt Binding Site on IpaD From Shigella Flexneri and the Influence of . . . ", 2011, pp. 935-945, Publisher: Wiley Periodicals, Inc., Published in: US.

Birket, et al., "Preparation and Characterization of Translocator/chaperone Complexes and Their Component Proteins From Shigella Flexneri", Jun. 16, 2007, pp. 8128-8137, vol. 46, Publisher: Biochemistry 2007, Published in: US.

Blocker, et al., "The Tripartite Type III Secretion of Shigella Flexneri Inserts IpaB and IpaC Into Host Membranes", Nov. 1, 1999, pp. 683-693, vol. 147, No. 3, Publisher: The Journal of Cell Biology, Published in: US.

Cohen, D. et al., "Safety and Immunogenicity of Investigational Shigella Conjugate Vaccines in Israeli Volunteers", Oct. 1996, pp. 4074-4077, Publisher: Infection and Immunity, Published in: US.

Cam, et al., "Immune Response Against Lipopolysaccharide and Invasion Plasmid-Coded Antigens . . . ", 1993, pp. 454-457, vol. 31, No. 2, Publisher: Journal of Clinical Microbiology, Published in: US.

Cohen, Dani, et al., "Prospective Study of the Association Between Serum Antibodies to Lipopolysaccharide O Antigen and the Attach Rate of SHI", Feb. 1991, pp. 386-389, vol. 29, No. 2, Publisher: Journal of Clinical Microbiology, Published in: US.

C0hen, Dani, et al., "Serum Antibodies to Lipopolysaccharide and Natural Immunity to Shigellosis in an Israeli Military Population", May 1988, pp. 1068-1071, vol. 157, No. 5, Publisher: The Journal of Infectious Diseases, Published in: US.

Dickenson, et al., "Conformational Changes in IpaD From Shigella Flexneri Upon Binding Bile Salts Provide Insight Into the Second Step of TY", Dec. 3, 2010, pp. 172-180, vol. 50, No. 2, Publisher: Biochemistry, Published in: US.

Dupont, et al., "Inoculum Size in Shigellosis and Implications for Expected Mode of Tranmission", Jun. 1989, pp. 1126-1128, vol. 159, No. 6, Publisher: The Journal of Infectious Diseases, Published in: US.

Epler, et al., "Liposomes Recruit IpaC to the Shigella Flexneri Type III Secretion Apparatus Needle . . . ", Jul. 2009, pp. 2754-5761, vol. 77, No. 7, Publisher: Infection and Immunity, Published in: US.

Espina, et al., "IpaD Localizes to the Tip of the Type III Secretion System Needle of Shigella Flexneri", Aug. 2006, pp. 4391-4400, vol. 74, No. 8, Published in: US.

Espina, et al., "Spectroscopic and Calorimetric Analyses of Invation Plasmid Antigen D (IpaD) . . . ", Jul. 11, 2006, pp. 9219-9227, vol. 45, No. 30, Publisher: Biochemistry, Published in: us.

Fontaine, et al., "Role of Shiga Toxin in the Pathogenesis of Bacillary Dysentery. . . . " Dec. 1988, pp. 3099-3109, vol. 56, No. 12, Publisher: Infection and Immunity, Published in: US.

Fries, et al., "Safety and Immunogenicity of a Proteosome-Shigella Flexneri 2a Lipopolysaccharide Vaccine Adminsitered Intranasally to H", Jul. 2001, pp. 4545-4553, vol. 69, No. 7, Publisher: Infection and Immunity, Published in: US.

Johnson, et al., "Expression, Limited Proteolysis and Preliminary Crystallographic Analysis of IpaD . . . ", Jul. 12, 2006, pp. 865-868, vol. F62, Publisher: Acta Crystallographica, Published in: US.

Kosek, et al., "Shigellosis Update: Advancing Antibiotic Resistance, Investment Empowered Vaccine . . . ", 2010, pp. 475-480, vol. 23, Publisher: Curr Opin Infect Dis , Published in: US.

Kotloff, et al., "Deletion in the Shigella Enterotoxin Genes Further Attenuates Shigella Flexneri 2a . . . ", Oct. 19, 2004, pp. 1745-1754, vol. 190, Publisher: The Journal of Infectious Diseases, Published in: US.

Kotloff, et al., "Global Burden of Shigella Infections: Implications for Vaccine Development and Implementation of Control Strategies", 1999, Publisher: Bulletin From World Health Organization, Published in: US.

Kotloff, et al., "Evaluation of the Safety, Immunogenicity, and Efficacy in Healthy Adults of Four Doses of Live Oral Hybrid . . . ", 1995, pp. 495-502, vol. 13, No. 5, Publisher: Vaccine, Published in: US.

Kotloff, et al., "Safety and Immunogenicity of CVD 1208S, A Live, Oral . . . ", 2007, pp. 268-275, vol. 3, No. 6, Publisher: Human Vaccines, Published in: US.

Kueltzo, et al., "Structure-Function Analysis of Invasion Plasmid Antigen C (IpaC) From Shigella Flexneri", Jan. 31, 2003, pp. 2792-2798, vol. 278, No. 5, Publisher: Journal FO Biological Chemistry, Published in: US.

Le-Barillec, et al., "Roles for T and NK Cells in the Innate Immune Response to Shigella Flexneri", 2005, pp. 1735-1740, vol. 175, Publisher: The Journal of Immunology, Published in: US.

Levine, et al., "Clinical Trials of Shigella Vaccines: Two Steps Forward and One Step Back on a Long Hard Road", Jul. 2007, pp. 540-553, vol. 5, Publisher: Nature Publishing Group, Published in: US.

Mach, et al., "Statistical Determination of the Average Values of the Extinction Coefficients of Tryptophan and Tyrosine in Native Prot", Jul. 24, 1991, pp. 74-80, Publisher: Analytical Biochemistry 200, Published in: US.

Mallett, et al., "Evaluation of Shigella Vaccine Safety and Efficacy in an Intransally Challenged Mouse Model", 1993, pp. 190-196, vol. 11, No. 2, Publisher: Vaccine, Published in: US.

Markham, et al., "Formulation and Immunogenicity of a Potential Multivalent Type III Secretion System-Based Protein Vaccine", May 18, 2010, pp. 4497-4509, vol. 99, No. 11, Publisher: Wiley Interscience, Published in: US.

McKenzie et al., "Safety and Immunogenicity of an Oral, Inactivated, Whole-Cell Vaccine for Shigella Sonnei: Preclinical Studies and a pH", Jul. 1, 2005, pp. 3735-3745, vol. 24, Publisher: Vaccine, Published in: US.

Menard, et al., "Extracellular Association and Cytoplasmic Partitioning of the IpaB and ipaC Invasions of S. Flexneri", Nov. 4, 1994, pp. 515-525, vol. 79, Publisher: CELL , Published in: US.

Morbidity and Mortality Weekly Report, "Vital Signs: Incidence and Trends of Infection with Pathogens . . . ", Jun. 10, 2011, pp. 749-755, vol. 60, No. 22, Publisher: Centers for Disease Control & Prevention, Published in: US.

Norton, et al., "Charaterization of a Mutant *Excherichia coli* Heat-Labile Toxin, LT(R192G/L211A), As a Safe and Effective Oral Adjuvant", Jan. 2, 2011, pp. 546-551, Publisher: Clinical and Vaccine Immunology, Published in: US.

Oaks, et al., "Development and Evaluation of a Shigella Flexneri 2a and S. Sonnei Bivalent Invasin Complex (INVAPLEX) Vaccine", Nov. 18, 2005, pp. 2290-2391, No. 24, Publisher: Vaccine, Published in: US.

Olive, et al., "Bile Salts Stimulate Recruitment of IpaB to the Shigella Flexneri Surface, . . . ", Feb. 12, 2007, pp. 2626-2629, vol. 75, No. 5, Publisher: Infection and Immunity, Published in: US.

Passwell, et al., "Safety and Immunogenicity of Improved Shigella O-Specific Polysaccharide-Protein Conjugate Vaccines in Adults in Israel", Mar. 2001, pp. 1351-1357, vol. 69, No. 3, Publisher: Infection and Immunity, Published in: US.

(56) References Cited

OTHER PUBLICATIONS

Qiu, et al., "Emergence of a Novel Shigella Flexneri Serotype 4s Strain That Evolved From a Serotype X Variant in China", Mar. 2011, pp. 1148-1150, vol. 49, No. 3, Publisher: Journal of Clinical Microbiology, Published in: US.

Rahman, et al., "Safety, Dose, Immunogenicity, and Transmissibility of an Oral Live Attenuated Shigella Flexneri 2a Vaccine. . . .", Oct. 30, 2010, pp. 1347-1354, vol. 29, Publisher: Vaccine, Published in: US.

Ramirez, et al, "Neonatal Mucosal Immunization With a Non-Living, Non-Genetically Modified Lactococcus Lactis Vaccine Carrier . . . ", Nov. 18, 2009, pp. 159-171, vol. 3, No. 2, Publisher: Immunology, Published in: US.

Ramirez, et al., "Mucosally Delivered Salmonella Typhi Expressing the Yersinia Pestis F1 Antigen Elecits Mucosal and Systemic . . . ", 2009, Publisher: The Journal of Immunology, Published in: US.
Raqib, et al., "Delayed and Reduced Adaptive Humoral Immune Responses in Chileren With Shigellosis Compared With in Adults", Jan. 18, 2002, pp. 414-423, vol. 55, Publisher: Scand. J. Immunol, Published in: Sweden.
Reed, W. P., "Serum Factors Capable of Opsonizing Shigella for Phagocytosis by Polymorphonuclear Neutrophils", Nov. 16, 1974, pp. 1051-1059, vol. 28, Publisher: Immunology, Published in: US.
Riddle, et al., "Safety and Immunogenicity of an Intranasal Shigella Flexneri 2a INVAPLEX 50 vaccine", Jul. 23, 2011, pp. 7009-7019, vol. 29, Publisher: Vaccine, Published in: US.
Samandari, et al., "Production of IFN-y and IL-10 to Shigella Invasins by Monoculear Cells From Volunteers Orally Inoculated With A . . . ", 2000, pp. 2221-2232, vol. 164, Publisher: The Journal of Immunology, Published in: US.
Simon, et al., "Antigen-Specific IgA B Memory Cell Responses to Shigella Antigens Elicited in Volunteers Immunized With Live Attenuated", Feb. 1, 2011, pp. 185-192, No. 139, Publisher: Clinical Immunology (2011), Published in: US.
Srinivasa, et al., "Magnitude of Drug Resistant Shigellosis: A Report From Bangalore", Nov. 7, 2009, pp. 358-360, Publisher: Indian Journal of Medical Microbiology, Published in: India.
Tackett, et al., "Efficacy of Bovine Milk Immunoglobulin Concentrate in Preventing Illness . . . ", 1992, pp. 276-283, Publisher: Am. J. Med. Hyg. , Published in: US.
Turbyfill, et al., "Isolation and Characterization of a Shigella Fexneri Invasin Complex Subunit Vaccine", Aug. 2000, pp. 6624-6632, vol. 68, No. 12, Publisher: Infection and Immunity, Published in: US.
Van De Verg, et al., "Antibody ANMD Cytokine Responses in a Mouse Pulmonary Model of Shigella Flexneri . . . ", May 1995, pp. 1947-1954, vol. 63, No. 5, Publisher: Infection and Immunity, Published in: US.
Walker, Richard I., "Considerations for Development of Whole Cell Bacterial Vaccines to Prevent Diarrheal Diseases in Children in Developing", Mar. 5, 2005, pp. 3369-3385, vol. 23, Publisher: Vaccine, Published in: US.

* cited by examiner

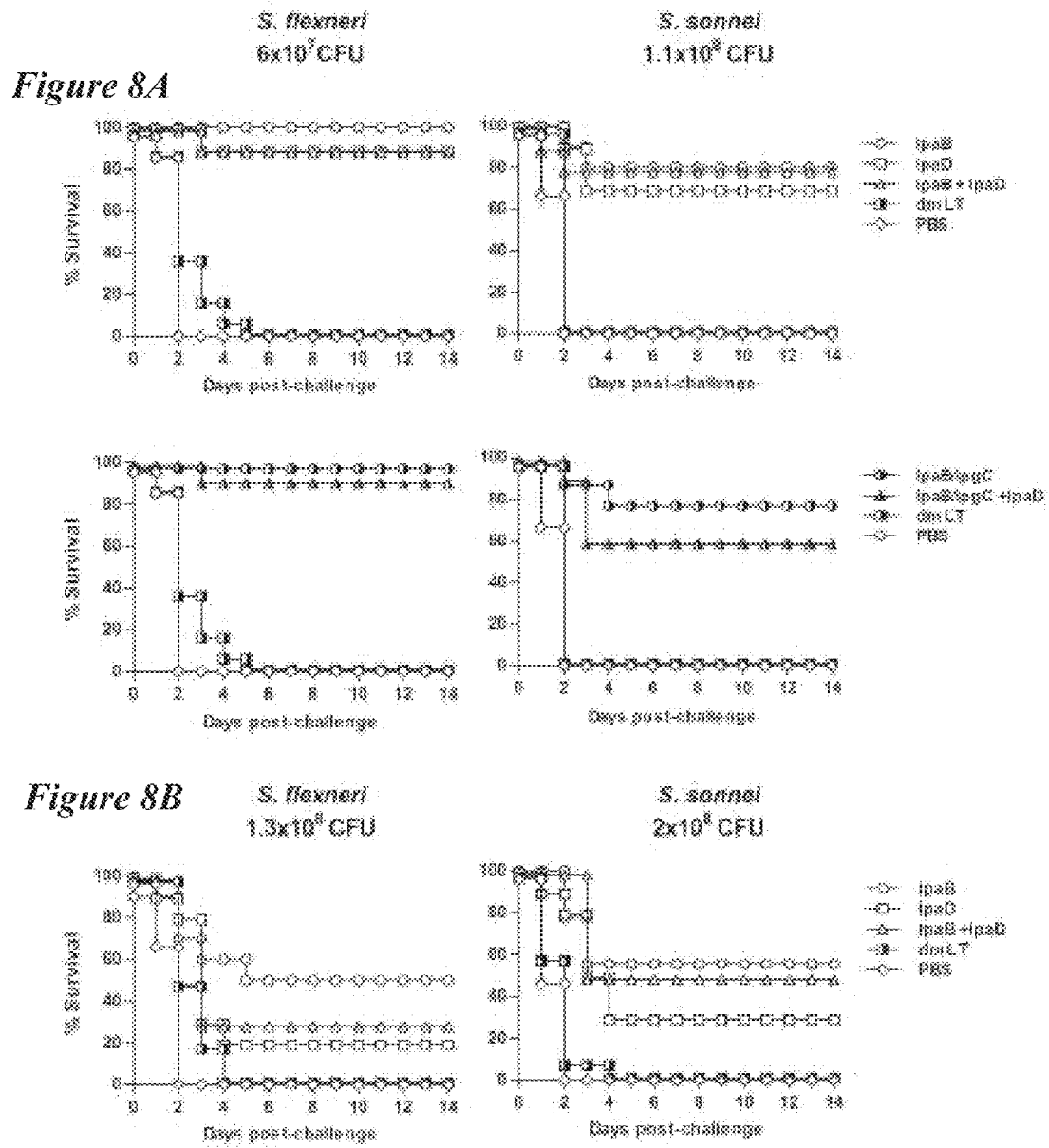

| Treatment | Vaccine Efficacy (%) | P value (vs dmLT control group) | P value (vs PBS control group) |
|---|---|---|---|
| IpaB +dmLT | 100 | <0.0001 | <0.0001 |
| IpaD +dmLT | 86 | <0.0001 | <0.0001 |
| IpaB +IpaD +dmLT | 90 | <0.0001 | <0.0001 |
| IpaB/IpgC +dmLT | 100 | <0.0001 | <0.0001 |
| IpaB/IpgC +IpaD +dmLT | 90 | <0.0001 | <0.0001 |

2L Autoinduction media for IpaD-IpaB/IpgC

*Figure 12A*

MHNVSTTTTGFPLAKILTSTELGDNTIQAANDAANKLFSLTIADLTANQNINTTNAHST
SNILIPELKAPKSLNASSQLTLLIGNLIQILGEKSLTALTNKITAWKSQQQARQQKNLE
FSDKINTLLSETEGLTRDYEKQINKLKNADSKIKDLENKINQIQTRLSNLDPESPEKKK
LSREEIQLTIKKDAAVKDRTLIEQKTLSIHSKLTDKSMQLEKEIDSFSAFSNTASAEQL
STQQKSLTGLASVTQLMATFIQLVGKNNEESLKNDLALFQSLQESRKTEMERKSDEYAA
EVRKAEELNRVMGCVGKILGALLTIVSVVAAAFSGGASLALAAVGLALMVTDAIVQAAT
GNSFMEQALNPIMKAVIEPLIKLLSDAFTKMLEGLGVDSKKAKMIGSILGAIAGALVLV
AAVVLVATVGKQAAAKLAENIGKIIGKTLTDLIPKFLKNFSSQLDDLITNAVARLNKFL
GAAGDEVISKQIISTHLNQAVLLGESVNSATQAGGSVASAVFQNSASTNLADLTLSKYQ
VEQLSKYISEAIEKFGQLQEVIADLLASMSNSQANRTDVAKAILQQTTA (SEQ ID NO: 1)

*Figure 12B*

MNITTLTNSISTSSFSPNNTNGSSTETVNSDIKTTTSSHPVSSLTMLNDTLHNIRTTNQ
ALKKELSQKTLTKTSLEEIALHSSQISMDVNKSAQLLDILSRNEYPINKDARELLHSAP
KEAELDGDQMISHRELWAKIANSINDINEQYLKVYEHAVSSYTQMYQDFSAVLSSLAGW
ISPGGNDGNSVKLQVNSLKKALEELKEKYKDKPLYPANNTVSQEQANKWLTELGGTIGK
VSQKNGGYVVSINMTPIDNMLKSLDNLGGNGEVVLDNAKYQAWNAGFSAEDETMKNNLQ
TLVQKYSNANSIFDNLVKVLSSTISSCTDTDKLFLHF (SEQ ID NO: 2)

*Figure 12C*

MSLNITENESISTAVIDAINSGATLKDINAIPDDMMDDIYSYAYDFYNKGRIEEAEVFF
RFLCIYDFYNVDYIMGLAAIYQIKEQFQQAADLYAVAFALGKNDYTPVFHTGQCQLRLK
APLKAKECFELVIQHSNDEKLKIKAQSYLDAIQDIKE (SEQ ID NO: 3)

MNITTLTNSISTSSFSPNNTNGSSTETVNSDIKTTTSSHPVSSLTMLNDTLHNIRTTNQ
ALKKELSQKTLTKTSLEEIALHSSQISMDVNKSAQLLDILSRNEYPINKDARELLHSAP
KEAELDGDQMISHRELWAKIANSINDINEQYLKVYEHAVSSYTQMYQDFSAVLSSLAGW
ISPGGNDGNSVKLQVNSLKKALEELKEKYKDKPLYPANNTVSQEQANKWLTELGGTIGK
VSQKNGGYVVSINMTPIDNMLKSLDNLGGNGEVVLDNAKYQAWNAGFSAEDETMKNNLQ
TLVQKYSNANSIFDNLVKVLSSTISSCTDTDKLFLHF<u>L</u>EMHNVSTTTTGFPLAKILTST
ELGDNTIQAANDAANKLFSLTIADLTANQNINTTNAHSTSNILIPELKAPKSLNASSQL
TLLIGNLIQILGEKSLTALTNKITAWKSQQQARQQKNLEFSDKINTLLSETEGLTRDYE
KQINKLKNADSKIKDLENKINQIQTRLSNLDPESPEKKKLSREEIQLTIKKDAAVKDRT
LIEQKTLSIHSKLTDKSMQLEKEIDSFSAFSNTASAEQLSTQQKSLTGLASVTQLMATF
IQLVGKNNEESLKNDLALFQSLQESRKTEMERKSDEYAAEVRKAEELNRVMGCVGKILG
ALLTIVSVVAAAFSGGASLALAAVGLALMVTDAIVQAATGNSFMEQALNPIMKAVIEPL
IKLLSDAFTKMLEGLGVDSKKAKMIGSILGAIAGALVLVAAVVLVATVGKQAAAKLAEN
IGKIIGKTLTDLIPKFLKNFSSQLDDLITNAVARLNKFLGAAGDEVISKQIISTHLNQA
VLLGESVNSATQAGGSVASAVFQNSASTNLADLTLSKYQVEQLSKYISEAIEKFGQLQE
VIADLLASMSNSQANRTDVAKAILQQTTA (SEQ ID NO: 4)

*Figure 12D*

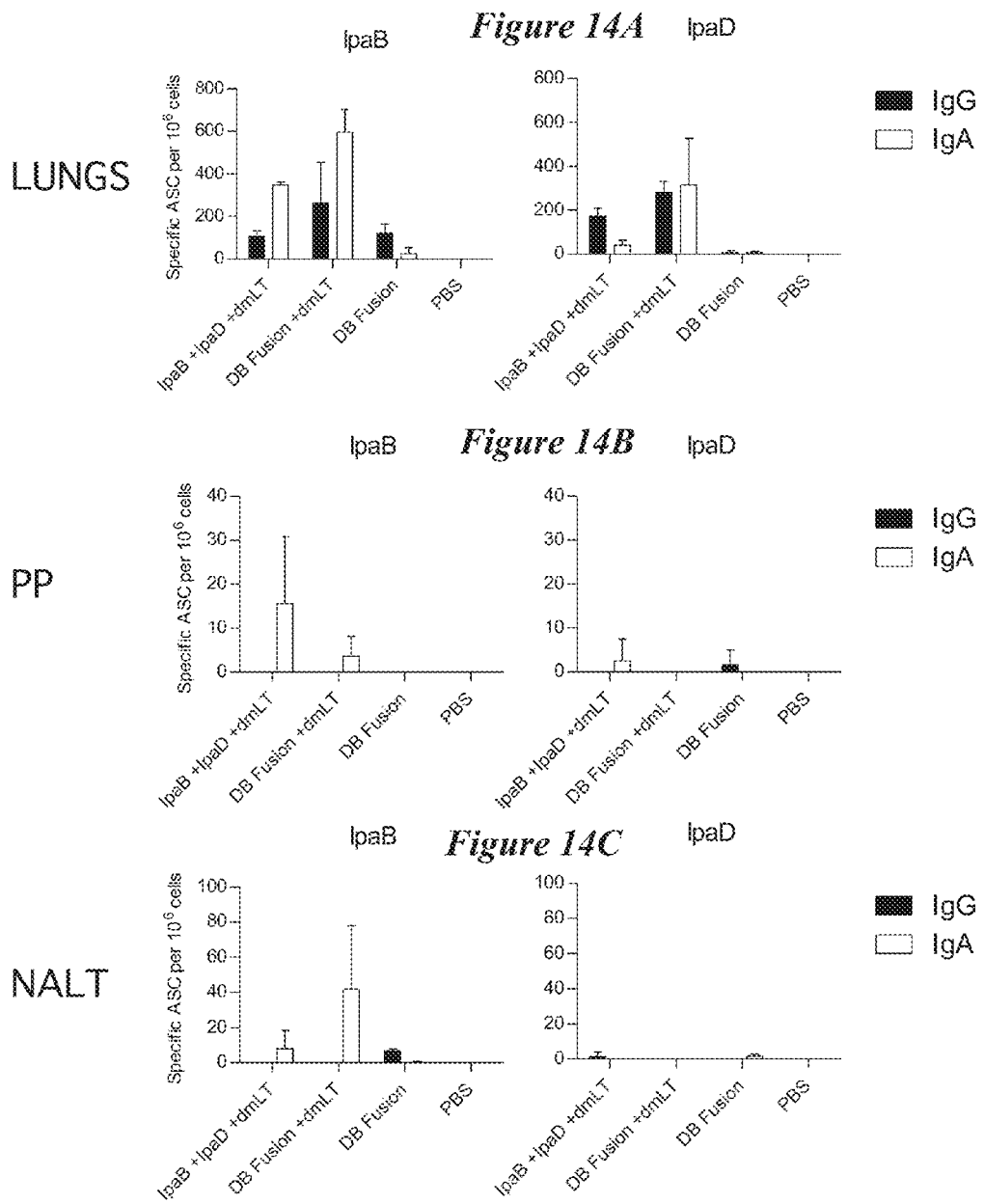

*Figure 21A*      *Figure 21B*
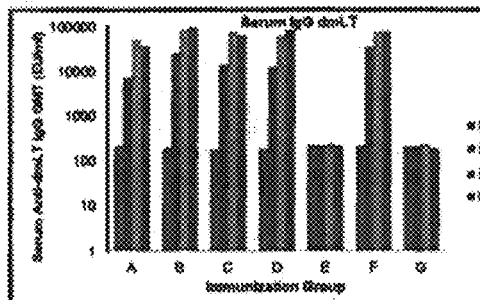 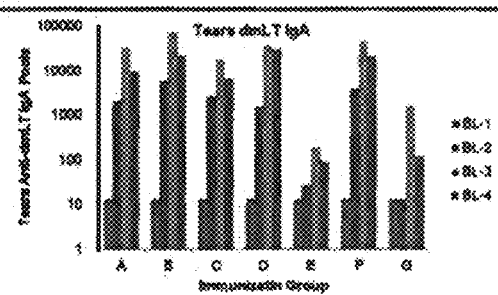
*Figure 22A*      *Figure 22B*
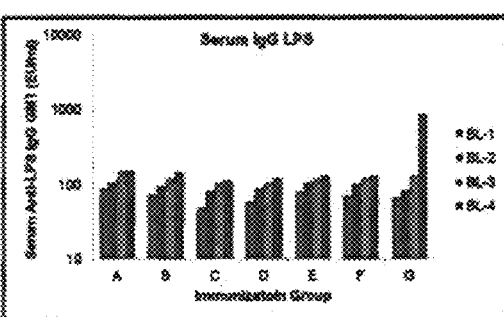 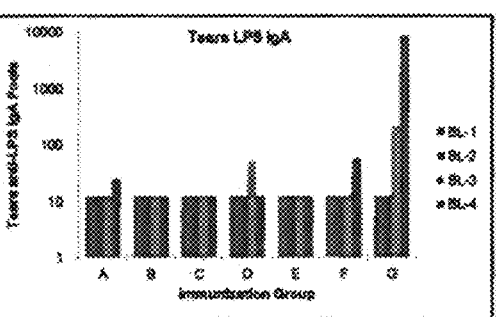
Groups (n=15)
1. IpaD (500 ng) + IpaB/IpgC (200 ng) + 100 ng dmLT High (ID)
2. IpaD (250 ng) + IpaB/IpgC (100 ng) + 100 ng dmLT Medium (ID)
3. IpaD (100 ng) + IpaB/IpgC (50) + 100 ng dmLT Low (ID)
4. Positive control: IpaD (10 μg) + IpaB/IpgC (2.5 μg) + 2.5 μg dmLT (i.n.)
5. dmLT (100 ng) (ID)
6. PBS (ID)
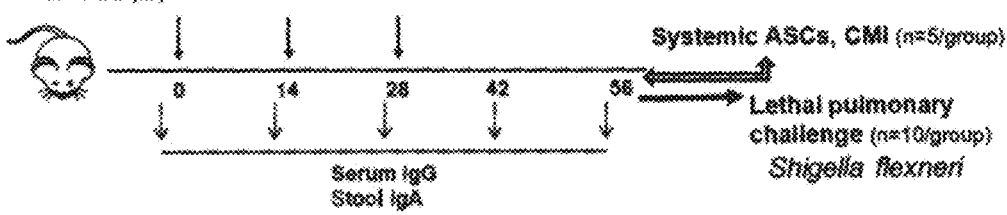
*Figure 23*

IpaB

IpaD dmLT

IpaB

IpaD dmLT

IpaB

IpaD dmLT

IpaB

IpaD

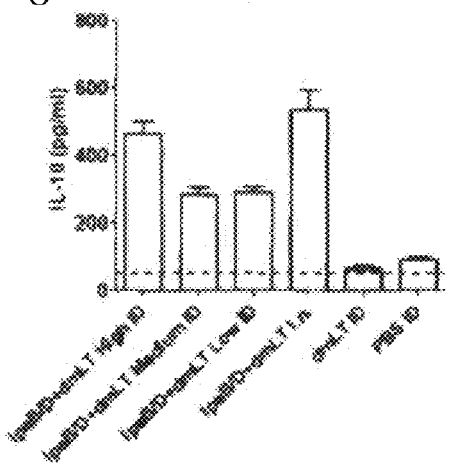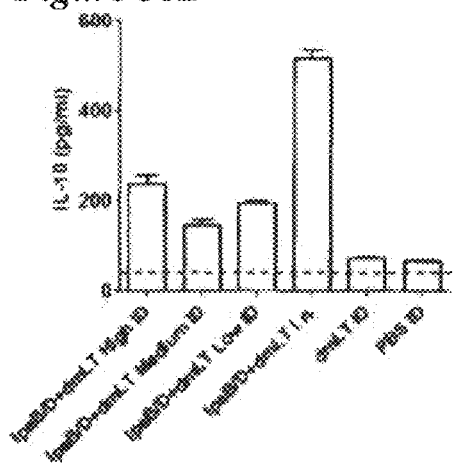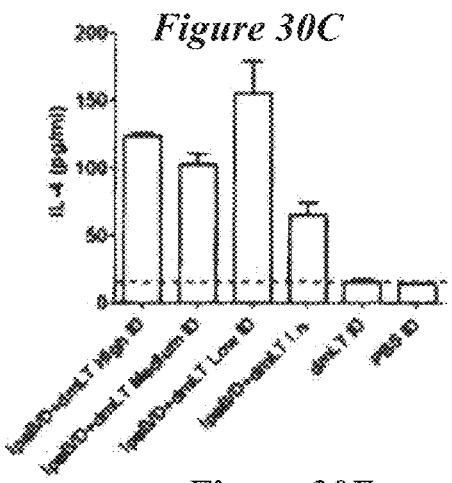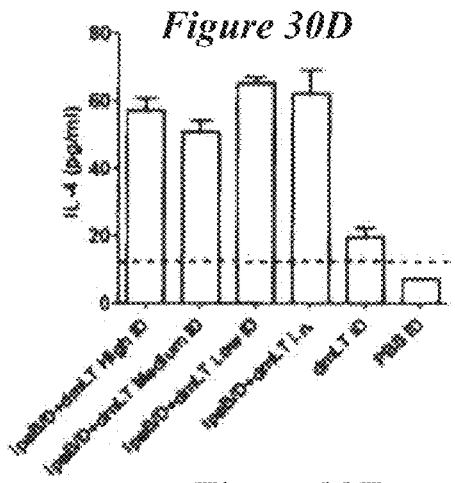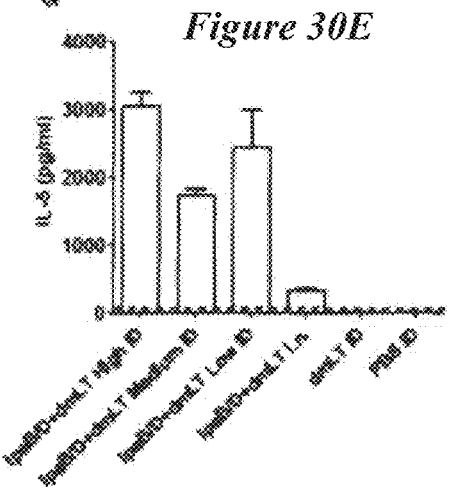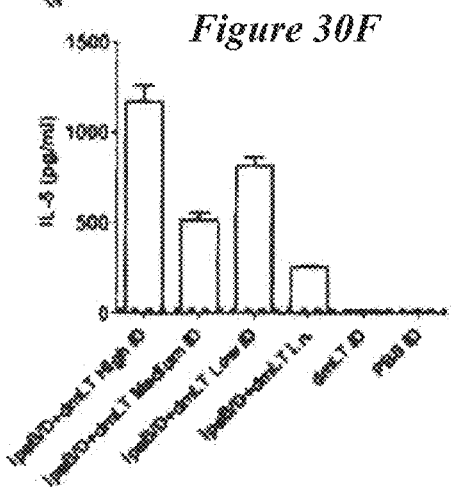

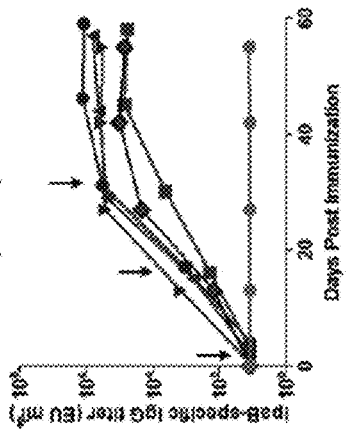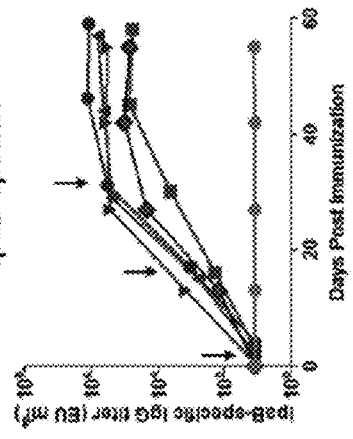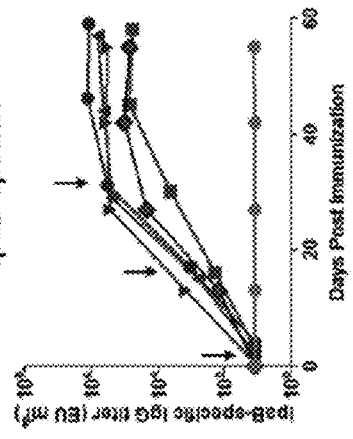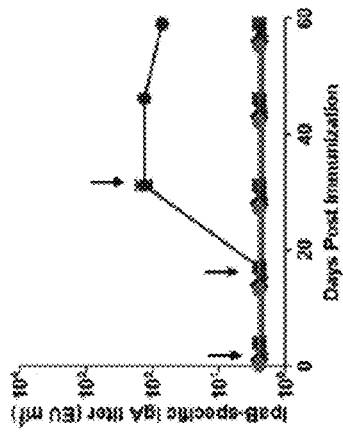
Figure 32A  Figure 32B  Figure 32C

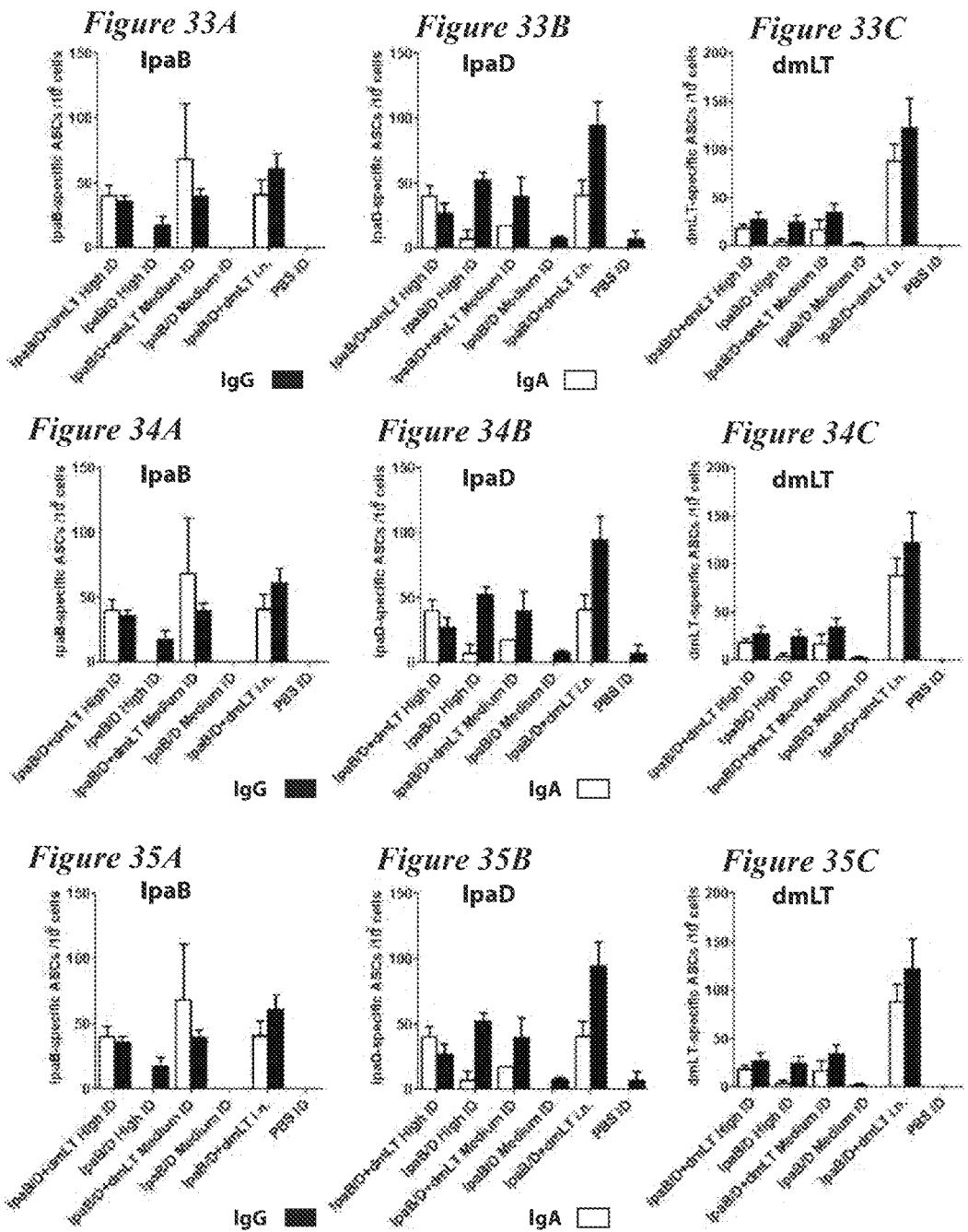

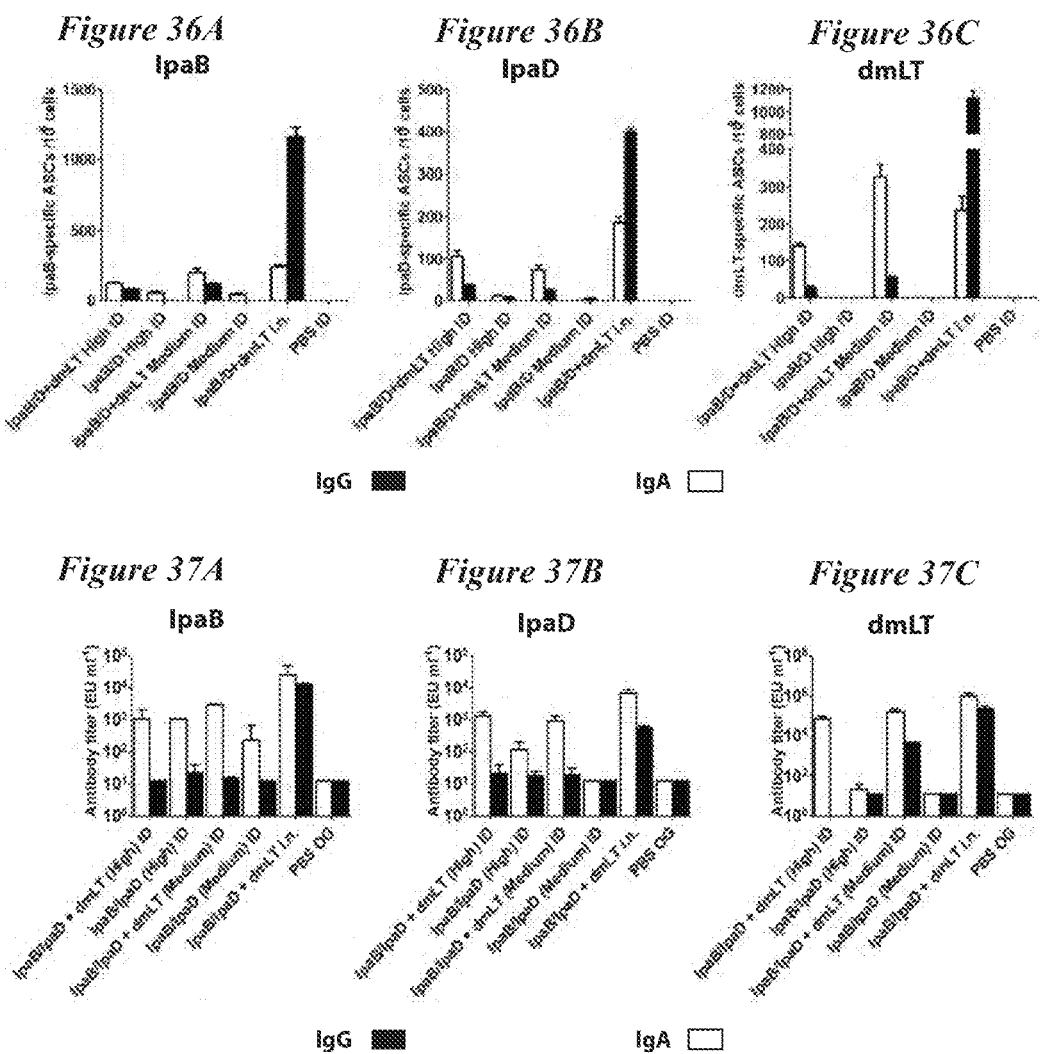

BROADLY PROTECTIVE *SHIGELLA* VACCINE BASED ON TYPE III SECRETION APPARATUS PROTEINS

CROSS REFERENCE TO RELATED APPLICATION

This application claims the benefit of U.S. Provisional Patent Application Ser. No. 61/568,918 filed on Dec. 9, 2011, and incorporates said provisional application by reference into this document as if fully set out at this point.

SEQUENCE LISTING

This application includes as the Sequence Listing the complete contents of the accompanying text file "Sequence.txt", created Dec. 7, 2011, containing 17,471 bytes, hereby incorporated by reference.

FIELD OF THE INVENTION

The invention generally relates to broad based, cross-protective, O-serotype independent vaccines against *Shigella*. In particular, the invention provides broadly protective *Shigella* vaccines comprising one or more of the type III secretion (TTS) apparatus needle proteins IpaD and IpaB, and/or the IpaB cognate chaperone protein IpgC, and/or chimeric proteins thereof.

BACKGROUND OF THE INVENTION

Shigellosis is a severe diarrheal disease caused by infection by bacteria of the genus *Shigella*. Shigellosis is associated with high morbidity and mortality rates, particularly in the developing world. It is also responsible for long-term effects on cognitive and physical development in children. The global burden has been estimated at more than 160 million cases per year; the most affected being children under 5 years of age living in endemic areas. The causative agent can be transmitted from person to person through fecal-oral contact or through contaminated fomites; ingestion of as few as 10 organisms can cause illness in adult volunteers. In industrialized countries, *Shigella* is known to be responsible for cases of pediatric diarrhea and to cause occasional foodborne outbreaks. Other susceptible groups include travelers, military personnel and refugees. Additionally, the Centers for Disease Control and Prevention lists *Shigella* as a food safety threat.

The *Shigella* genus comprises four different species: *Shigella dysenteriae, Shigella flexneri, Shigella sonnei* and *Shigella boydii*. These organisms are further divided into multiple serotypes, based on the structure of the O-polysaccharide portion of their outer membrane lipopolysaccharide (LPS), thereby increasing their antigenic variability. One serotype in particular, *S. dysenteriae* serotype 1, which produces Shiga toxin, is responsible for the most severe infections, including hemolytic uremic syndrome and it is the cause of epidemic dysentery. Additionally, serotypes can drift during outbreaks, further limiting the efficacy of vaccines that are restricted to particular serotypes. The emergence of strains resistant to antimicrobial drugs, including ciprofloxacin, currently the first-line antibiotic treatment against *Shigella* infections, heightens the difficulty of controlling this pathogen and makes the development of an effective vaccine even more urgent.

Despite being a longstanding priority for the World Health Organization, and the progress made in recent years, no licensed vaccine for *Shigella* spp. currently exists. Efforts to develop a vaccine against this pathogen have included the use of killed bacteria, live attenuated and recombinant carrier organisms, polysaccharide conjugates and LPS/protein mixtures. When tested in humans, these vaccines were either too reactogenic or poorly immunogenic. A major disadvantage of these candidates is the O antigen restriction, which limits the scope of protection they can offer and requires the development of a multi-serotype vaccine to provide adequate protective coverage in *Shigella* endemic areas.

The type III secretion system (TTSS) is a common virulence mechanism in many Gram-negative pathogens. Resembling a molecular needle and syringe, the TTSS apparatus provides a conduit for the translocation of effector proteins from the bacterial cytoplasm to the host cell cytoplasm. Residing atop the TTSS needle tip is a tip complex composed of IpaB and IpaD sequentially assembled, which is required for pathogenesis. Several studies have reported the presence of antibodies against Ipa proteins in serum from infected individuals, in subjects immunized with live attenuated organisms during clinical trials and following vaccination in animal models. The conserved nature of the IpaB and IpaD and their critical role in pathogenesis make them ideal targets for vaccine development. An Ipa-based vaccine would provide broader coverage across multiple serotypes. It would also simplify vaccine production and formulation.

SUMMARY OF THE INVENTION

The present invention provides broad-based, protective O antigen-independent vaccines against *Shigella* and related pathogens. The vaccines are advantageously not subject to O antigen restriction and thus may be used to confer protection against a wide range of *Shigella* species and related pathogens. The vaccines have been developed using the surface-exposed proteins at the tip of the type III secretion (TTS) apparatus needle from *Shigella*, as well as a cognate chaperone protein. The two TTS apparatus needle tip proteins from *Shigella* are the initial tip protein IpaD and the first 'translocator') protein IpaB. Within the cytoplasm of *Shigella*, IpaB forms a complex with its cognant chaperone IpgC. For vaccines, recombinant IpaB was prepared with its chaperone by co-expression in *E. coli* and co-purification via column chromatography. In addition, IpaB was prepared alone by inducing its release from the chaperone using various detergents, thereby leaving IpaB for independent purification. Thus, the IpaB/IpgC complex, IpaB alone, and IpaD were examined as protective antigens by immunizing mice intranasally and challenging the mice with *S. flexneri* and *S. sonnei*. The challenge results showed that all three of these antigen preparations (individually and/or in combination) were effective in protecting the mice against homologous *S. flexneri* challenge and heterologous (O-serotype independent) *S. sonnei* challenge. This discovery provides a significant advancement over the live-attenuated and lipopolysaccaride-based vaccines that are currently being tested. In some embodiments, the proteins are advantageously adminstered as chimeric proteins which comprise two or more of the proteins encompassed in single recombinant protein vaccine.

BRIEF DESCRIPTION OF THE DRAWINGS

FIG. 1. SDS-PAGE of purified recombinant proteins. IpaD (lane 1), IpaB (lane 2) and IpaB/IpgC (lane 3) (5 μg)

were subjected to SDS-PAGE and subsequently stained with Coomassie Blue R-250. Molecular weight markers (in kDa) are on the left.

FIG. 2. CD spectroscopy of recombinant proteins. (A) Far-UV spectra of recombinant proteins were recorded at 10° C. in 10 mM phosphate/citrate buffer at pH 7.2. (B) Temperature dependence of the molar ellipticity at 222 nm of recombinant proteins was monitored from 10° C. to 90° C. at 2.5° C. intervals at a rate of 15° C./h. Error bars have been omitted for clarity; uncertainty was less than 5% (n=3).

Figure 3A:
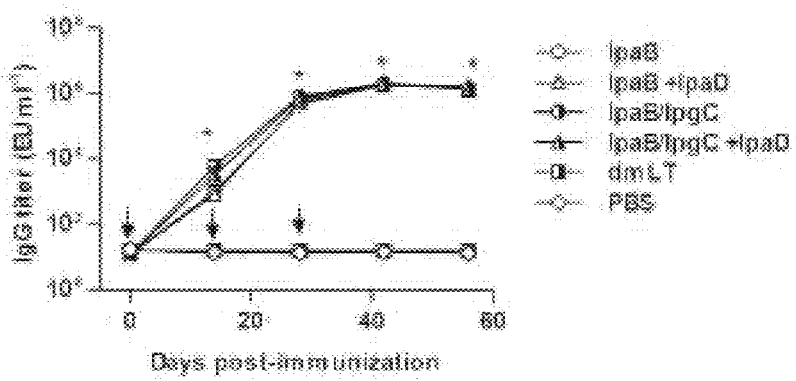
Figure 3B:
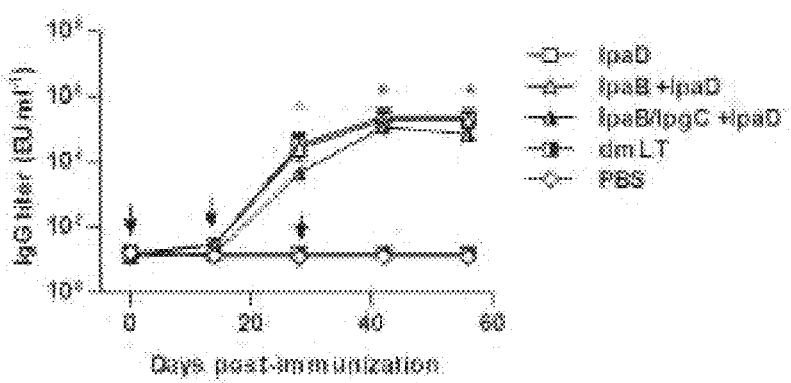
Figure 3C:
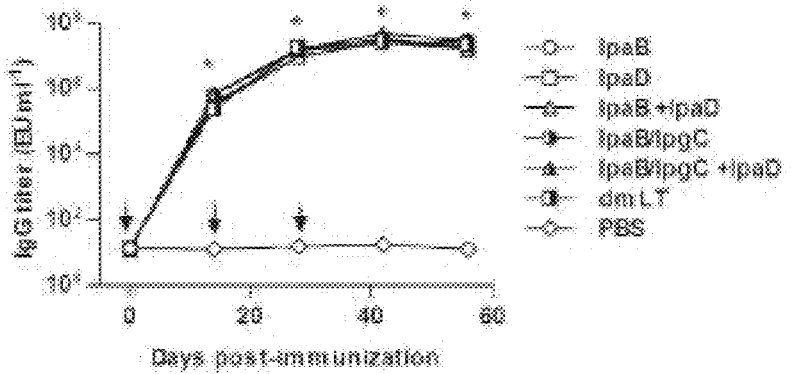

FIG. 3. Serum antibody responses to IpaB, IpaD and dmLT. Mice were immunized on day 0, 14 and 28 (arrows). Serum IgG antibodies specific for IpaB (A), IpaD (B) and dmLT (C) were measured by ELISA. Data represents mean titers (EU ml-1)±SE from 10 mice per group. * P<0.05 vaccinated vs. PBS controls.

FIG. 4. Antibody secreting cells in spleen and bone marrow. Spleens (A) and bone marrows (B) were collected on day 56. Single cell suspensions from 5 mice per group were stimulated in vitro with IpaB or IpaD. IgG and IgA ASC were measured by ELISpot. Bars represent mean ASC per 106 cells+SD from replicate wells. * P<0.05 vs. PBS control mice.

Figure 5A:
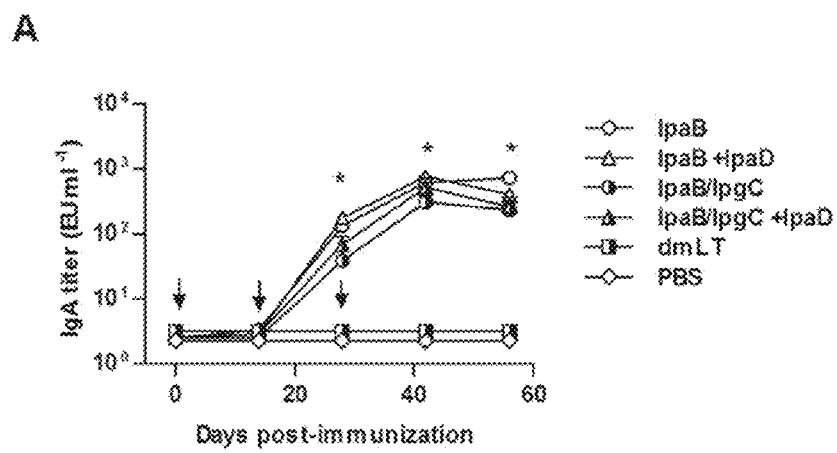
Figure 5B:
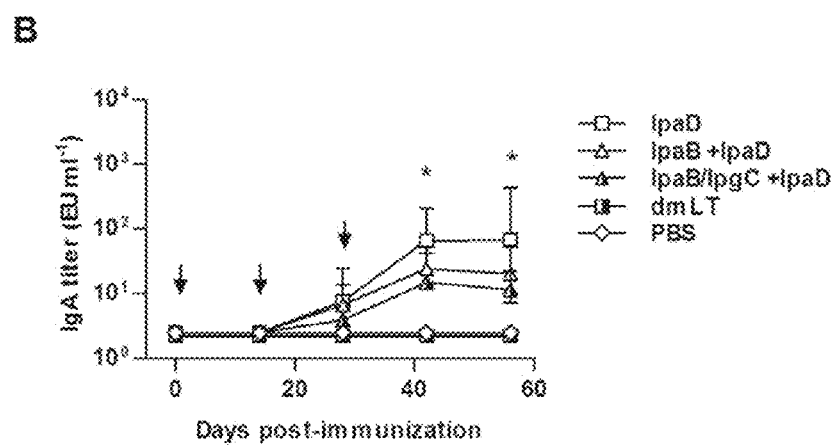
Figure 5C:
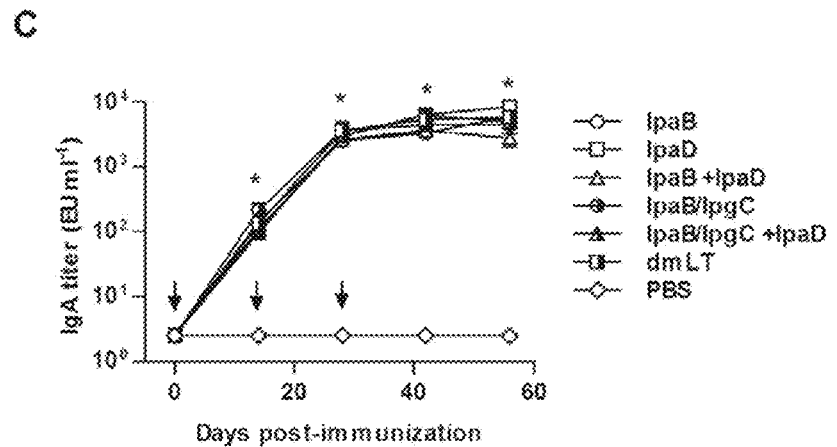

FIG. 5. Fecal IgA responses to IpaB, IpaD and dmLT. Mice were immunized on day 0, 14 and 28 (arrows). IgA specific for IpaB (A), IpaD (B) and dmLT (C) was measured by ELISA in stool supernatants. Data represents mean titers (EU ml-1)±SE from 10 mice per group, except for day 56, which included 5 mice in each group. * P<0.05 vs. PBS control mice.

Figure 6:
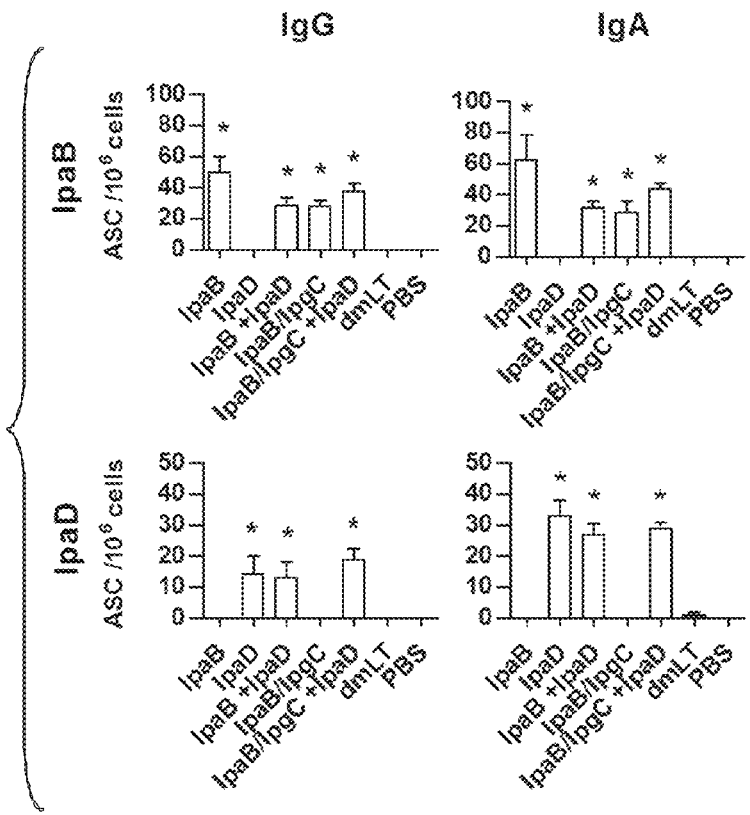

FIG. 6. Antibody secreting cells in nasal tissue. Nasal associated lymphocyte tissue was collected on day 56 and single cell suspensions were prepared from 5 mice per group. IgG and IgA ASC specific IpaB and IpaD were measured by ELISpot. Bars represent mean±SD per 106 cells from replicate wells. * P<0.05 vs. PBS control mice.

Figure 7:
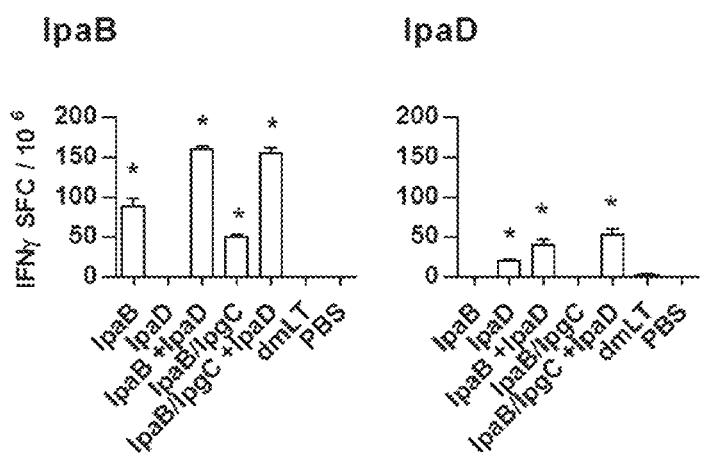

FIG. 7. IFN-γ secreting cells. Spleens were collected on day 56 from 5 mice per group. Single cell suspensions were prepared and stimulated with 5 µg/ml IpaB or IpaD for 48 h. Results are shown as IFN-γ SFC per 106 cells+SD from quadruple wells * P<0.05 vs. mice that received PBS.

FIG. 8. Protection against Shigella ssp. in a lethal pulmonary challenge. Mice were challenged on day 56 after the first immunization. Two dosage levels were used for each strain: 6×107 CFU of S. flexneri, corresponding to ~11 MLD50, and 1.1×108 CFU of S. sonnei (~5 MLD50) (A); 1.3×108 CFU of S. flexneri, corresponding to ~24 MLD50 and 2×108 CFU of S. sonnei (~9 MLD50) (B). Data represent survival curves from 10 mice per group.

Figures 9A, 9B:
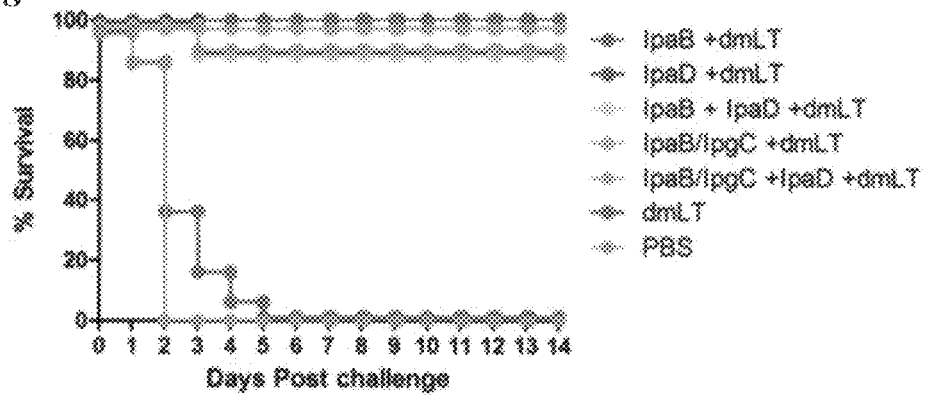

FIGS. 9A and B. Protective efficacy of IpaB/D proteins against S. flexneri pulmonary challenge. A, Percent survival; B, vaccine efficacy.

Figures 10A, 10B:
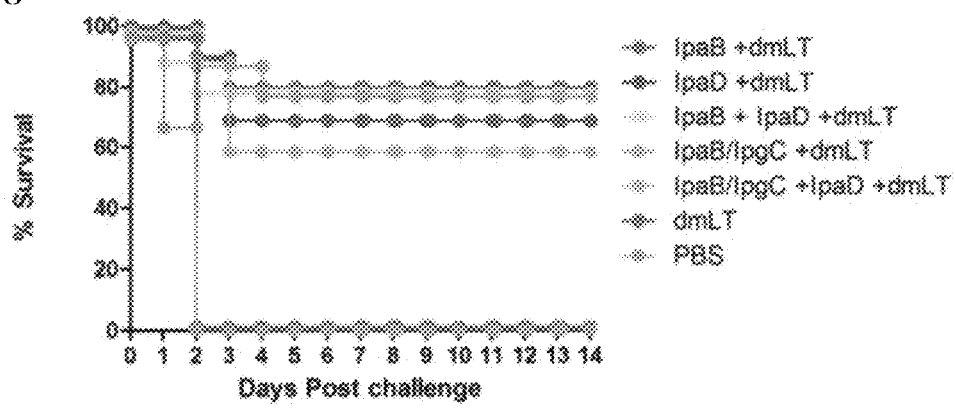

FIG. 10. Protective efficacy of IpaB/D proteins against S. sonnei pulmonary challenge. A, Percent survival; B, vaccine efficacy.

Figure 11:
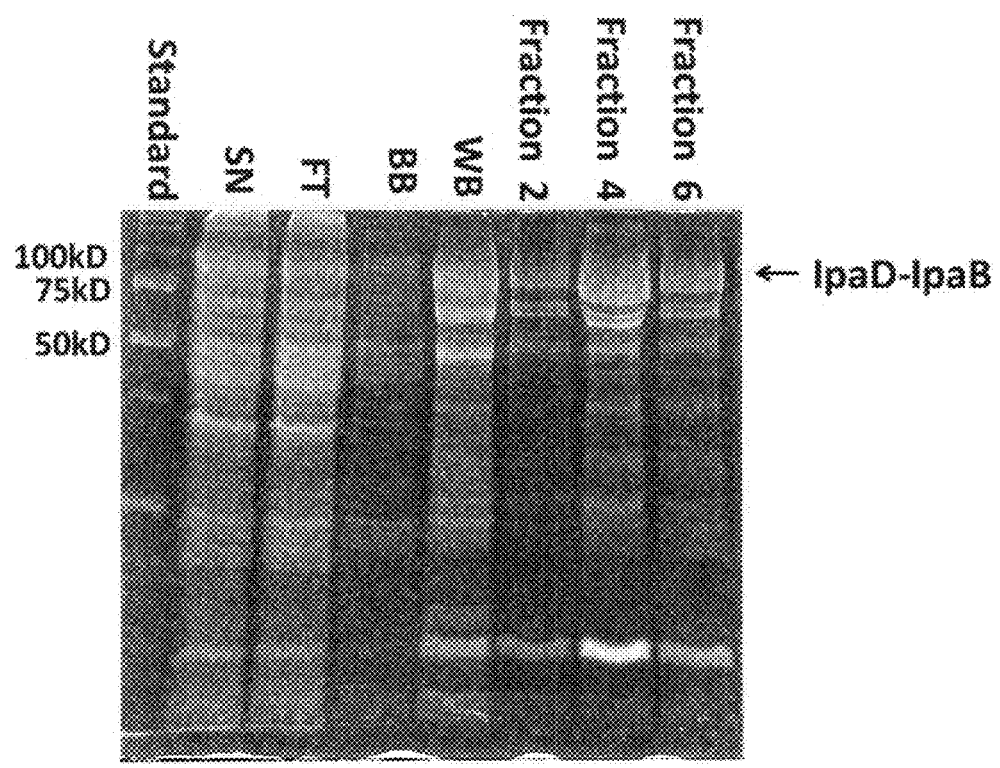

FIG. 11. SDS-PAGE of IpaD-IpaD chimeric protein.

FIG. 12A-D. Amino acid sequence of full length proteins for A, IpaB (SEQ ID NO: 1); B, IpaD (SEQ ID NO: 2); C, IpgC (SEQ ID NO: 3); D, fusion protein of IpaD and IpaB (SEQ ID NO: 4).

Figure 13A:
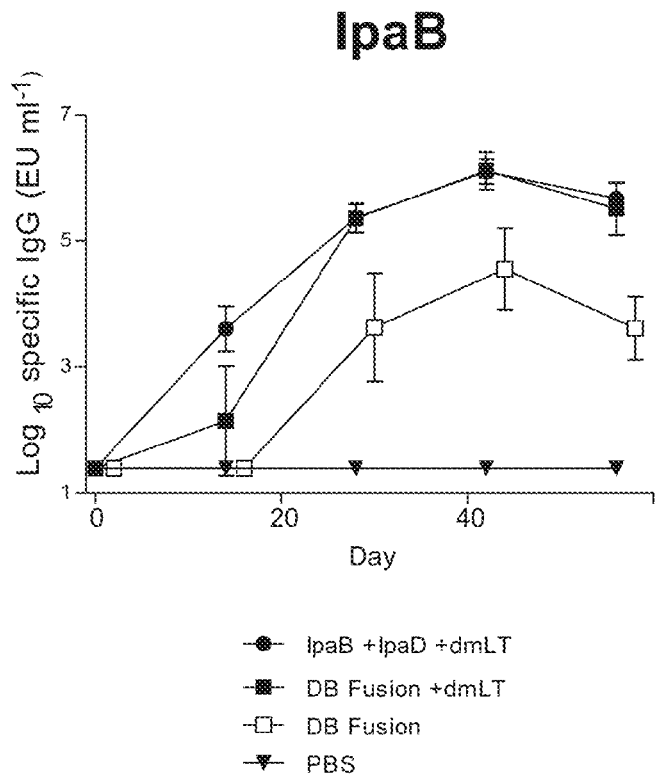

FIGS. 13A and B. Serum IgG levels in mice at the indicated intervals. A, IgG reactive with IpaB; B, IgG reactive with IpaD.

FIG. 14A-E. Levels of IgG and IgA in response to DB fusion administration as detected by IpaB and IpaD antibodies in: A, lungs; B, Peyer's patches (PP); C, nasal associated lymphoid tissue (NALT); D, spleen; and E, bone marrow.

Figure 15A:
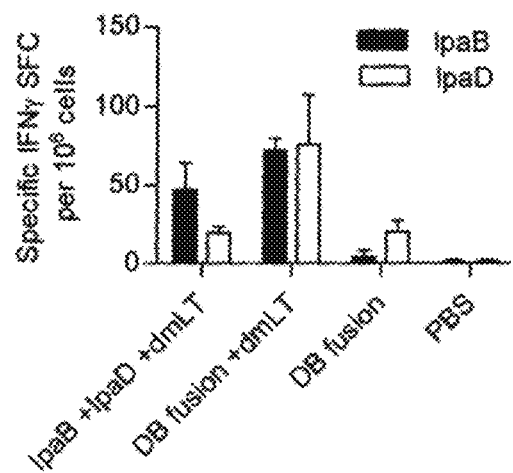
Figure 15B:
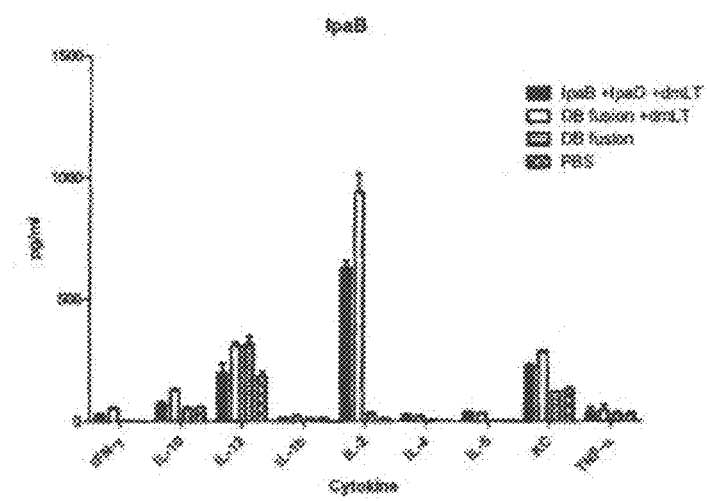
Figure 15C:
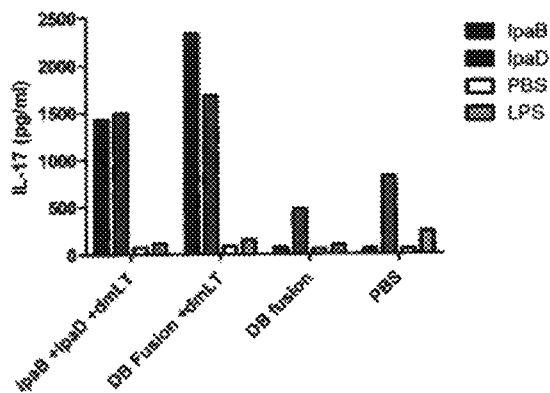

FIG. 15A-C. A, IFN-γ secreting cells; B, cytokine secretion; and C, IL-17 secretion.

Figure 16:
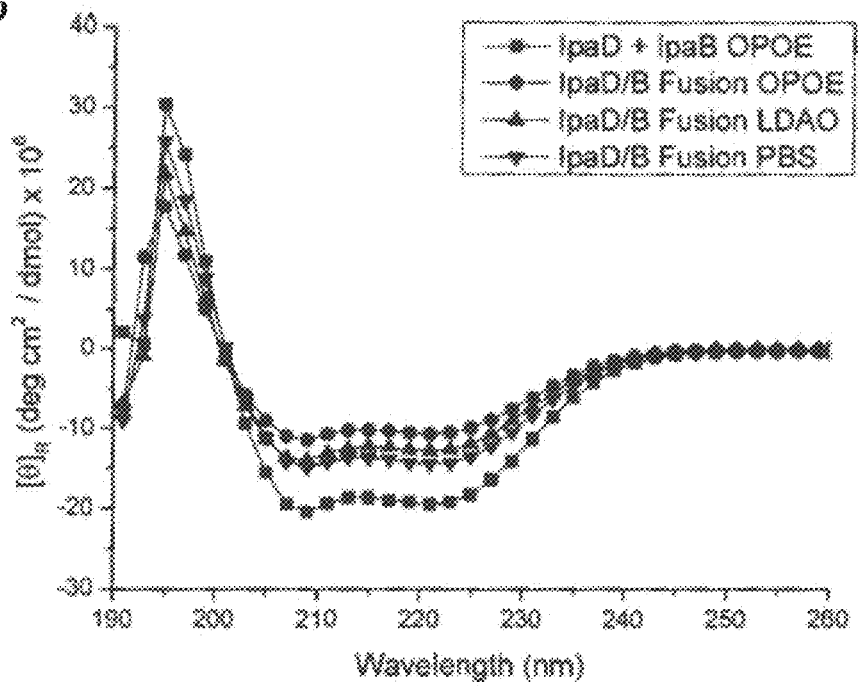

FIG. 16. Detergent effects on IpaD/B fusion protein structure measured by circular dichroism (CD).

Figure 17:
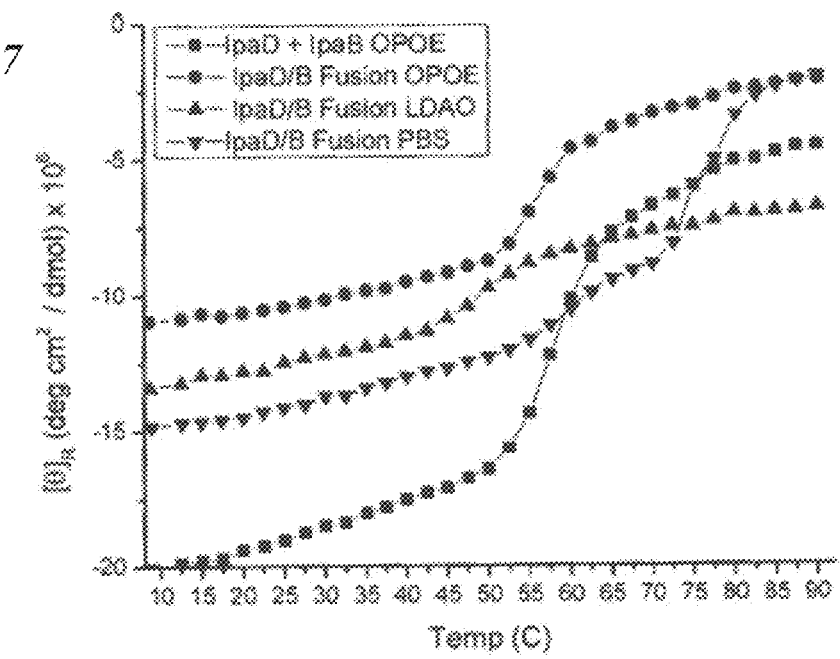
Figure 18A:
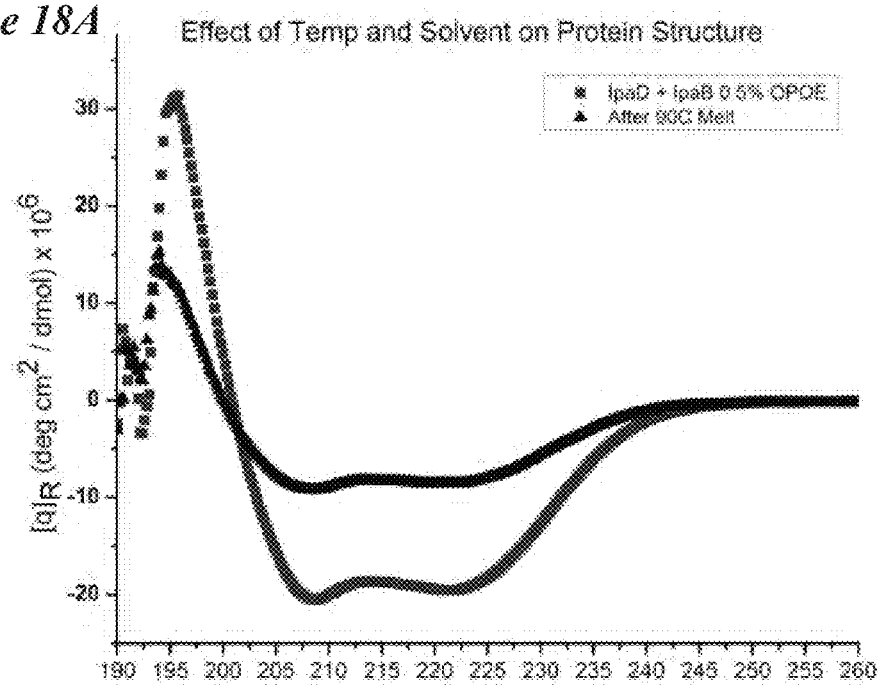
Figure 18B:
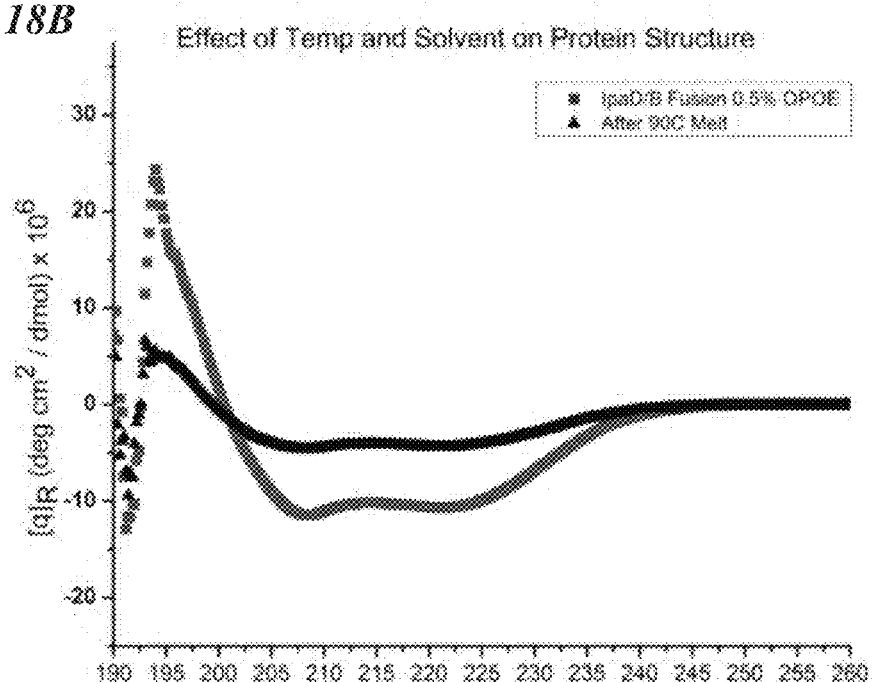
Figure 18C:
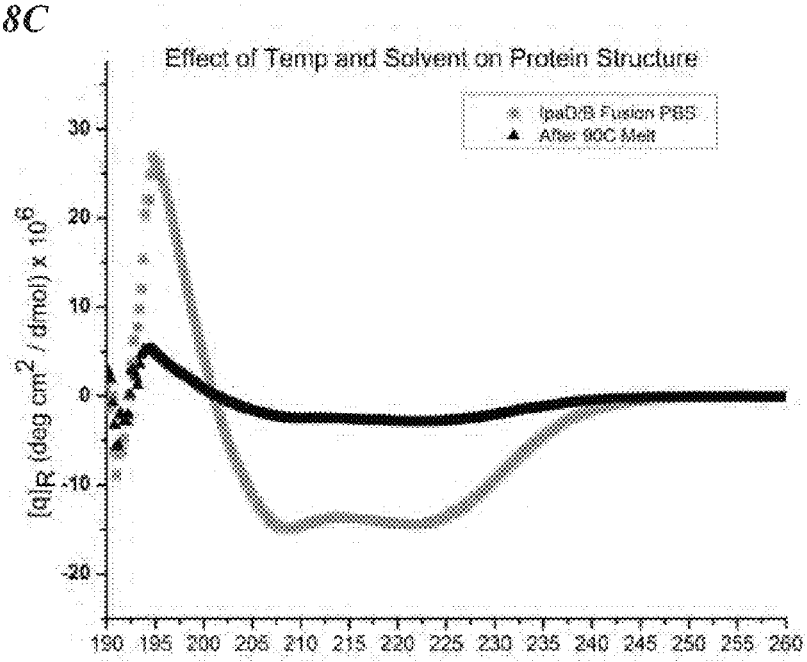
Figure 18D:
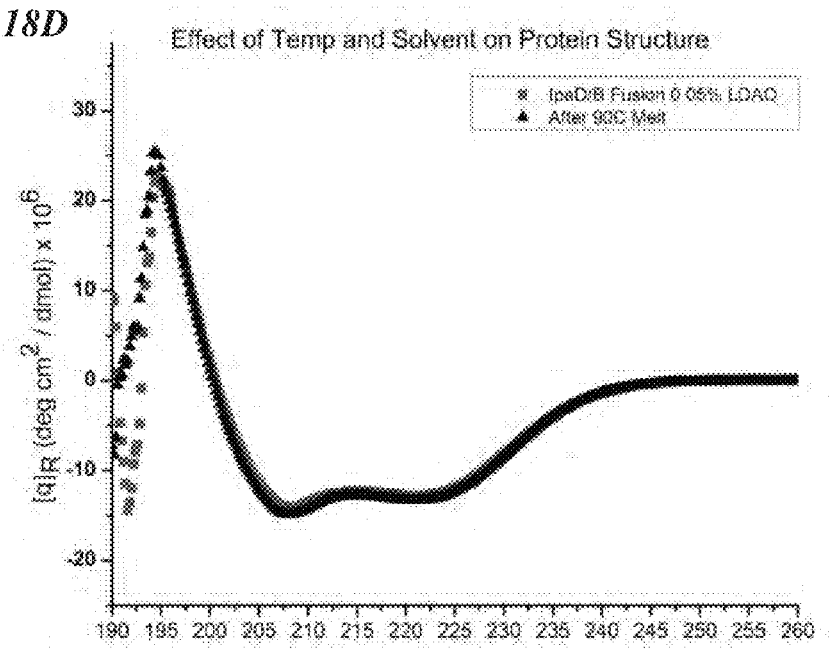

FIG. 17. CD thermal melts of DB fusion protein.

FIG. 18A-D. CD profiles before and after heating to 90° C. A, IpaD+PpaB in 0.5% OPOE; B, IpaB/B fusion in 0.5% OPOE; C, B/B fusion in PBS; D, IpaB/B fusion in LDAO.

Figure 19A:
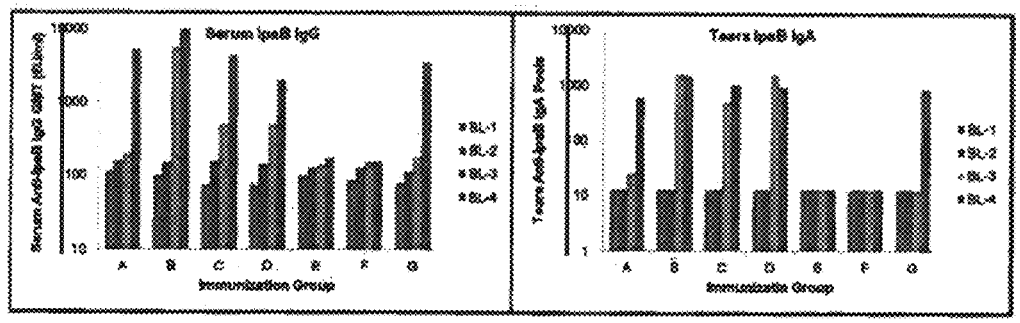

FIGS. 19A and B. Serum and mucosal antibody responses to IpaB. Serum IgG GMTs (A) and mucosal IgA titers in pooled tears (B) are shown for each immunization group for each subsequent collection. BL-1, pre-immune titer; BL-2, post 1 dose; BL-3, post 2 doses; and BL-4, post 3 doses.

Figure 20A:
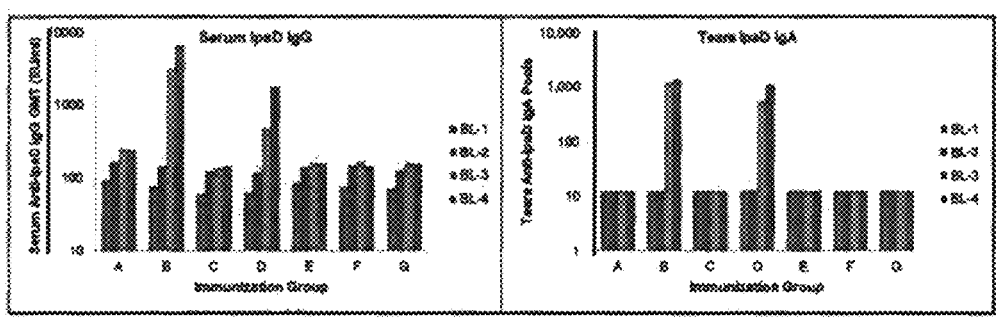

FIGS. 20A and B. Serum and mucosal antibody responses to IpaD. Serum IgG GMTs (A) and mucosal IgA titers in pooled tears (B) are shown for each immunization group for each subsequent collection. BL-1, pre-immune titer; BL-2, post 1 dose; BL-3, post 2 doses; and BL-4, post 3 doses.

FIGS. 21A and B. Serum and mucosal antibody responses to dmLT. Serum IgG GMTs (A) and mucosal IgA titers in pooled tears (B) are shown for each immunization group for each subsequent collection. BL-1, pre-immune titer; BL-2, post 1 dose; BL-3, post 2 doses; and BL-4, post 3 doses.

FIGS. 22A and B. Serum and mucosal antibody responses to S. flexneri 2a LPS. Serum IgG GMTs (A) and mucosal IgA titers in pooled tears (B) are shown for each immunization group for each subsequent collection. BL-1, pre-immune titer; BL-2, post 1 dose; BL-3, post 2 doses; and BL-4, post 3 doses.

FIG. 23. Schematic of challenge experiment.

Figures 24A, 24B, 24C:
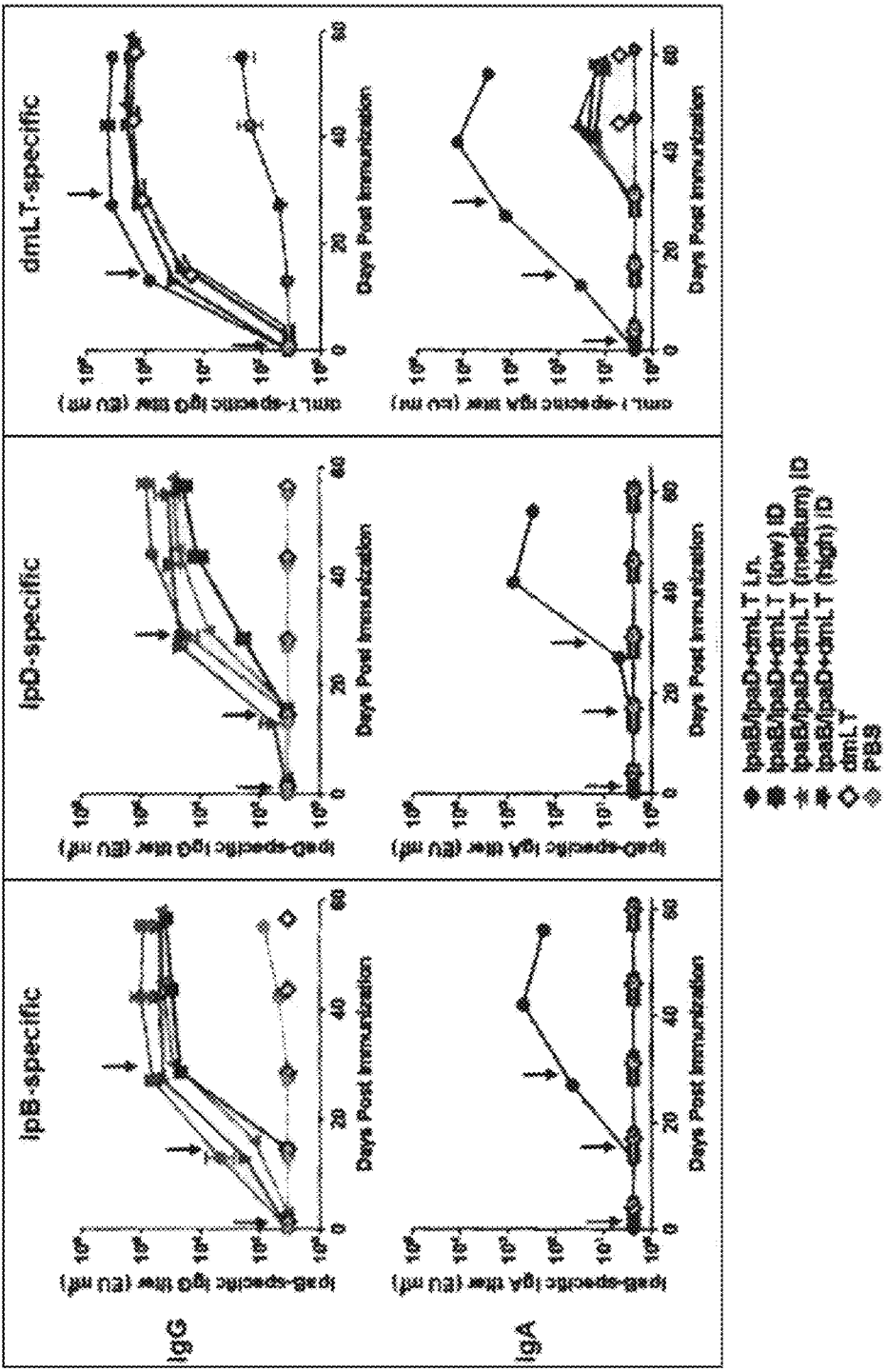

FIG. 24A-C. Kinetics of serum A, IpaB-, B, IpaD-, and C, dmLT-specific IgG antibodies and stool IpaB-, IpaD-, and dmLT-specific IgA antibodies. Mice were immunized with IpaB and IpaD, along with dmLT on days 0, 14 and 28 (see FIG. 23). Serum IgG and stool IgA antibody titers were measured by ELISA. Data represent mean titers±SEM of individual samples from each group.

Figure 25A:
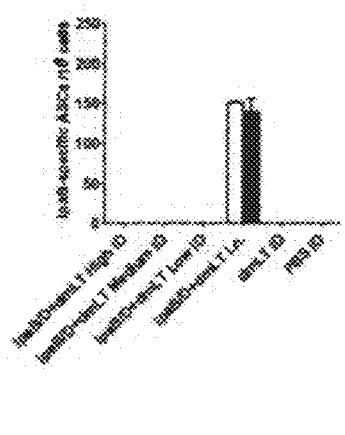
Figure 25B:
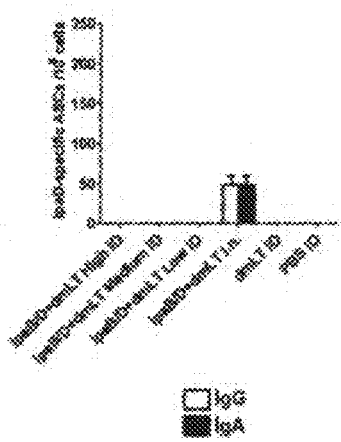
Figure 25C:
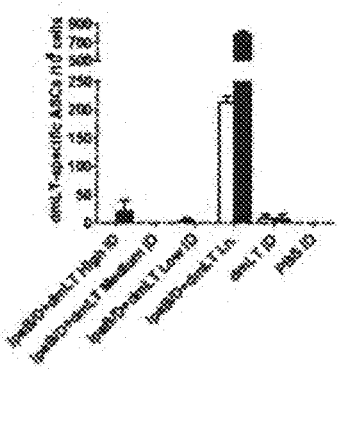

FIG. 25A-C. A, IpaB-, B, IpaD- and C, dmLT-specific IgG and IgA ASCs in lungs. Mice were immunized as described in Example 4. Lungs were collected from 5 mice in each group on day 5 and single cell suspensions prepared. Viable lymphocytes were separated using Lympholyte density gradient. The frequencies of IgA and IgG ASC were measured by ELISpot. Results are shown as mean IgG (white bars) or IgA (black bars) IpaB-, IpaD- and dmLT-specific ASCs per 106 cells+SEM from wells in triplicate (lungs for each group were pooled).

Figure 26A:
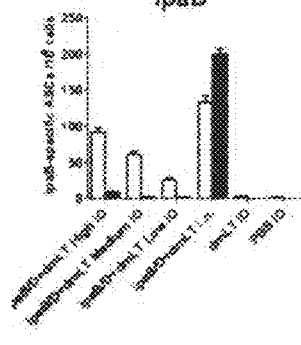
Figure 26B:
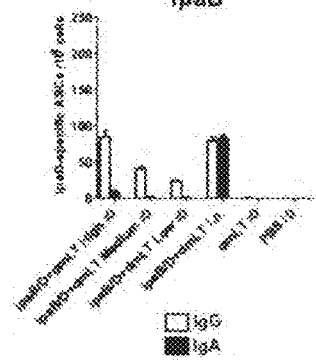
Figure 26C:
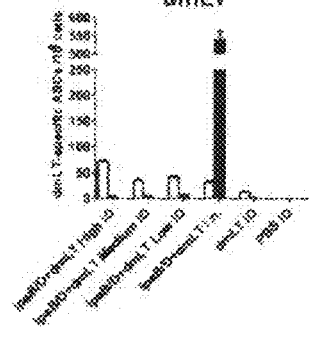

FIG. 26A-C. Spleen A, IpaB-, B, IpaD- and C, dmLT-specific IgG and IgA ASCs. Mice were immunized as described in Example 4. Spleens were collected on day 56 from 5 mice in each group and single cell suspensions prepared. The frequencies of IgA and IgG ASC were measured by ELISpot. Results are shown as mean IgG (white bars) or IgA (black bars) IpaB-, IpaD- and dmLT-specific ASCs per 106 cells+SEM from quadruplicate wells.

Figure 27A:
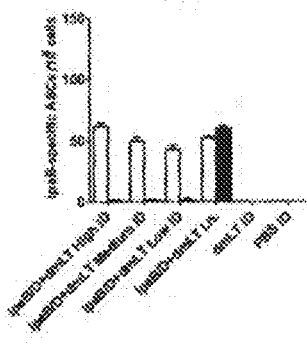
Figure 27B:
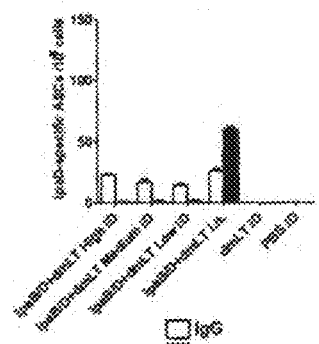
Figure 27C:
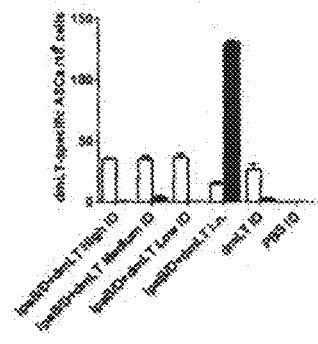
Figure 28A:
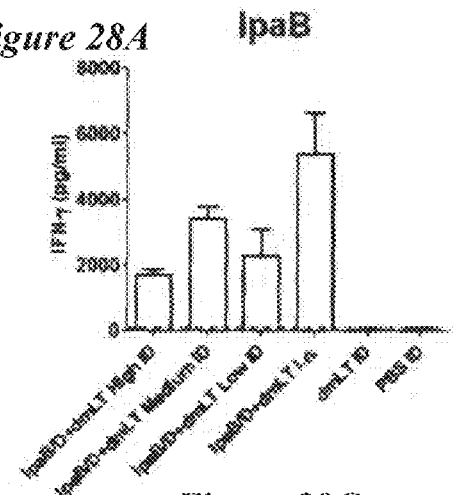
Figure 28B:
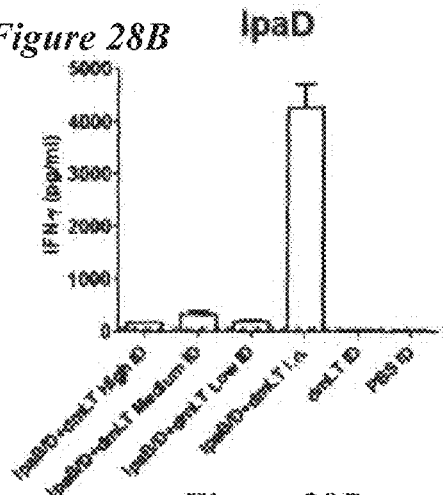
Figure 28C:
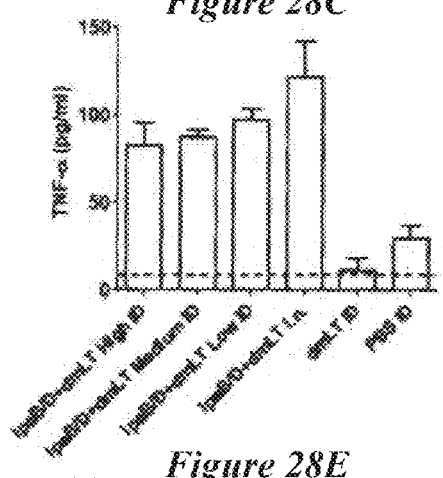
Figure 28D:
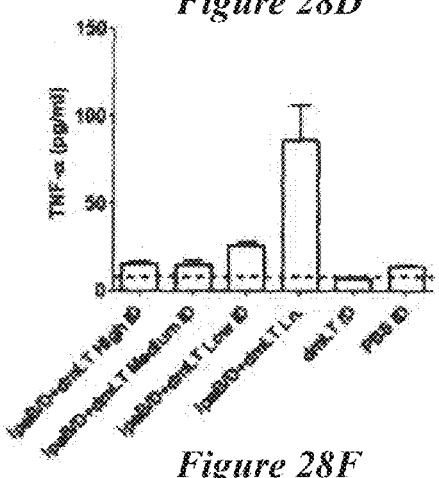
Figure 28E:
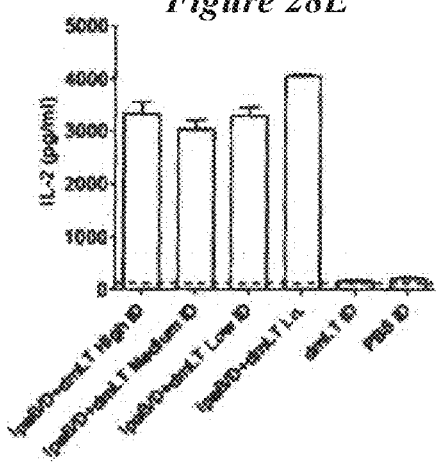
Figure 28F:
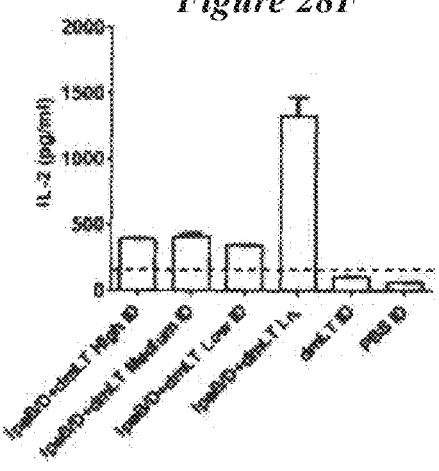
Figure 29A:
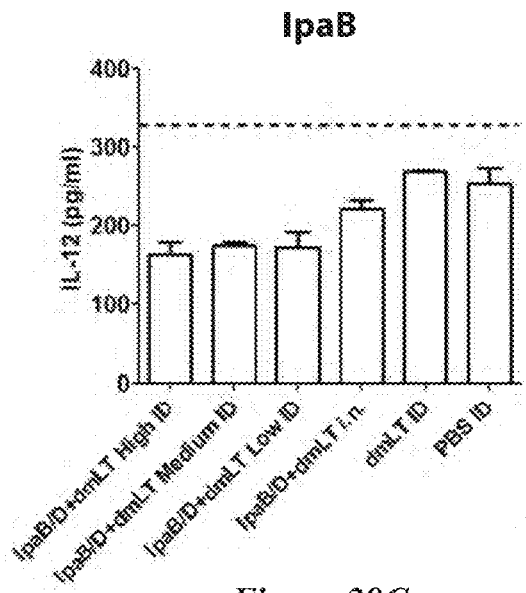
Figure 29B:
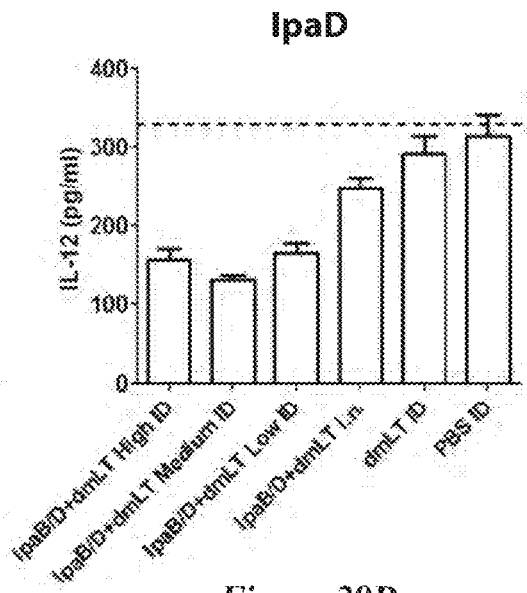
Figure 29C:
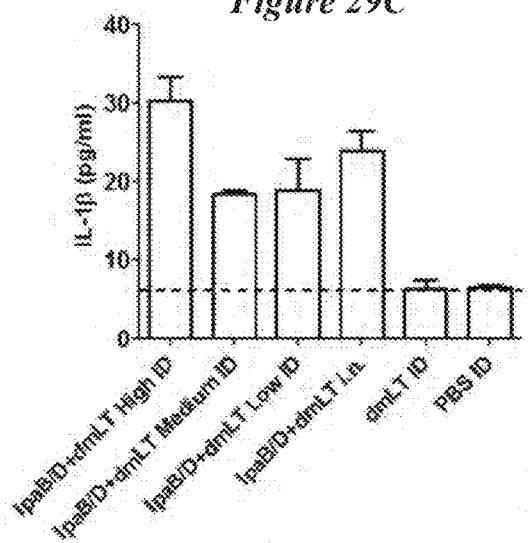
Figure 29D:
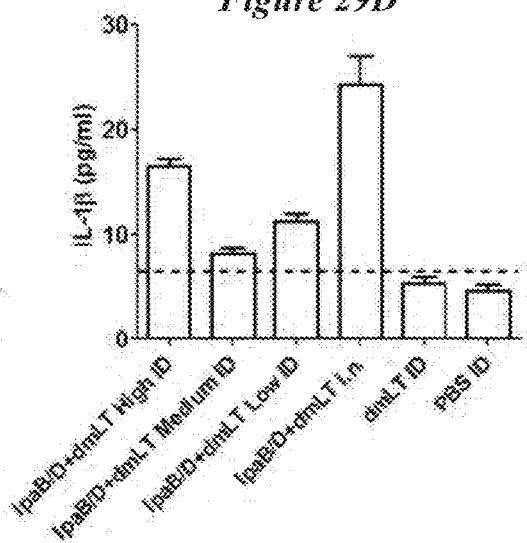

FIG. 27A-C. Bone Marrow A, IpaB-, B, IpaD- and C, dmLT-specific IgG and IgA ASCs. Mice were immunized as described in FIG. 4. BM was collected on day 56 from 5 mice in each group and single cell suspensions prepared. The frequencies of IgA and IgG ASC were measured by ELISpot. Results are shown as mean IgG (white bars) or IgA (black bars) IpaB-, IpaD- and dmLT-specific ASCs per 106 cells+SEM from triplicate wells.

FIG. 28A-F. IpaB and IpaD-specific Th1 cytokine secretion by spleen cells. Mice were immunized as described in Example 4. Spleens were collected on day 56 and single cell suspensions prepared. Cells were incubated for 48 h in the presence of IpaB (A, C, E) and IpaD (B, D, F). Supernatants were tested for the presence of cytokines using a microarray multiplex assay (MSD, Mouse Th1/Th2 9-Plex). Results are shown as mean IFN-γ (A-B), TNF-α (C-D) and IL-2 (E-F) in pg/ml+SEM from triplicate wells. Dashed line represents average baseline secretion by unstimulated cells from all groups.

FIG. 29A-D. IpaB and IpaD-induced pro-inflammatory cytokine production in spleen cells. Mice were immunized as described in FIG. 4. Spleens were obtained from 5 mice in each group on day 56. Single cell suspensions were prepared. Cells were incubated for 48 hours with IpaB (A, C), IpaD (B, D) and supernatants tested for cytokine production as described in FIG. 23, using a multiarray MSD, Mouse Th1/Th2 9-Plex Assay. Results are shown as mean IL-12 (AB) and IL-1β (C-D) in pg/ml+SEM from triplicate wells. Dashed line represents average baseline cytokine secretion by unstimulated cells from all groups.

FIG. 30A-F. IpaB and IpaD induced Th2 and anti-inflammatory cytokine secretion by splenocytes. Mice were immunized as described in FIG. 4. Spleens were obtained from 5 mice in each group on day 56. Single cell suspensions were prepared and cells were incubated for 48 hours with IpaB (A, C), IpaD (B, D). Supernatants were tested for secretion of cytokines using a multiarray MSD sandwich Mouse Th1/Th2 9-Plex Assay. Results are shown as mean IL-10 (A-B), IL-4 (C-D) and IL-5 (E-F) in pg/ml+SEM from triplicate wells. Dashed line represents average baseline cytokine secretion by unstimulated cells from all groups.

Figure 31:
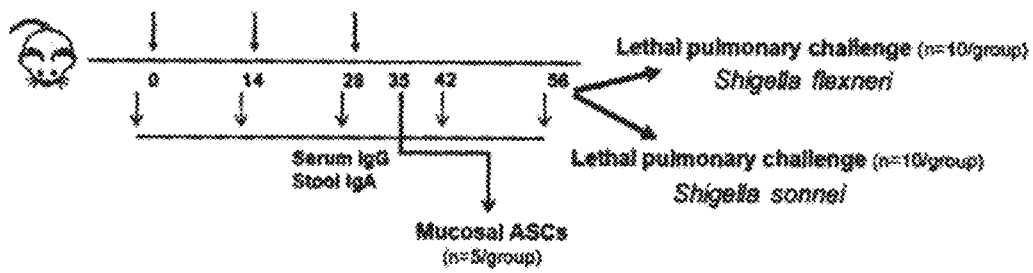

FIG. 31. Schematic of challenge experiment.

FIG. 32A-C. Kinetics of serum A, IpaB-, B, IpaD-, and C, dmLT-specific IgG (Experiment 2). Mice were immunized with IpaB and IpaD, along with dmLT on days 0, 14 and 28 as described above. Serum IgG and stool IgA antibody titers were measured by ELISA. Data represent pool titers from each group.

FIG. 33A-C. A, IpaB-, B, IpaD- and C, dmLT-specific IgG and IgA ASCs in lungs. Mice were immunized as described in FIG. 12. Lungs were collected on day 35 post-primary immunization from 5 mice in each group on day 35 and single cell suspensions prepared. Lymphocytes were separated using Lympholyte density gradient. The frequencies of IgA and IgG ASC were measured by ELISpot. Results are shown as mean IgG (white bars) or IgA (black bars) IpaB-, IpaD- and dmLT-specific ASCs per 106 cells+SEM from triplicate wells (lungs for each group were pooled).

FIG. 34A-C. NALT A, IpaB-, B, IpaD- and C, dmLT-specific IgG and IgA ASCs. Mice were immunized as described in FIG. 23. Nasal tissues were collected on day 35 from 5 mice in each group and single cell suspensions prepared. The frequencies of IgA and IgG ASC were measured by ELISpot. Results are shown as mean IgG (white bars) or IgA (black bars) IpaB-, IpaD- and dmLT-specific ASCs per 106 cells+SEM from triplicate wells.

FIG. 35A-C. Peyer's patches A, IpaB-, B, IpaD- and C, dmLT-specific IgG and IgA ASCs. Mice were immunized as described in FIG. 23. Peyer's patches were collected on day 35 from 5 mice in each group and single cell suspensions prepared. The frequencies of IgG and IgA ASCs were measured by ELISpot. Results are shown as mean IgG (white bars) or IgA (black bars) IpaB-, IpaD- and dmLT-specific ASCs per $10^6$ cells+SEM from triplicate wells.

FIG. 36A-C. Spleen A, IpaB-, B, IpaD- and C, dmLT-specific IgG and IgA ASCs. Mice were immunized as described for FIG. 23. Spleens were collected on day 35 from 5 mice in each group and single cell suspensions prepared. The frequencies of IgA and IgG ASC were measured by ELISpot. Results are shown as mean IgG (white bars) or IgA (black bars) IpaB-, IpaD- and dmLT-specific ASCs per 106 cells+SEM from quadruplicate wells.

FIG. 37A-C. A, IpaB-, B, IpaD- and C, dmLT-specific IgG and IgA in bronchoalveolar lavage (BAL). Mice were immunized as described for FIG. 23. BAL fluid was collected on day 35 from 5 mice in each group and supernatant was removed and stored at −20° C. until analysis. IgG and IgA titers were measured by ELISA. Results are shown as mean IpaB-, IpaD- and dmLT-specific IgG (white bars) or IgA (black bars) titers+SEM.

Figure 38:
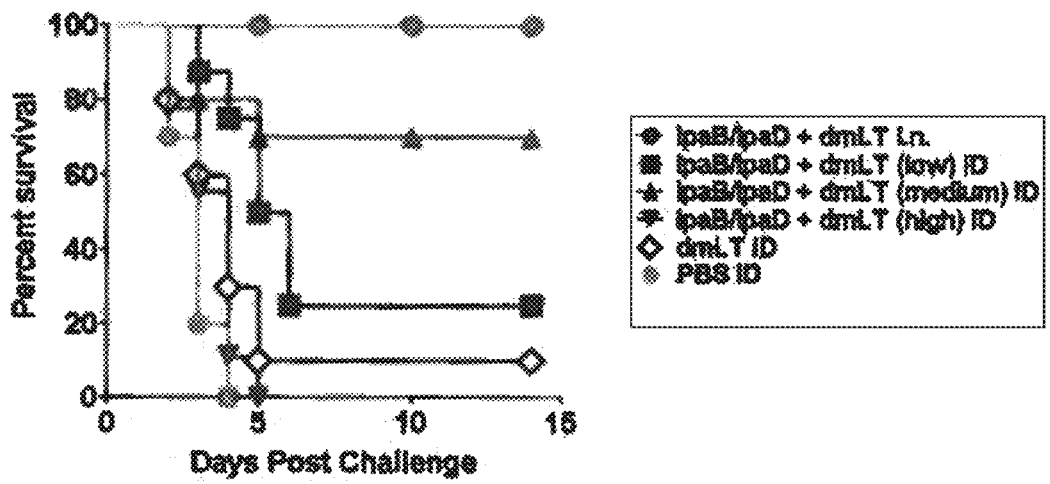

FIG. 38. Protective efficacy against S. flexneri. Mice were immunized i.d. as described above for FIG. 23. Challenge was performed on day 56 after immunization. The animals received $5.8 \times 10^7$ CFU of S. flexneri 2a in 30 μl administered i.n. Challenge was performed under anesthesia. Mice were monitored for 14 days. Health scores and body weight were recorded daily. Data represent survival curves from 10 mice per group.

Figure 39A:
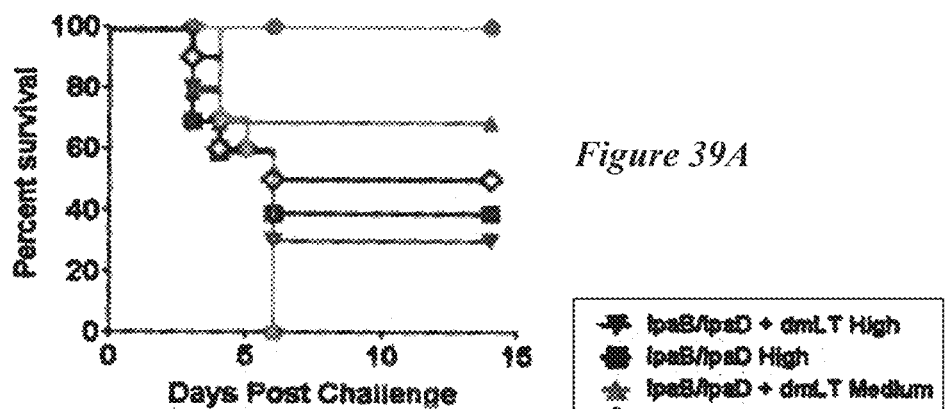
Figure 39B:
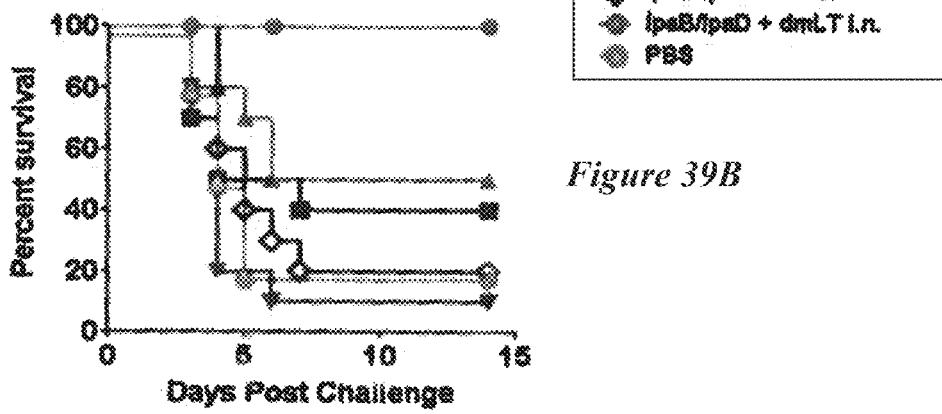

FIGS. 39A and B. Protective efficacy against S. flexneri and S. sonnei. Mice were immunized as described for FIG. 23. Challenge was performed on day 56 after immunization. (A) 10 animals per group received 5.4×107 CFU of S. flexneri 2a and (B) 10 animals per group received $1.35 \times 10^8$ CFU S. sonnei. The organisms were administered in 30 μl via i.n. Mice were monitored for 14 days. Health scores and body weight were recorded on daily basis. Data represent survival curves from 10 mice per group.

Figure 40:
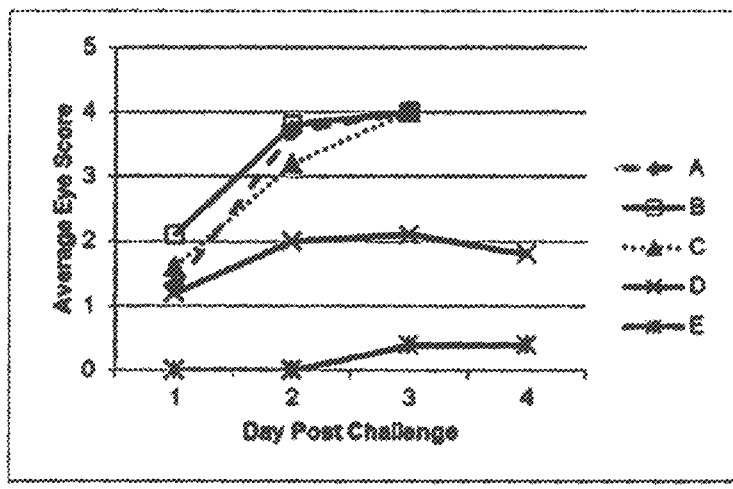

FIG. 40. Progression of disease following challenge with WT S. flexneri 2a 2457T.

Figure 41A:
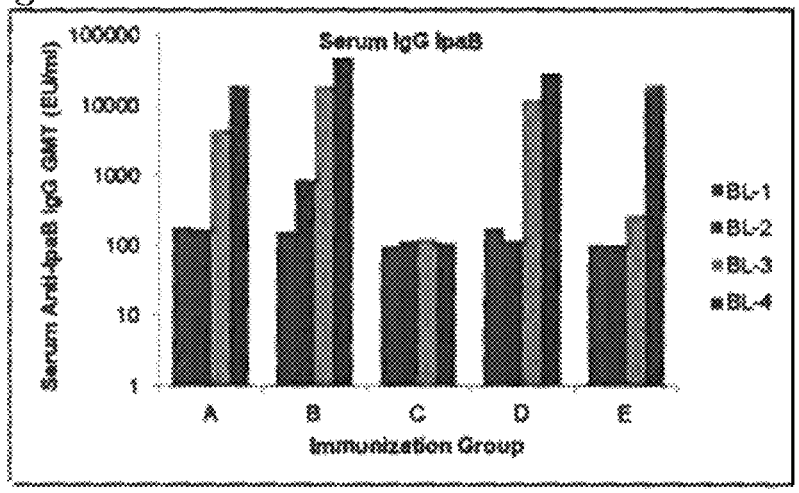
Figure 41B:
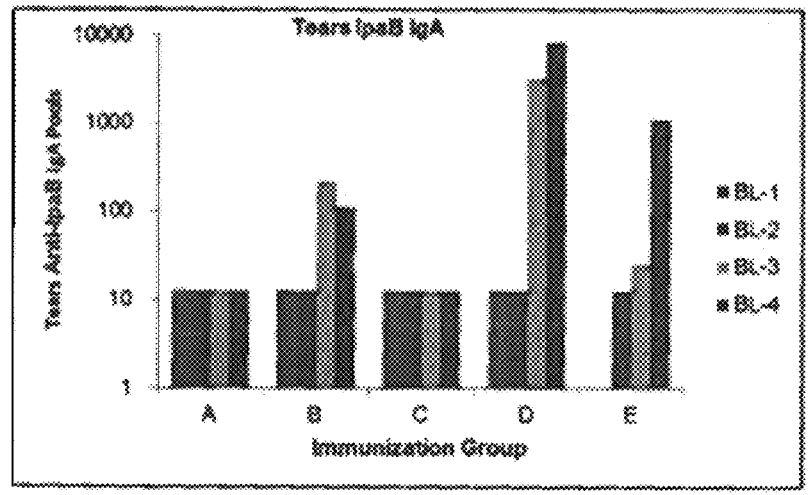

FIGS. 41A and B. Serum and mucosal antibody responses to IpaB. Serum IgG GMTs (A) and mucosal IgA titers in pooled tears (B) are shown for each immunization group for each subsequent collection. BL-1, pre-immune titer; BL-2, post 1 dose; BL-3, post 2 doses; and BL-4, post 3 doses.

Figure 42A:
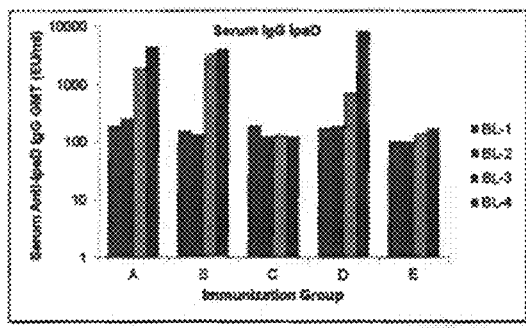
Figure 42B:
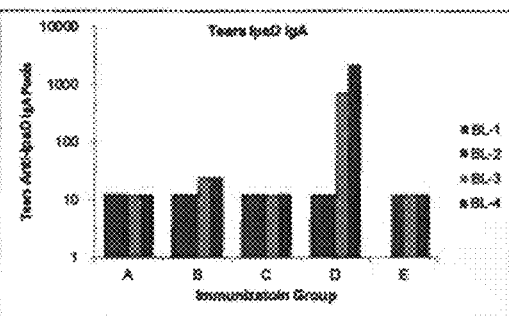

FIGS. 42A and B. Serum and mucosal antibody responses to IpaD. Serum IgG GMTs (A) and mucosal IgA titers in pooled tears (B) are shown for each immunization group for each subsequent collection. BL-1, pre-immune titer; BL-2, post 1 dose; BL-3, post 2 doses; and BL-4, post 3 doses.

Figure 43A:
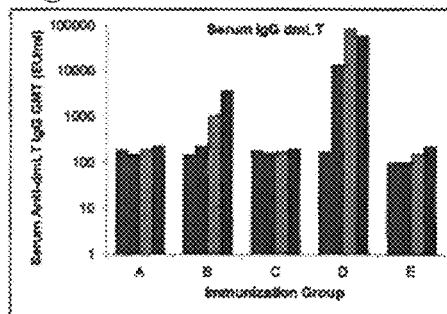
Figure 43B:
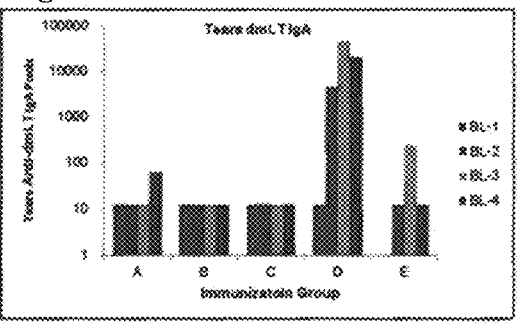

FIGS. 43A and B. Serum and mucosal antibody responses to dmLT. Serum IgG GMTs (A) and mucosal IgA titers in pooled tears (B) are shown for each immunization group for each subsequent collection. BL-1, pre-immune titer; BL-2, post 1 dose; BL-3, post 2 doses; and BL-4, post 3 doses.

Figure 44A:
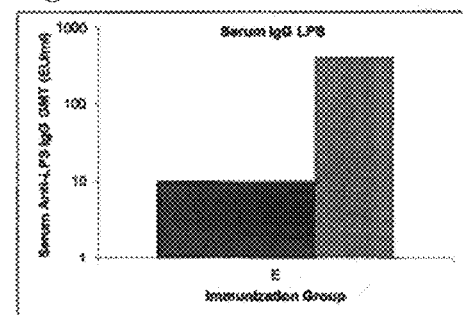
Figure 44B:
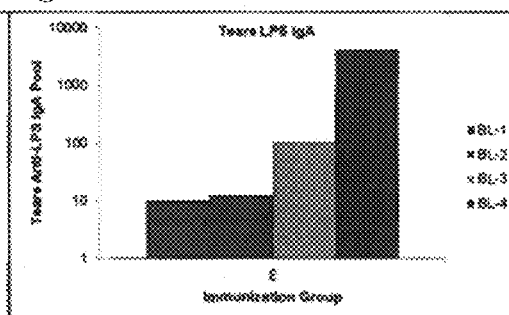

FIGS. 44A and B. Serum and mucosal antibody responses to IpaB. Serum IgG GMTs (A) and mucosal IgA titers in pooled tears (B) are shown for each immunization group for each subsequent collection. BL-1, pre-immune titer; BL-2, post 1 dose; BL-3, post 2 doses; and BL-4, post 3 doses.

Figure 45:
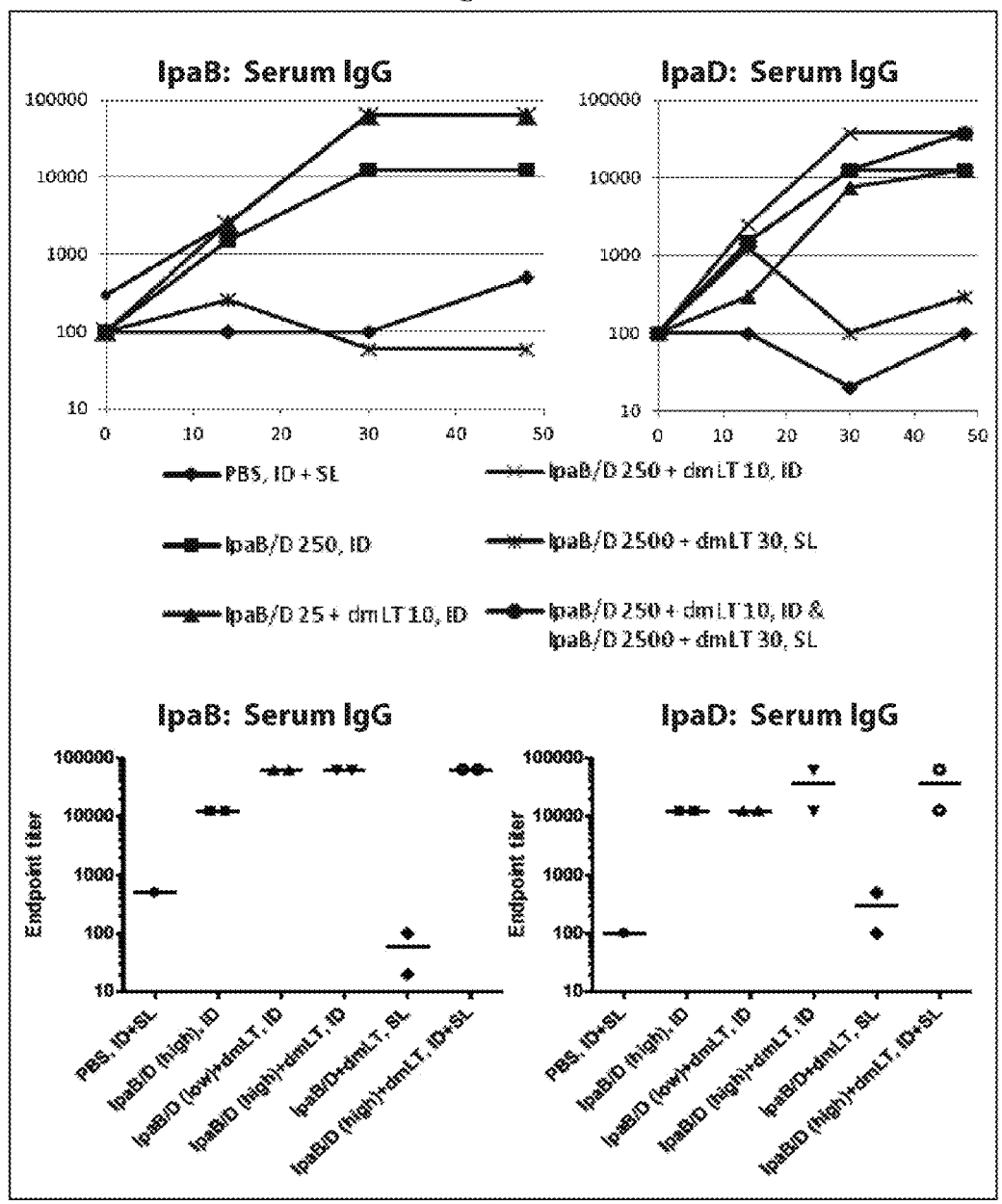

FIG. 45. Serum IgG response of piglets against Ipa vaccine administered IS, SL and ID+SL.

Figure 46:
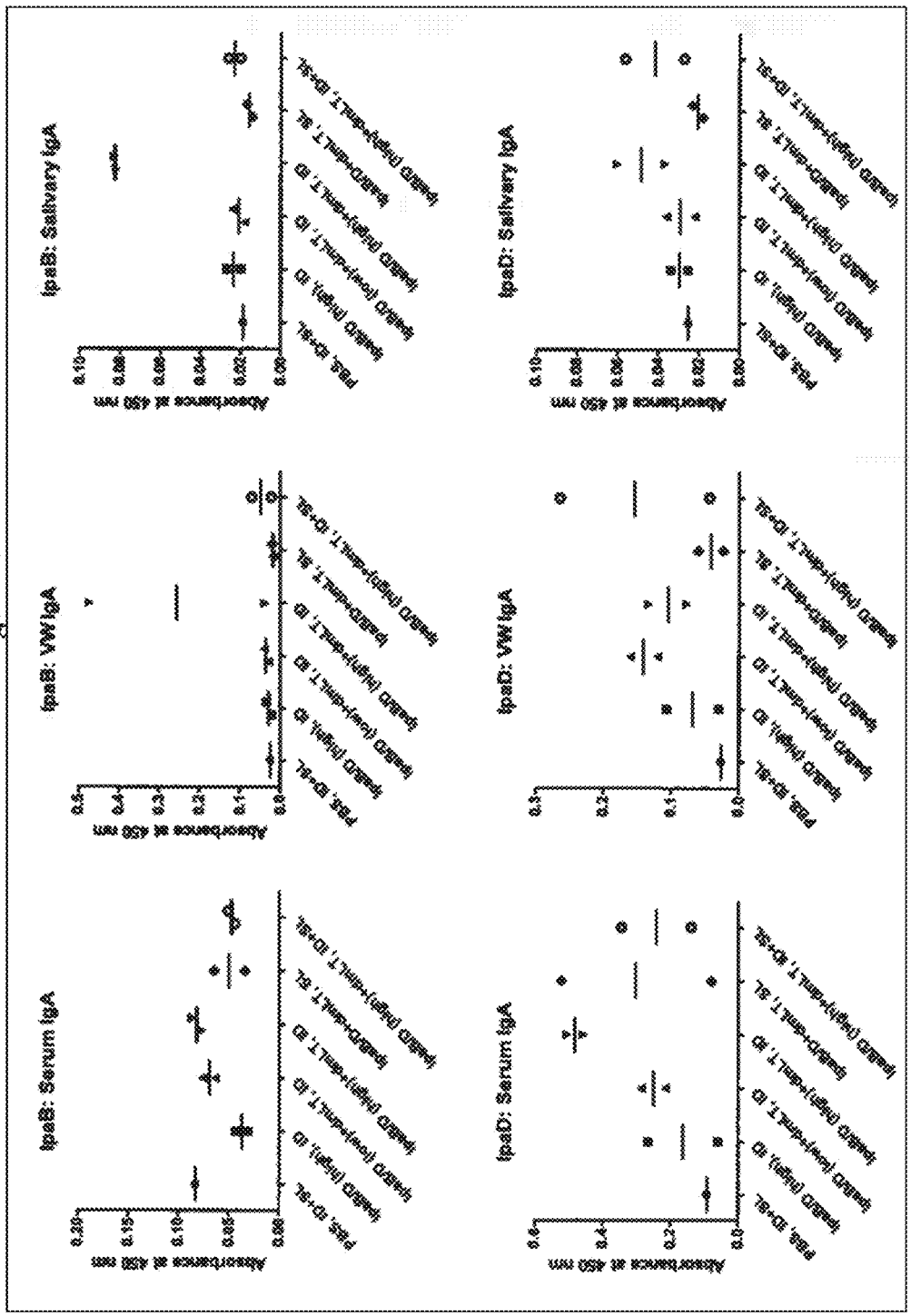

FIG. 46. IgA response of piglets against Ipa vaccine administered IS, SL and IS+SL.

Figure 47A:
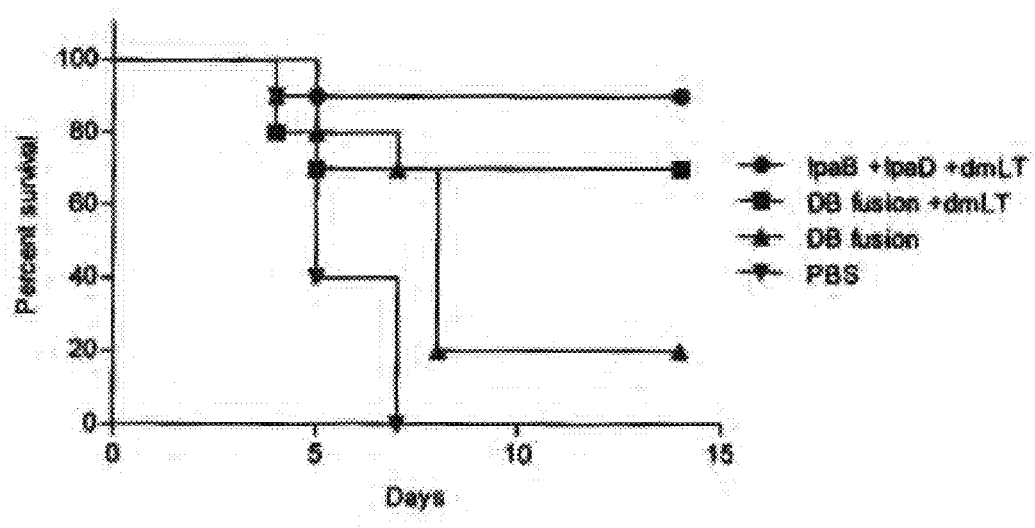

FIGS. 47A and B. Protective efficacy of the DB fusion in mice. A, when challenged with S flexneri; B, when challenged with S sonnei.

DETAILED DESCRIPTION

The immunogenicity of the *Shigella* proteins IpaB, IpaD and IpgC administered alone or combined (e.g. as an IpaB/

IpgC complex), have been shown to provide protective immunity to mammals against the otherwise serious consequences of exposure to and infection by *Shigella*. Significantly, the administration of these proteins afforded protection in an O-independent manner, i.e. protection was not limited to a single O-type. Thus, vaccines formulated from the proteins may be used to protect recipients from disease caused by a broad range of *Shigella* and related organisms. In some embodiments, the proteins are administered together with a mucosal adjuvant such as the double mutant heat-labile toxin (dmLT) from enterotoxigenic *E. coli*.

The proteins which may be used in the practice of the invention include IpaB, IpaD and IpgC, administered alone or in various forms and combinations as described herein. The full length sequences of each of these proteins are provided in FIGS. 12A, B and C, respectively. The phrase(s) IpaB, IpaD and IpgC protein(s) as used herein refer to both the full length proteins as depicted in the figures, and also to antigenic regions thereof. By an "antigenic region" we mean a foreshortened or truncated version or form of the protein which elicits the same or a comparable level of protection as the full length protein from which it is taken, a comparable level being in the range of at least about 50, 55, 60, 65, 70, 75, 80, 85, 90, 95, or even 100% (or more) of the protective activity of the parent, full-length molecule. An antigenic region may be a shorter protein (e.g. containing more than about 250 amino acids), a polypeptide (e.g. containing less than about 250 amino acids but more than about 100 amino acids), or a peptide (e.g. containing less than about 100 amino acids). Those of skill in the art will recognize that the "definitions" of protein, polypeptide and peptide may vary within the art, and may overlap in meaning, and are often used interchangeably.

The proteins, polypeptides or peptides which may be used in the practice of the invention include IpaB, IpaD and IpgC, and variants or derivatives thereof which have about at least about 50, 55, 60, 65, 70, 75, 80, 85, or 90% identity to the sequences presented herein, and preferably the level of identity is at least about 92, 93, 94, 95, 96, 97, 98 or 99%. Those of skill in the art are familiar with methods and software programs for sequence comparison to determine identity.

The invention also encompasses the use of nucleic acids encoding the proteins/polypeptides/peptides described herein, i.e. nucleic acid vaccines are also contemplated. Those of skill in the art are aware of the many protocols for preparing and administering nucleic acid vaccines, such as those described in issued U.S. Pat. Nos. 7,927,870 and 7,094,410, the complete contents of which is hereby incorporated by referenced in entirety.

Those of skill in the art will appreciate that the genetic code is redundant and that many sequences may encode a given amino acid sequence. All nucleic acid sequences (e.g. DNA, RNA, cDNA, DNA/RNA hybrids, etc.) which successfully encode and express the proteins/polypeptides/peptides described herein, in a manner that results in protection of a subject to whom the vaccine is administered, also as described herein, may be used in the practice of the invention. Also encompassed are vectors which contain such nucleic acid sequences (e.g. plasmids, cosmids, various expression vectors, etc.), and host cells such as bacteria, insect cells, etc., which comprise the nucleic acid sequences and/or the vectors. Such vectors typically include one or more expressible gene sequences encoding one or more of the proteins/polypeptides/peptides of interest, which may be a chimera, operably linked to at least one transcription element (e.g. a promoter) that drives expression of the gene.

In some embodiments of the invention, the proteins, polypeptides or peptides that are used in the vaccine are chimeric proteins. By a "chimeric protein" we mean a protein that is translated from a single, contiguous nucleic acid molecule, and which comprises sequences from at least two different proteins or antigenic regions thereof. For example, a chimera of the invention may include two or more of IpaB and/or IpaD and/or IpgC, or antigenic regions of two or more of these. Typically, the individual sequences are joined via a linker or spacer sequence of e.g. from about 2 to about 20 amino acids, usually from about 2 to about 10 amino acids. The amino acids in linking sequences are typically uncharged and the linker sequence usually does not exhibit secondary or tertiary structure, but does allow the fused protein segments to adopt functional secondary, tertiary, etc. conformations.

The present invention provides compositions for use in eliciting an immune response and/or vaccinating an individual against *Shigella*, or against disease symptoms caused by *Shigella* infection, and/or infection by related organisms. The compositions include one or more substantially purified proteins, polypeptides or antigenic regions thereof as described herein, or substantially purified nucleic acid sequences (e.g. DNA cDNA, RNA, etc.) encoding such proteins, polypeptides or antigenic regions thereof, and a pharmacologically suitable carrier. By "substantially purified" we mean that the molecule is largely free of other organic molecules, cellular debris, solvents, etc. when tested using standard techniques known to those of skill in the art (e.g. gel electrophoresis, column chromatography, sequencing, mass spectroscopy, etc.). For example, the molecule is generally at least about 50, 55, 60, 65, 70, or 75% pure, and preferably is at least about 80, 85, 90, 95% or more pure (e.g. 96, 97, 98, 99 or even 100% pure). The preparation of proteins, polypeptides, and peptides as described herein is well-known to those in the art, and includes, for example, recombinant preparation; isolation from a natural source; chemical synthesis; etc. The purification of proteinaceous materials is also known, and new improved methods that are advantageous for the proteins utilized in the practice of the invention are described in the Examples section below.

The preparation of compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared (e.g. lyophilized, freeze-dried forms, etc.). The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of protein, polypeptide or peptide (or encoding nucleic acids) in the formulations may vary. However, in general, the amount in the formulations will be from about 1 to about 99%.

In addition, the composition may contain adjuvants, many of which are known in the art. For example, adjuvants suitable for use in the invention include but are not limited to: bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 de-O-acylated monophosphoryl lipid A. Other non-toxic LPS derivatives include monophosphoryl lipid A mimics, such as aminoalkyl glucosaminide phosphate derivatives e.g. RC-529. Lipid A derivatives include derivatives of lipid A from *Escherichia coli* such as OM-174. Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly (dG) sequences have also been shown to be immunostimulatory. The CpG's can include nucleotide modifications/analogs such as phosphorothioate modifications and can be double-stranded or single-stranded. e.g. replacement of guanosine with 2'-deoxy-7-deazaguanosine. The CpG sequence may include, for example, the motif GTCGTT or TTCGTT. The CpG sequence may be specific for inducing a Th1 immune response, such as a CpG-A ODN, or it may be more specific for inducing a B cell response, such a CpG-B ODN. CpG-A and CpG-B ODNs. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers".

Bacterial ADP-ribosylating toxins and detoxified derivatives thereof may be used as adjuvants in the invention. Preferably, the protein is derived from *E. coli* (e.g. *E. coli* heat labile enterotoxin "LT"), cholera ("CT"), or pertussis ("PT"). The use of detoxified ADP-ribosylating toxins as mucosal adjuvants and as parenteral adjuvants are known. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, is known. Such adjuvants are described, for example, in issued U.S. Pat. No. 8,039,007 (the complete contents of which is hereby incorporated by reference in entirety). Various interleukins may also be used as adjuvants to increase the immune response in a subject. In preferred embodiments, the adjuvant is a mucosal adjuvant such as, for example, the double mutant heat-labile toxin (dmLT) from enterotoxigenic *E. coli*.

The vaccine compositions (preparations) of the present invention may be administered by any of the many suitable means which are well known to those of skill in the art, including but not limited to by injection, inhalation, orally, intranasally, topically, etc. In preferred embodiments, the mode of administration is intranasal. In addition, the compositions may be administered in conjunction with or in a composition which contains other antigens of interest. In other words, they may be administered as a component of a multivalent vaccine which also contains antigens against other related or non-related infectious diseases, especially childhood diseases, such as polio, whooping cough, tetanus, diphtheria, etc.

Recipients of the vaccine of the invention are generally mammals, frequently humans, but this need not always be the case. Veterinary applications are also contemplated. The vaccine are often administered as or together with so-called "child hood" vaccines. Thus, the recipients are preferably human children who may be infants (e.g. up to about 1 hear of age), toddlers (e.g. up to about 2 years of age), or older, and administration may be carried out as a series of initial inoculations followed by booster doses at suitable intervals, e.g. monthly, or every 6-months, or yearly, etc. as necessary to provide protection. Thereafter, or in the case of adults who have not previously been vaccinated, the vaccines may be administered as necessary to result in a protective immune response, and subjects may be re-boosted e.g. about every 10 years throughout adult life.

Vaccine recipients may have never been exposed to *Shigella*, or may have been exposed or suspected of having been exposed but be asymptomatic, or may have actual symptoms of shigellosis, and still benefit from administration of the vaccine. Vaccine administration may prevent disease symptoms entirely, or may lessen or decrease disease symptoms, the latter outcome being, while not being ideal, still better than experiencing full-blown disease symptoms.

The amount of protein that is administered per dose of vaccine is typically in the range of from about 1 to about 1000 µg/kg, and is usually in the range of from about 0.02 to about 20 µg/kg of body weight of the recipient. Those of skill in the art will recognize that the precise dosage may vary from situation to situation and from patient to patient, depending on e.g. age, gender, overall health, various genetic factors, and other variables known to those of skill in the art. Dosages are typically determined e.g. in the course of animal and/or human clinical trials as conducted by skilled medical personnel, e.g. physicians.

The vaccines and immunogenic compositions of the invention may be used to provide immune protection against various *Shigella* species in an O-independent manner, examples of which include but are not limited to: *S. flexneri, S. sonnei, Shigella dysenteriae*, and *Shigella boydii*.

In addition, the compositions may be used to vaccinate or elicit and immune response in subject against disease causing pathogens that are related to *Shigella*, examples of which include but are not limited to enteroinvasive *E. coli* and *Salmonella enterica* serovars *Typhi, Paratyphi* A & B, *Typhimurium* and *Enteritidis*.

Administration of the compositions of the invention results in the production of a protective immune response in subjects who receive the compositions, frequently by the elicitation of antibody production against the administered antigens. Such antibodies are also encompassed by the invention, for example, those generated using laboratory techniques in experimental animals, or using cell culture, or by chemical syntheses, etc. Such antibodies may be polyclonal or monoclonal, and may be specific for the antigens (reacting with no other antigens) or selective for the antigens (reacting more strongly or preferably with the antigens, compared to other antigens). The antibodies may be multivalent. The antibodies may be used for research and/or diagnostic purposes, or alternatively, for treatment, especially of individuals who are infected with *Shigella*.

The invention provides methods of vaccinating, or, alternatively, of eliciting an immune response, in a subject in need thereof. The method generally involves identifying a suitable subject, and administering the composition as described herein. The method may also encompass follow-up of administration, e.g. by assessing the production of protective antibodies by the subject, or the presence (or lack thereof) of disease symptoms, etc. The immune response that is elicited may be of any type, i.e. any type of antibody may be produced in response to administration, and cell-mediated immunity may also be elicited.

The foregoing Examples serve to illustrate exemplary aspects of the invention, but should not be interpreted as limiting in any way.

EXAMPLES

Example 1

A Cross-Protective TTSA-Protein Shigella Vaccine

Shigella ssp. are food and water-borne pathogens that cause severe diarrheal and dysenteric disease associated with high morbidity and mortality. Individuals most often affected are children under 5 years of age in the developing world. The existence of multiple Shigella serotypes and the heterogenic distribution of pathogenic strains as well as emerging antibiotic resistance require the development of a broadly protective vaccine. All Shigella ssp. utilize a type III secretion system (TTSS) to initiate infection. The type III secretion apparatus (TTSA) is the molecular needle and syringe that forms the energized conduit between the bacterial cytoplasm and the host cell to transport effector proteins that manipulate cellular processes to benefit the pathogen. IpaB and IpaD form a tip complex atop the TTSA needle and are required for pathogenesis. Because they are common to all virulent Shigella, they are ideal candidate antigens for a subunit-based, broad-spectrum vaccine. We examined the immunogenicity and protective efficacy of IpaB and IpaD, alone or combined, co-administered with a double mutant heat-labile toxin (dmLT) from E. coli as a mucosal adjuvant in a mouse model of intranasal immunization and pulmonary challenge. Robust systemic and mucosal antibody and T cell-mediated immunity were induced against both proteins, particularly IpaB. Mice immunized with IpaB alone or combined with IpaD, in the presence of dmLT, were fully protected against lethal pulmonary infection with S. flexneri and S. sonnei. We show that Shigella TTSA IpaB and IpaD are promising antigens for the development of a cross-protective Shigella vaccines.
Materials and Methods Protein purification materials. Plasmids and competent E. coli were obtained from Novagen (Madison, Wis.). Metal affinity columns, Q-Sephadex, Butyl Sepharose and HiLoad 16/60 Superdex 200 preparative grade columns were obtained from GE Healthcare (Piscataway, N.J.). n-octyl-polyoxyethylene (OPOE) was obtained from Alexis Biochemicals (Lausen, Switzerland). All other chemicals were reagent grade.

The gene encoding IpaD was copied by PCR from the virulence plasmid of Shigella flexneri 2457T (accession number J04117). The PCR fragment was digested with the restriction enzymes NdeI and BamHI and ligated into NdeI/BamHI digested pET15b from Novagen. The ligation product was used to transform NovaBlue E. coli. Transformants were screened for the proper insert and subjected to double stranded sequencing. A plasmid containing the correct sequence was transformed into BL21 (DE3) E. coli (Novagen). This strain was used to inoculate LB media containing ampicillin. The bacteria were grown to an absorbance at 600 of about 0.6 at which time they were induced to over express IpaD with Isopropyl-β-D-thio-galactoside (IPTG). The bacteria were grown an additional three hours to allow protein expression to occur. Alternatively, a starter culture of 100 ml was used to inoculate a 5- or 10-liter fermentor vessel containing TB media. After growing overnight (16 hours), the bacteria were induced and allowed to express protein for three hours. The bacteria were collected by centrifugation, resuspended in binding buffer (see below for recipe), and lysed by microfluidization. This suspension was clarified by centrifugation and was loaded onto a nickel charged immobilized metal affinity column (IMAC). The column (5 ml) was washed with 10 bed volumes each of binding and wash buffers and then subjected to a gradient of 0% to 40% elution buffer. Peak fractions were combined, buffer exchanged into 10 mM Tris-HCl pH 7.5, 10 mM NaCl and loaded onto a Q-Sephadex anion exchange column (5 ml). The IpaD was eluted via a gradient from 0-16% 1M NaCl in 10 mM Tris pH 7.5 over 15 column volumes. The peak fractions were combined and dialyzed against PBS. Pure protein was stored at −80° C.

The gene encoding IpaB was copied by PCR from the virulence plasmid of Shigella flexneri 2457T (accession number J04117). The PCR fragment was digested with the restriction enzymes NdeI and BamHI and ligated into NdeI/BamHI digested pET15b from Novagen. The ligation product was used to transform NovaBlue E. coli. Transformants were screened for the proper insert and subjected to double stranded sequencing. The gene encoding IpgC was copied by PCR from the virulence plasmid of Shigella flexneri 2457T (accession number J04117). The PCR fragment was digested with the restriction enzymes NdeI and XhoI and ligated into NdeI/XhoI digested pACYCDuet-1 from Novagen. The ligation product was used to transform NovaBlue E. coli. Transformants were screened for the proper insert and subjected to double stranded sequencing. A plasmid containing the correct sequence for IpaB and a plasmid containing the correct sequence for IpgC were transformed into Tuner (DE3) E. coli (Novagen). This strain was used to inoculate LB media containing ampicillin and chloramphenicol. The bacteria were grown to an absorbance at 600 of about 0.6 at which time they were induced to over express IpaB/IpgC with Isopropyl-β-D-thio-galactoside (IPTG). The bacteria were grown an additional three hours to allow protein expression to occur. Alternatively, a starter culture of 100 ml was used to inoculate a 5- or 10-liter fermentor vessel containing TB media. After growing overnight (16 hours), the bacteria were induced and allowed to express protein for three hours. The bacteria were collected by centrifugation, resuspended in binding buffer (see below for recipe), and lysed by microfluidization. This suspension was clarified by centrifugation and was loaded onto a nickel charged immobilized metal affinity column (IMAC). The column (5 ml) was washed with 10 bed volumes each of binding and wash buffers and then subjected to a gradient of 0% to 40% elution buffer. Peak fractions were collected, the buffer exchanged into 1M ammonium sulfate in 50 mM sodium phosphate pH 7.0 and loaded onto a Butyl Sepharose High Performance column (5 ml) with a linear gradient from 1M ammonium sulfate in 50 mM sodium phosphate pH 7.0 to 50 mM sodium phosphate. For preparation of His-tag IpaB, the IMAC-bound protein complex was incubated overnight in the presence of 1% OPOE. The chaperone was removed in the flow through and subsequent wash steps. His-tag IpaB was eluted in the presence of OPOE to maintain the protein in a soluble form. His-tag IpaB was then further purified using size exclusion chromatography using a HiLoad 16/60 Superdex 200 Prep Grade column. All proteins were concentrated by ultrafiltration and dialyzed into PBS pH 7.2. Protein concentrations were determined via absorbance at 280 nm using extinction coefficients based on the amino acid composition of each protein.

Buffers that were utilized are listed below:

4× Charge Buffer: 500 ml

| 200 mM NiSO$_4$ | 52.56 g | 1X = 50 mM |
|---|---|---|

8× Binding Buffer: 1Liter

| 40 mM Imidazole | 2.72 g | 1X = 5 mM |
|---|---|---|
| 4M NaCl | 237 g | 500 mM |
| 160 mM Tris | 19.36 | 20 mM |

Mix together and pH to 7.9 with HCl

8× Wash Buffer: 500 mL

| 480 mM Imidazole | 16.3 g | 1X = 60 mM |
|---|---|---|
| 4M NaCl | 117 g | 500 mM |
| 160 mM Tris | 19.68 | 20 mM |

Mix together and pH to 7.9 with HCl
IF USING UREA drop the imidazole to 20 mM . . . 8X = 160

4× Elution Buffer: 500 mL

| 4M Imidazole | 136 g | 1X = 1M |
|---|---|---|
| 2M NaCl | 58.44 | .5M |
| 80 mM Tris | 4.84 | 20 mM |

Mix together and pH to 7.9 with HCl

4× Strip Buffer: 500 mL

| 0.4M EDTA | 74.4 g | 1X = 100 mM |
|---|---|---|
| 2MNaCl | 58.44 | 500 mM |
| 80 mM Tris | 4.84 | 20 mM |

Mix together. Add NaOH pellets to get pH to 8.0 so that EDTA will dissolve. Then adjust pH to 7.9.

Far-UV circular dichroism (CD) spectra were collected using a Jasco J815 spectropolarimeter equipped with a Peltier temperature controller (Jasco Inc., Easton, Md.). Spectra were acquired using a 0.1 cm path length cuvette at 10° C. A resolution of 1.0 nm and a scanning speed of 50 nm/min with a 2-s data integration time were employed. Spectra presented are an average of three consecutive measurements. The thermal unfolding of the proteins was followed by monitoring the ellipticity at 222 nm over a temperature range of 10 to 90° C. with a resolution of 2.5° C. and 15° C./h heating rate. Protein concentration was 0.5 mg/mL for IpaD and 0.3 mg/ml for IpaB and IpaB/IpgC. CD signals were converted to mean residue molar ellipticities $[\theta]_R$ and the thermal transitions were analyzed using the Jasco Spectral Manager™ and Microcal Origin™ 6.0 software.

Challenge Organisms. *S. flexneri* 2a 2457T and *S. sonnei* 53G inocula for challenge were prepared as previously described. Briefly, the strains were grown on tryptic soy agar (TSA) with Congo Red (final concentration 0.02%); 20-25 colonies were picked and grown in a volume of 125 ml Luria-Bertani (LB) broth (Athena Environmental Sciences, Baltimore, Md.) with agitation for 3-4 hours at 37° C. or until an $Abs_{600}$ of 0.8-1.3 was achieved. Cultures were centrifuged and bacterial pellets were resuspended in phosphate buffered saline (PBS). Colony-forming units (CFU) of each challenge dose were determined by plating serial dilutions of the culture on Congo Red agar plates. The mouse lethal dose 50% ($MLD_{50}$) for the challenge strains were calculated by the method of Reed and Muench and determined to be ~5.4×10$^6$ CFU for *S. flexneri* and 1.2×10$^7$ CFU for *S. sonnei*.

Mice, Immunizations and Challenge Procedures. Female Balb/c mice (8-10 week old, Charles River Laboratories, Wilmington, Mass.) were immunized intranasally (i.n.) on days 0, 14 and 28 with IpaB (2.5 µg), IpaB complexed with IpgC (3.25 µg; equivalent to 0.75 µg IpgC and 2.5 µg IpaB) or IpaD (10 µg). The proteins were administered alone or combined, admixed with 2.5 µg of the *E. coli* dmLT adjuvant. Control groups received 2.5 µg of dmLT or PBS. Immunization was performed under Isoflurane anesthesia (Abbott Laboratories, North Chicago, Ill.) dispensed through a precision vaporizer. The inoculum volume was 25 µl and it was administered by means of a pipette and tip, delivering half of the volume in each nare. Animals were allowed to completely recover before they were returned to their cages, and they were monitored daily after immunization. On day 56 after primary immunization, mice were challenged with virulent *Shigella* strains via the nasal route to induce a pulmonary infection, as previously described. Two lethal dosage levels were used for both *S. flexneri* (6×10$^7$ and 1.3×10$^8$ CFU), corresponding to 11 and 24 MLD50, and *S. sonnei* (1.1×10$^8$ and 2×10$^8$ CFU), corresponding to 5 and 9 MLD50, respectively. The challenge inoculum was given in a volume of 30 µl PBS. Mice were monitored daily for 14 days after the challenge, and their health status, daily weight and survival were recorded. Mice were euthanized if they reached the moribund state or lost more than 20% of their initial body weight and did not recover within 48 h. Animal studies and procedures were approved by the University of Maryland Institutional Animal Care and Use Committee.

Measurement of Antibodies. Serum IgG antibodies to IpaB, IpaD and dmLT were measured by enzyme-linked immunosorbent assay (ELISA). Briefly, Immulon II ELISA plates (Thermo Scientific, Waltham, Mass.) were coated with IpaB (0.1 µg/ml), IpaD (1 µg/ml) or dmLT (1 µg/ml) diluted in PBS, for 3 h at 37° C. Plates were washed with PBS Tween (PBST) and blocked overnight with PBS containing 10% dry milk (Nestle, Solon, Ohio). Serum samples were added in serial dilutions in PBST 10% dry milk and incubated for 1 h at 37° C. Antibodies were detected with horseradish peroxidase (HRP)-labeled goat anti-mouse IgG followed by TMB substrate (KPL, Gaithersburg, Md.). The reaction was stopped by adding 1M H3PO4. Plates were read using an Ascent microplate reader (Thermo Scientific, Waltham, Mass.). Titers were calculated by interpolation of Abs values of experimental samples in the regression curve of a calibrated positive control; they are reported in ELISA Units (EU) per ml and correspond to the inverse of the serum dilution that produces an $Abs_{450}$ of 0.2 above the blank. For measurement of stool antibodies, 5-6 fecal pellets from individual animals were weighted and resuspended 10% W/V in PBS containing 0.2% sodium azide (Sigma-Aldrich, St Louis, Mo.). Samples were centrifuged and supernatants stored at −20° C. with 1 mM phenylmethylsulfonyl fluoride (PMSF) (Sigma-Aldrich). IgA antibodies to IpaB, IpaD and dmLT were measured in stool supernatants by ELISA, as described above, using HRP-labeled goat anti-mouse IgA as the secondary antibody (SouthernBiotech, Birmingham, Ala.).

Antibody Secreting Cells (ASC). The frequency of IgG- and IgA-secreting cells was measured by ELISpot as previously described, with modifications. Spleen, bone marrow and nasal associated lymphoid tissue (NALT) were collected on day 39 and 56 after immunization and single cell suspensions were prepared. Cells were incubated overnight in Immulon II flat bottom plates (Thermo Scientific) previously coated with 5 μg/ml IpaB or IpaD; PBS-coated wells were used as negative controls. HRP-labeled goat anti-mouse IgG (KPL) and IgA (SouthernBiotech) were added in agarose overlay. True Blue (KPL) was used as substrate. For all ELISpot measurements, spots were counted using a stereomicroscope and results were expressed as mean spot-forming cells (SFC) per $10^6$ cells from quadruplicate wells.

IFN-γ Secretion. The frequencies of IFN-γ-secreting T cells were measured as previously described. Spleens were collected on day 56 following primary immunization and single cell suspensions were prepared. Cells (in quadruplicate wells) were incubated with IpaB or IpaD (10 μg/ml) in plates previously coated with anti-IFN-γ capture antibody (IFN-γ ELISpot kit, BD Biosciences, San Diego, Calif.) for 48 h at 37° C., 5% $CO_2$. IFN-γ production was detected using a biotinylated anti-IFN-γ antibody, followed by Streptavidin-HRP. 3-Amino-9-ethylcarbazole was used as a peroxidase substrate (Calbiochem, San Diego, Calif.). SFC were calculated and reported as described above.

Statistical Methods. All graphics and statistical analysis were generated using GraphPad Prism 5. Data distribution was first examined using the D'Agostino & Pearson normality test. One-way ANOVA and Tukey's tests were used for subsequent group comparisons. Survival curves were plotted in Kaplan-Meier curves; treatments were compared using a log rank test. A $P<0.05$ was considered significant in all analyses.

Results

Purification of Recombinant *Shigella* IpaB and IpaD. Purification of recombinant IpaD and IpaB was performed by modification to previous methods. In addition to the standard IMAC purification, contaminating proteins were removed from the His-tag IpaD via anion exchange chromatography (FIG. 1). The association of IpaB with its cognate chaperone, IpgC, is required for IpaB stability in the *Shigella* cytoplasm. Thus, we previously purified the overexpressed IpaB/IpgC complex via a His-tag genetically fused to the N-terminus of IpgC. To more efficiently capture IpaB, the plasmid constructs were modified to fuse the His-tag to the N-terminus of IpaB, leaving the IpgC untagged. After standard IMAC purification, the complex was further purified via hydrophobic interaction chromatography (FIG. 1). When His-tag IpaB alone was required, the His-tag IpaB/IpgC complex bound to the IMAC resin was incubated with 1% OPOE. IpgC was washed away and the His-tag IpaB eluted with buffer containing OPOE. His-tag IpaB was further purified by size exclusion chromatography (FIG. 1).

Figure 2A:
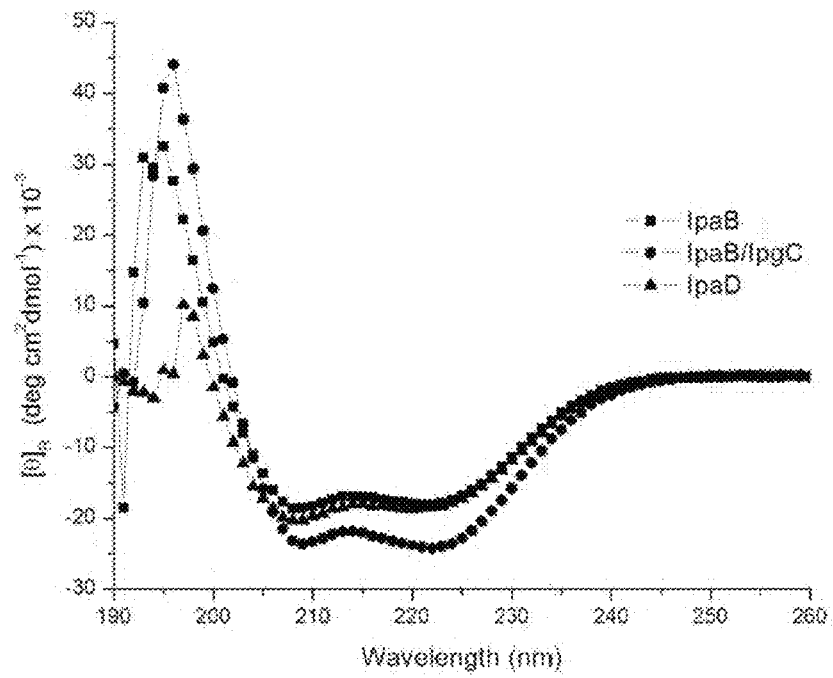
Figure 2B:
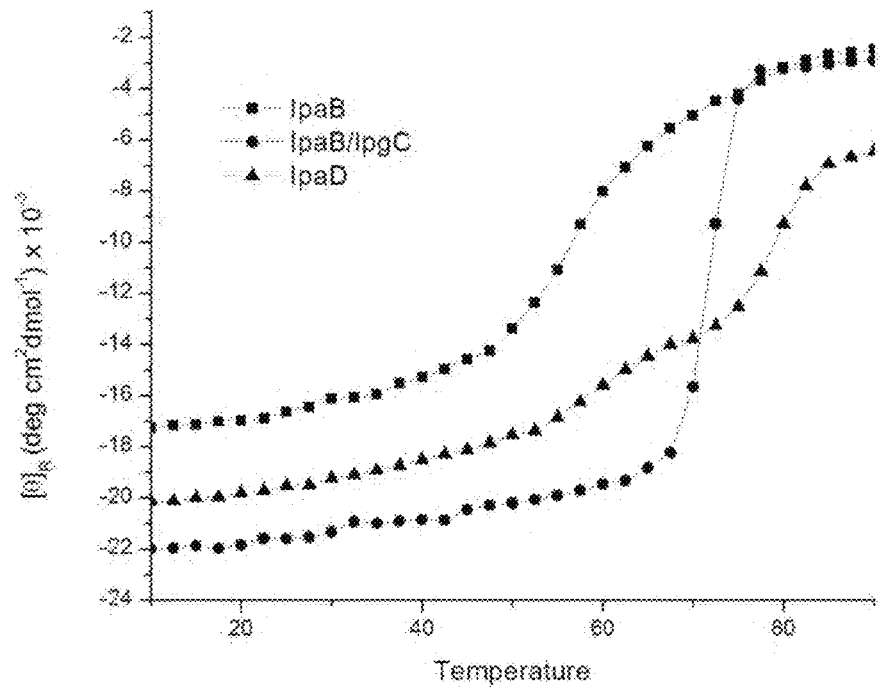

Far-UV CD was employed to assess the secondary structure of the purified proteins. These spectra are routinely collected to ensure the purification process has resulted in proteins maintaining their proper conformation. Thus, CD was used to demonstrate that the proteins were unaffected by the additional purification steps. Indeed, the spectra for IpaD, IpaB and the IpaB/IpgC complex exhibit the typical α-helical minima at 208 and 222 nm (FIG. 2A). While additional purification steps have been added to remove contaminants, these spectra illustrate that the contaminants have not contributed significantly to previous measurements. To assess the stability of the purified recombinant proteins, thermal unfolding curves were collected. As previously reported, IpaD exhibited an initial transition at 60° C. and a second transition at 80° C. in which the protein completely unfolds and precipitates (FIG. 2B). When the IpaB and IpaB/IpgC thermal unfolding curves were obtained, only one transition was seen regardless of the presence of the chaperone (FIG. 2B). Although preliminary results have indicated that IpaB forms a multimeric complex, the IpgC still acts to stabilize IpaB, which is demonstrated by the increase in the thermal unfolding from 60° C. for IpaB to 70° C. for IpaB/IpgC.

To determine the initial stability of the proteins under standard storage conditions, IpaD, IpaB and IpaB/IpgC in PBS were stored at 4° C. or −80° C. and assessed for degradation weekly, for a three-month period, using SDS-PAGE. IpaD remained stable for up to three months regardless of temperature (data not shown). Both IpaB and IpaB/IpgC were stable for three months at −80° C. In contrast, IpaB and IpaB/IpgC were stable for only three and four weeks at 4° C., respectively. In light of the thermal stability described above, it was surprising that the IpaB/IpgC complex degraded 25% faster than IpaB alone at 4° C., albeit only one week. While these data appear contradictory to the thermal unfolding where the complex was more stable, it is likely that binding of IpgC to IpaB results in unstructured regions that are unique to the complex and are available to proteolytic cleavage.

Mucosal immunization with IpaB/D proteins elicits strong antibody responses. The kinetics of serum IgG responses against *Shigella* IpaB and IpaD and the *E. coli* dmLT adjuvant are shown in FIG. 3. Mice immunized i.n. with the Ipa proteins alone (i.e. IpaB, the IpaB/IpgC complex, and IpaD) or combined (i.e. IpaB+IpaD or IpaB/IpgC+IpaD), in the presence of dmLT, developed robust antigen-specific antibody responses. Serum IgG antibodies to IpaB were detected soon after immunization, i.e., 2 weeks after the first vaccine dose, whereas antibodies against IpaD appeared later, i.e., 2 weeks after the second immunization. For both IpaB and IpaD, serum IgG levels reached a plateau after the third immunization. No differences were seen in the serum IgG responses to either of the vaccine antigens among the different groups regardless of whether the Ipa proteins, admixed with dmLT, were administered alone (IpaB, IpaB/IpgC or IpaD) or combined (IpaB+IpaD and IpaB/IpgC+IpaD). Interestingly, despite the fact that the amount of IpaB used for immunization was a fraction (1:4) of the amount of IpaD (2.5 μg vs. 10 μg), the antibody responses to IpaB consistently surpassed the responses induced by IpaD in at least 1 log, at all time points examined ($p<0.05$), and in all the experiments performed. The amount of IpaB and IpaD used for immunization was established in preliminary dosing experiments in which increasing quantities of either protein (2.5 μg to 20 μg) were administered with dmLT. Increasing amounts of dmLT were also tested. We selected the 1:4 dose ratio (2.5 μg of IpaB and 10 μg of IpaD) and 2.5 μg of dmLT for subsequent experiments because when combined in such proportion, the proteins were well tolerated and reached the highest responses within the variables tested. The IpaB/IpgC complex was not included in dose-finding studies, but was used in the same amount as IpaB.

Very strong serum IgG responses were also produced against the adjuvant *E. coli* dmLT. Elevated titers were detected 2 weeks after vaccination and reached a plateau 2 weeks after the second dose. No differences were seen in titers among the different treatment groups. The dmLT-specific IgG responses were consistently high in all the experiments performed.

Figure 4A:
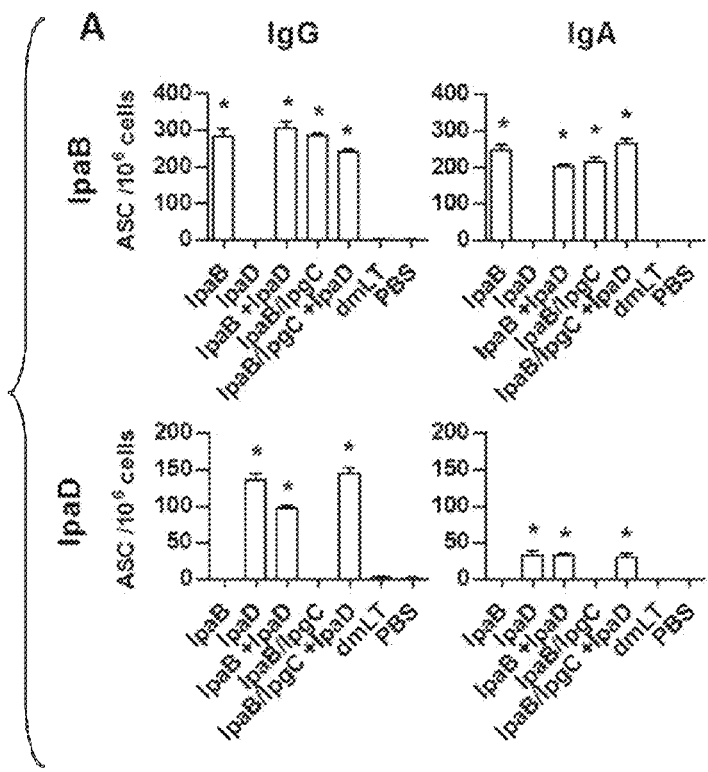

Ipa-specific IgA- and IgG-secreting cells in systemic tissues. In addition to serum antibodies, we measured the frequency of vaccine-induced ASC in spleen and bone marrow. These cells represent pools of long-lived plasma cells and memory cells, respectively, which have the capacity to maintain circulating antibody levels. IgG and IgA ASC specific for IpaB and IpaD were detected in the spleen of vaccinated mice one month after the last immunization (FIG. 4A). Mice that received IpaB or the IpaB/IpgC complex, either alone or co-administered with IpaD, developed high frequencies of IpaB-specific IgA- and IgG-secreting cells (between 200-300 SFC per $10^6$ cells). ASC responses against IpaD were also detected, albeit frequencies were lower than those against IpaB ($P<0.05$). While responses to IpaB included both IgG- and IgA-secreting cells, the ASC responses to IpaD consisted primarily of IgG-secreting cells (10-150 SFC per $10^6$ cells). Similar ASC response profiles and levels were seen in the spleen on day 39 after immunization (data not shown).

Figure 4B:
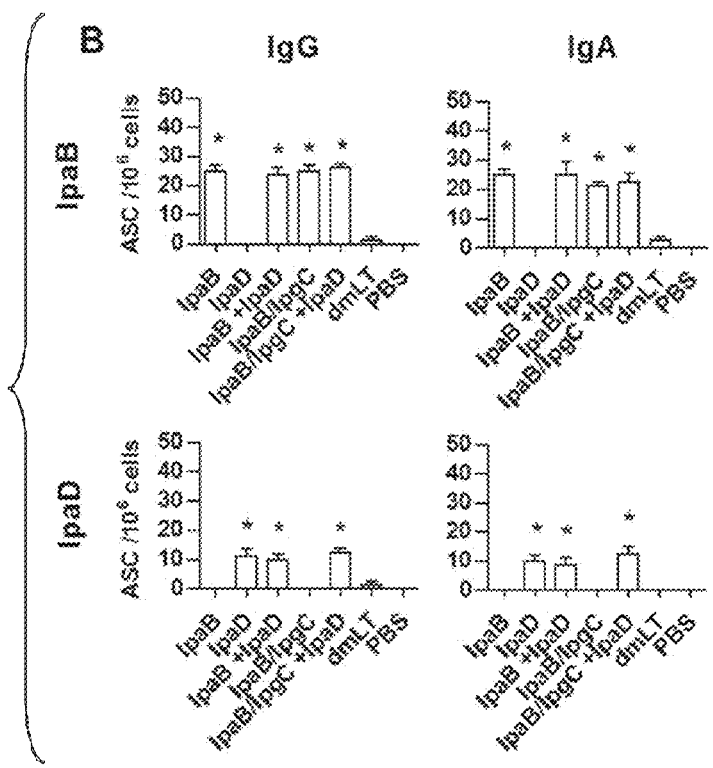

Similarly, vaccine-induced IgG- and IgA-secreting cells against IpaB were found in the bone marrow of vaccinated mice (FIG. 4B). ASC responses were also produced against IpaD, albeit at significantly lower levels ($P<0.05$). The frequencies of ASC responses against both IpaB and IpaD in the bone marrow were lower (<30 SFC per 106 cells) than the frequencies measured in the spleen (40-300 per 106 cells). In this tissue, we did not see the prevalence of IpaD-specific IgG ASC found in the spleen, possibly because all responses to IpaD were markedly low. When comparing ASC responses among the different groups and treatments, the ASC responses to IpaB and IpaD were similar regardless of whether IpaB was complexed or not with IpgC or whether IpaB and IpaD were given alone or combined. No ASC responses to IpaB and IpaD were detected in mice that received dmLT alone or in the PBS controls.

Stool IgA and nasal ASC responses following immunization with IpaB and IpaD. To demonstrate the induction of antibodies in the gastrointestinal mucosa, which represent the first line of adaptive immune defense against enteric pathogens, we measured IgA responses to IpaB and IpaD in stool supernatants from vaccinated and control mice (FIG. 5). The kinetics of IpaB-specific IgA production were similar among the different groups. Different from the serum IgG responses, which appeared relatively soon after vaccination, the fecal IgA were somewhat delayed. IgA titers to IpaB were first seen after the second immunization; IgA responses to IpaD appeared after the third, indicating that additional vaccine dose was required to raise detectable mucosal antibodies, as compared with serum. Similar to the serological responses, the intestinal IgA responses to IpaD were significantly lower compared to those against IpaB. For both antigens, IgA titers reached a plateau 2 weeks after the third immunization. No differences were seen in the IpaB stool IgA titers among the groups that received IpaB and IpaB/IpgC alone or combined with IpaD. A trend of higher IpaD IgA responses was seen in mice immunized with IpaD alone, although not reaching statistical significance. Very high levels of stool IgA were produced in response to the dmLT, which were similar in all treatment groups; responses were detected after the first immunization and had already reached maximum levels after the second dose of vaccine.

IgG and IgA ASC specific for IpaB and IpaD were detected in the nasal tissue on day 56 after immunization (FIG. 6). The frequencies of IpaB-specific ASC were again higher than those measured against IpaD ($P<0.05$). No significant differences were seen in the number of ASC against IpaB and IpaD among the different groups, regardless of whether IpaB or IpaB/IpgC were used, or whether these proteins were given alone or co-administered with IpaD.

Intranasal immunization with IpaB and IpaD elicits robust T cell-mediated immunity. In addition to antibodies, T cells are also believed to contribute to protection against *Shigella* infection through the secretion of pro-inflammatory mediators that will further activate innate immune cells and T helper cytokines that will support antibody production. T cells might also contribute to clearing the infection by promoting T cytotoxic- or NK-mediated killing of infected cells. The frequency of IFN-γ secreting T cells specific for IpaB and IpaD was measured in spleens of vaccinated and control mice, one month after the last immunization (FIG. 7). Intranasal immunization with IpaB and IpaD induced antigen-specific T cells that were able to produce IFN-γ when stimulated in vitro. The IFN-γ responses to IpaB (50-150 SFC per $10^6$ cells) were higher than those measured against IpaD (<50 SFC per 106 cells). An interesting finding, which was not paralleled in the serological analysis, was a trend of higher magnitude of IFN-γ secreting T cells in mice immunized with IpaB or IpaB/IpgC along with IpaD ($P<0.05$). This was true for the responses against both antigens, IpaB and IpaD. The frequencies of IFN-γ producing cells were consistently lower in groups that received IpaB, IpaB/IpgC or IpaD alone. No responses were detected in negative control groups that received dmLT and PBS.

Protection against *S. flexneri* and *S. sonnei* lethal pulmonary challenge. To determine the protective efficacy of IpaB and IpaD, vaccinated and control mice were subjected to a lethal pulmonary infection with homologous *S. flexneri* 2a or heterologous *S. sonnei* (FIG. 8). Two lethal dosage levels were used to perform a more stringent protection analysis: 0.6 and $1.3×10^8$ CFU of *S. flexneri*, corresponding to 11 and 24 MLD50, respectively, and 1.1 and $2×10^8$ CFU of *S. sonnei*, corresponding to 5 and 9 MLD50, respectively. Protective efficacy of the Ipa proteins when using the lower challenge dose was between 90 and 100% against *S. flexneri* (FIG. 8A) and between 60 and 80% against *S. sonnei*. The highest level of protection was seen in mice immunized with IpaB or IpaB/IpgC. When the challenge dose was doubled, the homologous and heterologous protection achieved in the vaccinated groups was somewhat lower but still significant when compared with the unvaccinated controls (FIG. 8B). Immunization with IpaB afforded 50% protection against *S. flexneri*, whereas 30% protection was attained when IpaB was co-administered with IpaD (FIG. 8B). Protection against the higher challenge dose of *S. sonnei* was 50% in mice immunized with IpaB and 45% in mice that received IpaB co-administered with IpaD. The addition of IpaD did not increase the survival rate in any of the challenges, regardless of the challenge dose. Nevertheless, a significant proportion of mice immunized with IpaD alone (70 to 90%) were protected when challenged with the lower lethal infectious doses, although this level of protection decreased drastically (20-30%) when they were exposed to a higher number of organisms of either strain. A summary of the protective efficacy values and statistical significance when comparing vaccinated vs. controls groups are shown in Table 1.

TABLE 1

Protective efficacy (% survival) against *Shigella* ssp. in a lethal pulmonary challenge model.

| Organism | Dose (CFU) | IpaB + dmLT | IpaD + dmLT | IpaB + IapD + dmLT | IpgC + dmLT | IpgC + IpaD + dmLT | dmLT | PBS |
|---|---|---|---|---|---|---|---|---|
| *S. flexneri* | $1.2 \times 10^8$ | 50* | 20 | 30* | ND | ND | 0 | 0 |
| *S. sonnei* | $2.0 \times 10^8$ | 55.5* | 30* | 50* | ND | ND | 0 | 0 |
| *S. flexneri* | $6.0 \times 10^7$ | 100* | 88* | 90* | 100* | 90* | 0 | 0 |
| *S. sonnei* | $1.1 \times 10^8$ | 80* | 70* | 80* | 80* | 60* | 0 | 0 |

ND = Not determined.
*P < 0.05 vs. group receiving dmLT (Log-Rank Test).

Discussion

Despite intense efforts, the development of an effective vaccine against *Shigella* remains a daunting task. One of the main challenges in achieving an effective prophylactic tool against this pathogen is the need to protect against multiple serotype strains. Antibodies to LPS have been associated with serotype-specific protection against Shigellosis, yet the existence of structurally and antigenically different LPS molecules limits the applicability of an LPS-containing vaccine.

Our approach to develop a safe and effective vaccine to prevent this disease involves the use of conserved proteins that could provide broad protection against multiple serotypes. Among potential cross-protective antigens, we focused our attention on the exposed proteins of the TTSA. These proteins are encoded as part of the mxi-spa operon located on the large virulence plasmid that is present in all *Shigella* ssp. Thus, in addition to being nearly identical among pathogenic *Shigella* strains, they mediate critical steps of bacterial pathogenesis. IpaB and IpaD were selected because of their significant roles during TTSS-mediated events that lead to bacterial invasion of epithelial cells. IpaD localizes to the needle tip where it controls further assembly of the TTSA, as well as TTSS effector secretion. IpaB is subsequently recruited to the tip of the needle where it interacts with host membranes to initiate formation of the translocon/pore complex. Immunological effector mechanisms (i.e. antibodies) that could interfere with their function in vivo could potentially prevent bacterial infection, making them very attractive vaccine target antigens.

We examined the immunogenicity of IpaB and IpaD (alone or combined) in a mouse intranasal immunization model, using the *E. coli* dmLT as adjuvant, and demonstrated that both proteins were able to induce robust serum and mucosal antibody levels and elevated frequencies of antibody-secreting cells in mucosal and systemic tissues. They also induced strong antigen-specific cell-mediated immunity responses, evidenced by the presence of IFN-γ secreting T cells. Most important, very high levels of protection (80 to 100%) were achieved against a homologous and a heterologous strain using a lethal pulmonary challenge model. The dmLT molecule is a derivative of the heat-labile enterotoxin of *E. coli* with two attenuating mutations in the enzymatically active A-subunit (R192G/L211A); these mutations effectively reduce enterotoxicity without impacting the adjuvant properties of the molecule. It was chosen as an adjuvant for our studies because it has been shown to enhance the production of vaccine-specific humoral and cell-mediated immune responses in both the systemic and mucosal compartments when it is included as part of a vaccine formulation.

IpaB was the most immunogenic of the two proteins, consistently and across measurements. Both serum IgG and stool IgA responses to IpaB appeared faster and achieved a higher magnitude than the responses induced by IpaD. This superior immunogenicity was also seen at the T cell response level. The co-administration of proteins had no effect on their individual serological responses, although it appeared to have an impact in the T cell responses as discussed below. The presence of high frequencies of IpaB/D specific ASC in the spleen indicates the capacity of the vaccine to induce a large pool of functional plasma cells, which are the source of systemic antibodies. The demonstration of antigen-specific ASC in the bone marrow indicates the existence of B memory cells, which can reactivate upon a subsequent antigen encounter to mount a rapid and strong anamnestic response and thus contribute to long-term protection.

The ability to generate mucosal antigen-specific ASC and to produce intestinal sIgA are also important features of our IpaB/D-based vaccine, as these immunological effectors would be necessary to prevent mucosal enteric infection in humans. Although the mechanisms of protection against *Shigella* have not been elucidated, mucosal immune defenses are sought, as they block pathogens in the intestinal lumen, preventing their attachment and infection of epithelial cells. Ipa-specific sIgA antibodies are expected to neutralize TTSS interactions at the mucosal epithelial barrier thereby preventing bacterial invasion of host cells. IgG antibodies might also contribute to protection when infection has occurred, facilitating opsonophagocytic killing by polymorphonuclear neutrophils and macrophages.

In addition to antibodies, both IpaB and IpaD induced high frequencies of IFN-γ-secreting T cells demonstrating the presence of robust cell-mediated immunity. Production of IFN-γ is required for protection of mice against *Shigella* pulmonary infection. Likewise, T cell-mediated immunity is thought to be necessary for protection of humans against Shigellosis. IFN-γ activated macrophages abrogate bacterial growth whereas, in the absence of IFN-γ, *Shigella* replicates intracellularly and further disseminates, which suggests an IFN-γ mediated mechanism for controlling infection. Production of IFN-γ in response to IpaB has been demonstrated using peripheral mononuclear cells (PBMC) from infected individuals or from subjects that received live attenuated vaccine organisms.

In our studies, the production of IFN-γ appeared to be increased when IpaB/D were administered together, as opposed to the proteins given alone, suggesting a synergistic or more effective activation of antigen-presenting cells or Th1 lymphocytes. Interestingly, the increased responses appeared to be limited to T cells, as they were not seen in the antibody or ASC measurements. This effect was not due to cross reactivity or contamination, as cells from mice immunized with IpaB did not respond against IpaD and vice versa.

Although IpaB degrades when expressed in the *E. coli* cytoplasm, it can be stably co-expressed and purified with its cognate chaperone, IpgC. The complex can then be separated by the addition of the detergent OPOE, which results in stable, multimeric IpaB. While IpaB would be the obvious antigen, separation from IpgC requires an additional purification step and the use of a non-GRAS detergent, OPOE, which is currently the only detergent found to efficiently separate the complex. This lengthens the purification process and increases production costs. Thus, the question emerged as to whether IpaB/IpgC is as equally immunogenic as IpaB and could serve as vaccine antigen. We found no significant differences between IpaB and IpaB/IpgC in any of the responses measured. This finding could facilitate the production of a vaccine with a more simple production process and reduced costs.

Mice immunized with IpaB/D were protected against *Shigella* lethal infection in a pulmonary challenge. Heterologous protection was also observed using *Shigella sonnei*. Protection in the lower dose challenge was significant for all combinations of Ipa proteins tested. In agreement with the lower immune responses, immunization with IpaD afforded lower protection compared with IpaB. Protection conferred by IpaB/IpgC was comparable to that induced by purified IpaB.

Contrary to what we expected, the combination IpaB/D did not result in increased protection in any of the challenge conditions. We believe, however, that it would still be advantageous to maintain both antigens in a future vaccine candidate since IFN-γ responses seemed to be improved, which might be important to enhance protection in humans.

Another vaccine candidate that contains *Shigella* Ipas is the "Invasin-LPS complex" or Invaplex. This vaccine consists of a mixture of IpaB, IpaC and LPS (and possibly other antigens) present in water extracts from intact *Shigella*. Two chromatographic fractions, designated Invaplex 24 and 50, were immunogenic and protective against homologous virulent strains in mice and guinea pigs. The *S. flexneri* 2a Invaplex 50 vaccine was safe and immunogenic when administered intranasally to human volunteers in Phase 1 clinical studies. However, this vaccine failed to protect subjects from a subsequent oral challenge with virulent *S. flexneri* 2a 2457T. Unlike the Invaplex, our vaccine contains known quantities of highly purified IpaB, along with IpaD, and it does not contain LPS.

Although antibodies to LPS are known to mediate protection against shigellosis, our study provides the first evidence that protective immunity can be induced by the IpaB/D vaccine combination, and in the absence of LPS. A protein-based, LPS-free vaccine would be safer and amenable for use in infants, young children and immune-compromised individuals. The demonstration of cross-protective immunity using purified TTSA proteins is also novel and has broader implications as the TTSA tip proteins from other Gram-negative enteric pathogens could prove to be protective antigens as well. Through the use of efficient antigen delivery systems, TTSA-based vaccines could potentially be administered to humans to induce mucosal immunity.

In sum, a subunit-based IpaB/D vaccine could be an effective broadly protective vaccine for prevention of shigellosis.

Example 2

Generation of an IpaD-IpaB Chimeric (Fusion) Protein

Two proteins sit at the tip of the *Shigella* TTSA needle. IpaD resides at the top of the TTSA needle; however, upon activation of IpaD, IpaB mobilizes to a position at the needle tip distal to IpaD and is responsible for host cell contact by *Shigella*. These two proteins are exposed to the immune system and are thus prime vaccine candidates.

Example 1 describes purification of IpaD and IpaB via His-tag technology using pET plasmid vectors (commercially available from Novagen). While IpaD can be purified by standard methods, IpaB requires co-expression with its chaperone IpgC in a method similar to that published by Birket, et al. (Biochemistry [2007] 46:8128-8137). In order to release IpgC from IpaB, the detergent OPOE was added. OPOE is not a GRAS reagent and therefore must be removed from the purification scheme or replaced. Therefore, in addition to IpaD and IpaB alone, the IpaB/IpgC complex was used to vaccinate mice intranasally, followed by *Shigella* challenge (FIGS. 9 and 10).The results showed that these proteins provided significant protection from the *Shigella* challenge, and the IpaB/IpgC complex was as protective as the IpaB alone.

However, the use of a protein complex in a vaccine composition may not be optimal. Thus, a third method of preparation of the proteins in the form of a chimeric protein of IpaD-IpaB was undertaken. The genes for IpaD and IpaB were genetically fused and inserted into the vector pET15b. To produce the plasmid, an NdeI/XhoI PCR fragment of IpaD without a stop codon was subcloned 5' to an XhoI/BamHI IpaB in pET15b. The plasmid was cotransformed into Tuner (DE3) with IpgC/pACYCDuet-1. This strain was used to inoculate LB media containing ampicillin and chloramphenicol. The bacteria were grown to an absorbance at 600 of about 0.6 at which time they were induced to over express the fusion/IpgC with Isopropyl-β-D-thio-galactoside (IPTG). The bacteria were grown an additional three hours to allow protein expression to occur. Alternatively, a starter culture of 100 ml was used to inoculate a 5- or 10-liter fermentor vessel containing TB media. After growing overnight (16 hours), the bacteria were induced and allowed to express protein for three hours. The bacteria were collected by centrifugation, resuspended in binding buffer (see below for recipe), and lysed by microfluidization. This suspension was clarified by centrifugation and was loaded onto a nickel charged immobilized metal affinity column (IMAC). The column (5 ml) was washed with 10 bed volumes each of binding and wash buffers and then subjected to a gradient of 0% to 40% elution buffer. Peak fractions were collected, the buffer exchanged into 1M ammonium sulfate in 50 mM sodium phosphate pH 7.0 and loaded onto a Butyl Sepharose High Performance column (5 ml) with a linear gradient from 1M ammonium sulfate in 50 mM sodium phosphate pH 7.0 to 50 mM sodium phosphate. For preparation of His-tag fusion, the IMAC-bound protein complex was incubated overnight in the presence of 1% OPOE. The chaperone was removed in the flow through and subsequent wash steps. His-tag fusion was eluted in the presence of OPOE to maintain the protein in a soluble form. His-tag fusion was then further purified using size exclusion chromatography using a HiLoad 16/60 Superdex 200 Prep Grade column. All proteins were concentrated by ultrafiltration and dialyzed into PBS pH 7.2. Protein concentrations were determined via absorbance at 280 nm using extinction coefficients based on the amino acid composition of each protein.

This method produces a chimeric IpaD-IpaB protein that is stable and soluble. An SDS-PAGE picture of the purified protein is shown in FIG. 11. Further, when the plasmid is cotransformed with a plasmid encoding ipgC (in pACYC-Duet1), a multimeric protein complex of IpaD-IpaB/IpgC is formed that is similar to the one that forms from IpaB and IpgC by themselves. Importantly, this method allows a cGMP facility to produce both proteins with a single (i.e. one) fermentor run, thereby reducing the protein purification costs. Those of skill in the art will recognize that this is a very important factor when producing vaccines for developing countries.

Example 3

Further Characterization of Chimeric IpaD-IpaB Fusion Protein

Additional testing and characterization of the IpaD-IpaB fusion protein (also referred to as "DB" or "DB fusion") has also been carried out. In one experiment, mice were divided into 4 groups, A, B, C and D, and immunized as follows: Group A: 12 μg IpaB+7 μg IpaD+2.5 μg dmLT; Group B: 20 μg DB fusion+2.5 μg dmLT; Group C: 20 μg DB fusion; and Group D: PBS (control). Intranasal immunization was performed at days 0, 14 and 28. Serum IgG levels were monitored at days 0, 14, 28, 42 and 56. At Day 56, selected mice were euthanized and ASC and IFNγ secretion were analyzed, and other mice were challenged with either *S. flexneri* or *S. sonnei*.

Figure 13B:
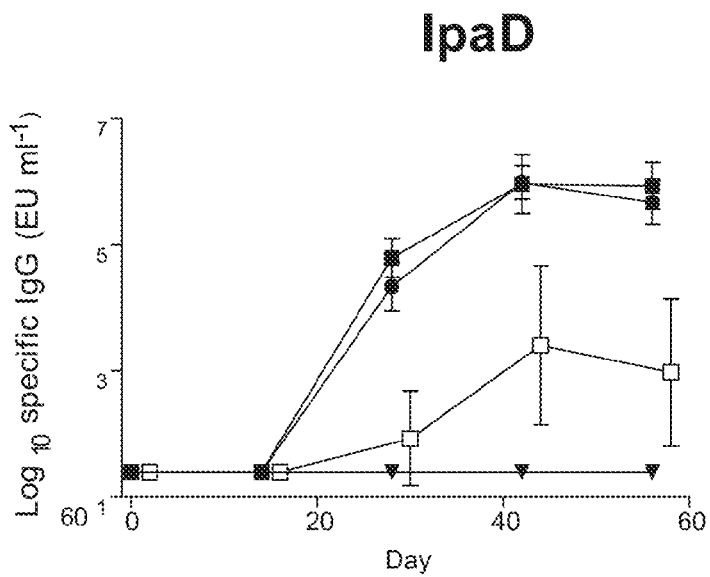
Figure 14D:
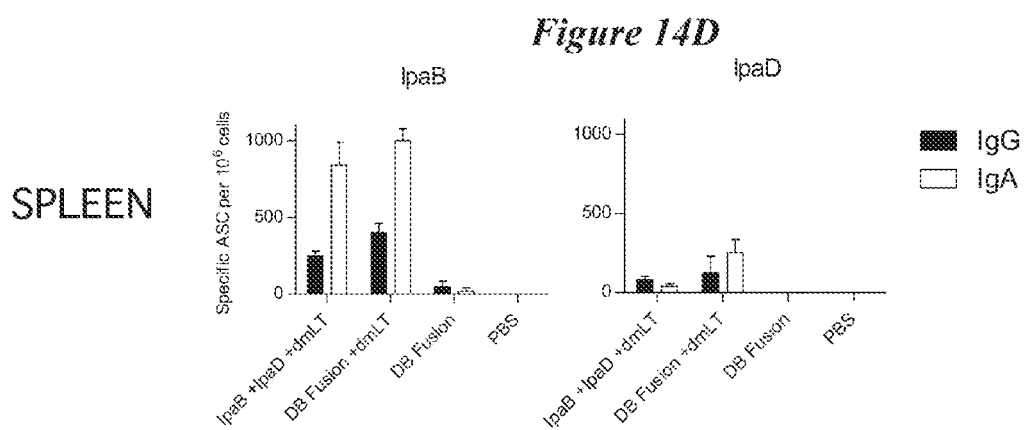
Figure 14E:
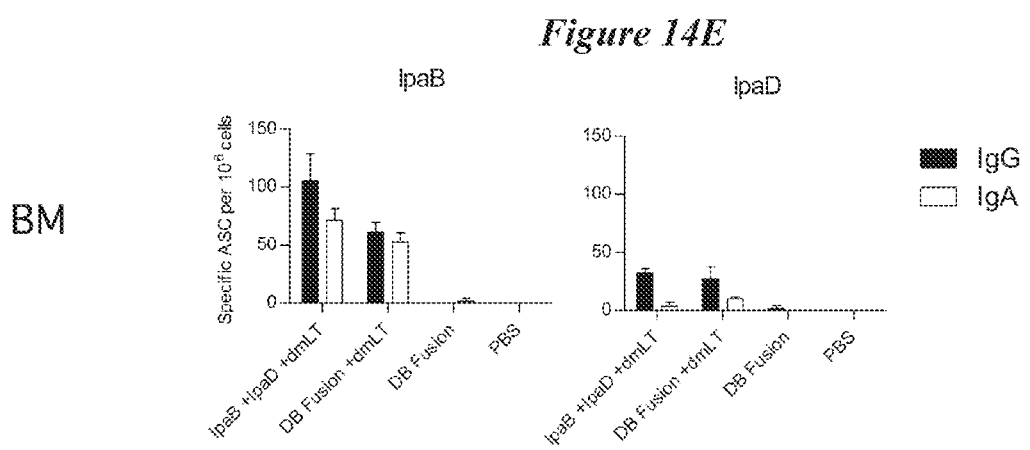

Serum IgG levels in the mice at days 0, 14, 28, 42 and 56 are presented in FIGS. 13 A and B. Serum was obtained from immunized animals and antibody titers against IpaB and IpaD were determined by ELISA. As can be seen, the antibody titers against IpaB and IpaD elicited by the DB fusion are comparable to those generated by vaccination with the separate proteins IpaB and IpaD. The peak antibody levels and the kinetics follow a very similar pattern. Even if the DB fusion protein administered without dmLT is able to generate an antibody response the presence of the adjuvant dmLT is necessary for generating a strong antibody response. This result indicates that humoral responses are generated with similar levels as the vaccine which contains the IpaB and IpaD proteins mixed together.

FIG. 14A-E show the results of ASC analysis at day 56 for lungs (14A), Peyer's patches (PP) (14B), nasal associated lymphoid tissue (NALT (14C), spleen (14D), and bone marrow (BM, 14E). At day 56, organs were extracted and single-cell suspensions were obtained. The frequency of IgG and IgA secreting cells specific for each antigen was determined by ELISpot. As can be seen, in agreement with the serum IgG titers described above, the frequency of antibody secreting cells shows no significant difference when the DB fusion is compared to the administration of the individual proteins. This result demonstrates that the observed humoral response elicited by the DB fusion occurs in similar compartments, with comparable (or in some instances higher) intensities for both antigens. Both treatments are able to induce an IgA response in several organs. Additionally, generation of memory B cells was demonstrated in the bone marrow, suggesting long lasting immunity.

FIG. 15A-C shows the results of an analysis of IFN-γ secreting cells, cytokine secretion, and IL-17 secretion, respectively. Spleen cells were extracted and stimulated with IpaB or IpaD; supernatants were collected and analyzed for cytokine secretion. In addition, the frequency of IFN-γ secreting cells was also determined.

As can be seen, the DB fusion was able to generate a higher specific cytokine response in the case of IFN-γ secreting cells and secretion levels of IL-17 and IL-2, compared to the administration of IpaB and IpaD. This demonstrates that the DB fusion protein has a unique advantage in the generation of cell-mediated immunity, which can be important for control of *Shigella* infection.

The detergent effects on the secondary structure of the IpaD/B fusion protein were assessed using circular dichroism (CD). The experiments were carried out using 0.3 mg.ml of protein in the presence of the detergents octyl polyoxyethylene (OPOE) and lauryldimethylamine-oxide (LDAO), compared to a combination of IpaD and IpaB proteins in the presence of OPOE, and IpaD/B fusion in phosphate buffered saline (PBS) after dialysis to remove LDAO detergent. The results are presented in FIG. 16. As can be seen, the spectra indicate that DB is an ordered highly α-helical protein displaying characteristic double minima at 208 and 22 nm. The data also suggest that the DB protein is stable in the detergent LDAO. This could be advantageous when isolating the protein and/or when formulating vaccines compositions; LDAO is much less expensive that OPOE and has a well-defined composition, in contrast to OPOE which is a heterogonous mixture. Further, the results showed that LDAO can be dialyzed out of a solution of DB in PBS and yet the protein remains soluble and maintains its secondary structure.

The effects of temperature on the secondary structure of DB protein in the presence and absence of OPOE and LDAO were also investigated by monitoring thermal melting using CD. The results are presented in FIG. 17. As can be seen, the DB protein in LDAO does not completely unfold at 90° C. Thus, in LDAO the DB protein is protected from heat indicated that it would be stable as a liquid form in the absence of a cold chain.

The thermal stability of DB protein was also investigated using CD. CD spectra of IpaD plus IpaB proteins (1:1 in 0.5% OPOE, DB in 0.5% OPOE, DB in 0.05% LDAO and DB in PBS were acquired at 10° C., and the solution was then heated to 90° C. at a rate of 15° C./hour. Spectra were reacquired after the temperature was returned to 10° C. The results are shown in FIG. 18A-D. Under most conditions tested, the proteins precipitated and visible aggregation was observed. However, DB in 0.05% LDAO remained soluble and appeared to regain its native secondary structural characteristics upon cooling back to 10° C. This is significant because upon heating and cooling the DB protein remains stable. Thus, in the absence of a cold chain or in that case of a disruption in the cold chain, the DB protein vaccine is not affected.

DB fusion was also characterized with respect to its ability to mimic IpaB's ability to disrupt phospholipid membranes. IpaB is well characterized and is known to form tetramers in OPOE that efficiently disrupt liposomes through pore formation. A sulforhodamine B (SRB) dye release assay was used to assess the ability of DB to do so. In the assay, membrane disruption releases fluorescent dye from lipid vesicles, giving rise to an increase in fluorescence. The results showed that IpaB in OPOE, IpaD+IpaB in OPOE and the DB fusion protein in OPOE all has similar membrane disruption efficiencies. Therefore, the DB fusion likely maintains at least some of the native structural characteristic of IpaB. (Notably, in LDAO detergent and in PBS buffer, DB and IpaB are both unable to cause membrane disruption.)

Next, the quaternary oligomeric structure of DB was investigated. Chemical crosslinking studies with and without the reducing agent dithiothreitol (DTT) and analyzed by gel electrophoresis identified the formation of extremely large DB fusion protein complexes. Both 0.5% OPOE and 0.05% LDAO supported the monomeric form of the protein to some extent (OPOE more so than LDAO), although most of the protein did not migrate into the gel even in the presence of detergent. Once dialyzed into detergent free PBS, the protein exclusively formed large complexes (much larger than 500 kDa) which were unable to migrate into the gel. Dynamic light scattering was used to determine the physical size of the DP oligomers. Consistent with crosslinking results, two predominant populations were identified: an ~5 nm diameter population (which may represent the monomer) and an ~25 nm population (which may represent the oligomer). In the presence of OPOE, the smaller species was primarily present while the presence of LDAO allowed the formation of the larger oligomer (which was also observed in detergent free PBS. These results showed that the DB protein is stable in LDAO for long term, but when diluted into PBS in preparation for immunization forms a large multimer that would be similar to the principle associated with virus-like particles (VLP). Thus, the multimer has a greater probability for success in humans.

Additional biophysical characterization if DB and subsequent analysis via an empirical phase diagram (EPD) has demonstrated that, in general, the fusion maintains its structure at pH 8 until higher temperatures are reached (not shown). At 60° C., the fusion protein in pH 6-7 buffer enters a molten globule state. The fusion in lower pH buffers does not exhibit exceptional stability at any temperature with high light scattering and noisy CD thermal melting curves (not shown). Interestingly, the fusion appears to exhibit mixed stability characteristics. At pH 8 the fusion appears to be more stable than IpaB with a transition temperature closer to 70° C. At pH 6, the fusion is less stable than either IpaB or IpaD associated with IpaB with an increase in stability which is more like IpaD. EPD provides a measure of the effects of physical conditions on protein stability. This in turn allows development of improved formulation taking into account conditions that are best suited to a stable vaccine and those conditions not conducive to vaccine stability. In the latter case, it also provides the basis for the screening of stabilizing agents from a library of GRAS reagents.

Example 4

Further Characterization of IpaD and IpaB Expression

In the studies described in Example 1, IpaD and IpaB were produced from plasmids that were maintained in *E. coli* by ampicillin resistance. Since ampicillin cannot be used in proteins produced for use in humans, the ipaB and ipaD genes were moved into pET28b and pET9a, respectively. Both plasmids are kanamycin resistant and therefore the resulting proteins can be used in humans The ipaD/pET9a-Tuner (DE3) strain was used to over-express IpaD using the typical shake flask method as well as in the 10 L fermentor. Both methods produced over 10 milligrams of IpaD per liter as was seen for the initial pET15b plasmid, showing that this strain and the resulting protein are ready for vaccine development.

The ipaB/pET28b plasmid was also used to co-transform Tuner (DE3) with ipgC/pACYC-Duet1. It should be noted that protein expression of this strain is sensitive to bacterial growth media when grown in shake flasks and can be problematic. Maximal protein expression typically occurs in Terrific Broth (TB) media with overnight expression at 18° C. Nevertheless, milligram quantities of protein were purified from the co-transformed Tuner (DE3) cells. When protein expression was performed in a 10 L fermentor, excellent expression was also observed. The IpaB/IpgC complex was further purified by passage over a hydrophobic interaction chromatography (HIC) column and IpaB alone (i.e. without IpgC) was purified by immobilized metal ion affinity chromatography (IMAC) in the presence of OPOE. Triton X-100 has also been shown to release IpgC from IpaB.

Example 5

Protective Efficacy Using Homologous and Heterologous *Shigella* Spp. in the Guinea Pig Model A small pilot study was performed to confirm the lack of toxicity of the Ipa proteins following intranasal administration with target doses in guinea pigs. Two animals each were inoculated intranasally with 1) IpaB (25 μg)+IpaD (100 μg) or 2) IpaB (25 μg)+IpaD (100 μg)+dmLT (10 μg). Animals were observed for 5 days and all animals tolerated the vaccination well with no abnormal clinical signs. The doses were thus determined to be safe for use in the immunogenicity/protection study.

Intranasal (IN) Immunization of Guinea Pigs

An experiment was conducted to assess intranasal (IN) immunization of guinea pigs using IpaB, IpaD, IpaB/IpgC and dmLT. The doses of protein given to the guinea pigs were: 25 μg of IpaB, 100 μg of IpaD, 32 μg IpaB/IpgC and 10 μg of dmLT. The volume of inoculation was 30-50 μl (see Table 2). Immunization was performed on days 0, 14 and 28. Sera, tears (for measurement of secretory IgA) and fecal samples were collected to examine immune responses. Three weeks after the last immunization (day 49) the guinea pigs were challenged intraocularly with *S. flexneri* 2a 2457T ($1\text{-}5\times10^8$ CFU).

The challenge results are shown in Table 3. As can be seen, 100% of animals immunized with the positive control strain CVD 1208S were protected against challenge. There were 75% and 100% attack rates in the negative control groups E and F immunized with PBS or dmLT respectively. Immunization with IpaB+IpaD+dmLT provided the highest level of protection (73%). Immunization with IpaB/IpgC+dmLT provided 20% protection. Immunization with IpaB+dmLT or IpaB/IpgC+IpaD+dmLT provided no protection against challenge.

TABLE 2

Outline for Intranasal Immunization Experiment

| Group | Day 1-2 Dose #1 | Day 14-16 Dose #2 | Day 28-30 Dose #3 | Day 55-59 Challenge |
|---|---|---|---|---|
| A (n = 5) | IpaB + dmLT | IpaB + dmLT | IpaB + dmLT | S. flexneri 2a |
| B (n = 5) | IpaB + IpaD + dmLT | IpaB + IpaD + dmLT | IpaB + IpaD + dmLT | S. flexneri 2a |
| C (n = 5) | IpaB/IpgC + dmLT | IpaB/IpgC + dmLT | IpaB/IpgC + dmLT | S. flexneri 2a |
| D (n = 5) | IpaB/IpgC + IpaD + dmLT | IpaB/IpgC + IpaD + dmLT | IpaB/IpgC + IpaD + dmLT | S. flexneri 2a |
| E (n = 5) | PBS | PBS | PBS | S. flexneri 2a |
| F (n = 5) | dmLT | dmLT | dmLT | S. flexneri 2a |
| G (n = 5) | CVD 1208S ($10^9$ CFU) | CVD 1208S ($10^9$ CFU) | CVD 1208S ($10^9$ CFU) | S. flexneri 2a |

TABLE 3

Protection against challenge following i.n. immunization.

| Vaccination Group | #animals reaching an eye score of "4"/ total #animals | Attack Rate | PE against PBS | PE against combined controls |
|---|---|---|---|---|
| A (n = 5) IpaB + dmLT | 5/5 | 100% | −33% | −12% |
| B (n = 5) IpaB + IpaD + dmLT | 1/5 | 20% | 73% | 78% |
| C (n = 5) IpaB/IpgC + dmLT | 3/5 | 60% | 20% | 33% |
| D (n = 5) IpaB/IpgC + IpaD + dmLT | 4/5 | 80% | −7% | 10% |
| E (n = 4) PBS | 3/4 | 75% | — | — |
| F (n = 5) dmLT | 5/5 | 100% | −33% | — |
| G (n = 4) CVD 1208S | 0/4 | 0% | 100% | 100% |

Figure 19B:
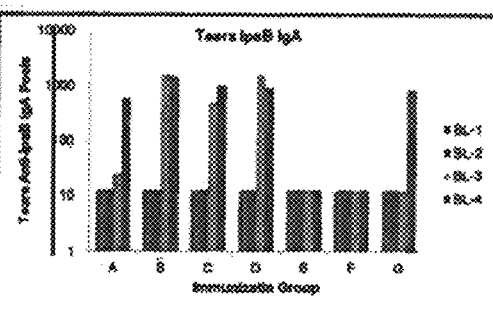

Immunology data was compiled to assess serum IgG and mucosal (tears and fecal) IgA responses to each antigen. All animals that were immunized with IpaB (Groups A, B, C, D) responded with strong serum IgG anti-IpaB responses following 3 doses (FIG. 19). Interestingly, Group B, immunized with IpaB+IpaD+dmLT responded earlier after only 2 doses. Strong mucosal IgA anti-IpaB responses were also measured in tears from the same groups (FIG. 19). Animals in Group G, immunized with CVD 1208S responded with strong anti-IpaB IgG and IgA titers. This is consistent with volunteer studies in which humans orally immunized with CVD 1208S respond with anti-IpaB antibody responses. Animals in Groups E (PBS) and F (dmLT) served as controls and did not have IpaB antibodies.

Figure 20B:
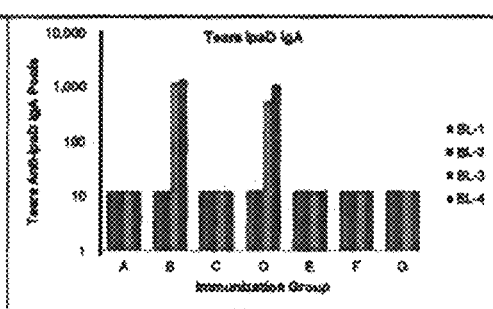

Serum and mucosal responses to IpaD were robust in Groups B and D which received the IpaD antigen (FIG. 20). No response to IpaD was measured following immunization with the vaccine strain CVD 1208S.

Serum and mucosal responses to dmLT were very strong following a single dose in all groups that received the antigen (Groups A, B, C, D, F) and were boosted to higher levels following each subsequent immunization (FIG. 21). Anti-dmLT responses were not expected in animals immunized with CVD 1208S (Group G). The responses measured in pooled tears from Group D in BL-3 and BL-4 will be assessed by titering tears from individual animals in these groups.

As expected serum and mucosal responses to S. flexneri 2a LPS were measured only in Group G, immunized with CVD 1208S (FIG. 22). Mucosal responses to LPS following intranasal inoculation with live attenuated strains are consistently strong responses.

Conclusions from intranasal immunization. Serum and mucosal responses to the IpaB and dmLT antigens were similar in Groups A, B, C, and D. Responses to IpaD were similar in Groups B and D. The only striking difference in immune responses in Group B, the highly protected group, was an earlier strong response in all animals to IpaB following 2 doses instead of following 3 doses.

Example 6

Immunogenicity of IpaB/D-dmLT Administered Intradermally

Immunogenicity and protective efficacy of IpaB and IpaD when administered orally using the mouse pulmonary model are remarkably lower compared with the responses induced when these proteins are given intranasally. Thus, an intradermal delivery approach was assessed.

In order to define the adequate amounts of IpaB, IpaD and dmLT to deliver through intradermal injection, we performed a dose finding experiment (FIG. 23) in which three dosage levels of protein were tested:
1) low dose (50 ng IpaB/IpgC+100 ng IpaD),
2) medium dose (100 ng IpaB/IpgC+250 ng IpaD) and
3) high dose (200 ng IpaB/IpgC+500 ng IpaD)

The proteins were administered in the presence of 100 ng of E. coli dmLT. The volume of inoculum was 25 µl and it was dispensed using the NanoPass MicronJet 600 microneedle device attached to a Hamilton syringe. Mice immunized with intranasally with 2.5 µg of IpaB/IpgC and 10 µg of IpaD along with 2.5 µg of dmLT were included as positive control. Negative control groups received dmLT (100 ng) and PBS via the i.d. route. A total of 3 doses were administered on days 0, 14 and 28. Serum and stool samples were collected before the first immunization and every two weeks until day 56. On day 56, mice were subjected to lethal pulmonary challenge with Shigella flexneri 2a. Five additional animals were euthanized at this time to measure systemic ASC and cell-mediated immunity.

Serum Antibody Responses

FIG. 24A-C display the kinetics of A, IpaB-, B, IpaD-, and C, dmLT-specific serum IgG and stool IgA titers from all vaccinated groups and control groups. All groups of mice vaccinated intradermally responded with high levels of IpaB and IpaD-specific serum IgG titers. The titers to IpaB increased significantly after the first and second immunization and reached similar peak/plateau levels regardless of the amount of protein given. Overall, the serum IpaB-specific IgG titers induced by intradermal immunization were only slightly lower than those induced by the intranasal immunization (positive control group). Robust responses to IpaD were also induced after intradermal vaccination. For these antibodies, however, there was a more noticeable difference in the magnitude of responses with regards to the dose. Mice immunized i.d. with the largest amounts of IpaD had elevated responses earlier (day 21), although titers in all groups reached comparable plateau levels after the 3rd immunization, at the time of challenge. The ID vaccinated animals also developed very strong serum IgG responses to the adjuvant dmLT. The dmLT-specific IgG titers were high ($\sim 1\times 10^6$ EU/ml) and consistent among all i.d. vaccinated groups, indicating that the inoculation and measurements were reproducible.

Fecal Antibody Responses

IpaB- and IpaD- specific stool IgA titers were found in the positive control group immunized with IpaB and IpaD i.n. but not in the animals immunized i.d., regardless of the amount of antigen given. Very high stool IgA responses against dmLT were observed in the positive control group, while very little (although detectable) IgA responses were found in mice immunized i.d.

Mucosal ASC

In order to assess the induction of mucosal immunity in the lungs following intradermal immunization with the Ipas, we measured the frequency of IpaB, IpaD and dmLT-specific IgG and IgA ASC in lymphocytes from the lungs on day 56 after immunization; this time corresponds to the time of challenge (FIG. 25A-C). As observed in previous experiments, the positive control group immunized with IpaB and IpaD i.n. exhibited a large number of IpaB and IpaD-specific ASCs in the lung, whereas almost no responses were seen in the groups immunized i.d. regardless of the dose administered. The ASC responses to IpaB surpassed those against IpaD, as seen in previous experiments.

Very strong ASC responses against dmLT were observed in the control group.

Systemic ASCs

The frequency of IpaB and IpaD-specific ASC was measured in the spleen and bone marrow of i.d. vaccinated mice on day 56 after immunization (FIG. 26A-C). The groups immunized intradermally had positive IpaB and IpaD IgG spleen ASC responses that were clearly dose-dependent (e.g. increased with the amount of protein administered). Both IgG and IgA ASC responses against IpaB and IpaD were also seen in the positive control; the IgA ASC responses in this group were comparable to those of mice immunized i.d. with the highest dose.

IgA ASC responses specific for dmLT were also induced following i.d. vaccination, although at lower levels. It is interesting to notice that while i.n. immunization led to the production of both IgG and IgA ASC in the spleen, intradermal vaccination led to the production of IgG ASC only, and this was true for all 3 antigens. Only the group immunized i.n. had detectable levels of IgA ASC in the spleen.

A similar pattern of responses was found in the bone marrow (FIG. 27A-C), except that in this case, similar frequencies of IgG ASC responses to IpaB and IpaD were measured in all groups, regardless of the dose of protein administered (for the i.d. groups) and the route of the immunization (animals immunized i.d. had similar levels to those immunized i.n. The IgA ASC responses to IpaB surpassed in magnitude the IgA ASC responses to IpaD. Again, i.n. immunization elicited both IgG and IgA ASC whereas i.d. immunization induced only IgG ASC.

Cell-Mediated Immunity

We measured the production of cytokines by spleens cells obtained on day 56 after immunization. To assess antigen-specific cytokine production, cells were stimulated with IpaB or IpaD for 48 hours. The supernatants were tested using a TH1/TH2 multiplex system. The levels IFN-γ, TNF-α and IL-1 produced in culture supernatants of antigen-stimulated cells are shown in FIG. 28A-F. High levels IFN-γ, TNF-α and IL-2 were produced in response to IpaB in all groups immunized i.d. and these responses were independent of the dose of antigen administered. Interestingly, the levels of TNF-α and IL-2 in response to IpaB were comparable for the i.n. and i.d. vaccinated mice. Modest production of TNF-α and IL-2 was observed in response to IpaD in the groups immunized intradermally. These responses were also independent of the immunizing dose, and much lower than the responses observed in the positive control group immunized i.n.

No differences were seen in the production of IL-12, most likely because this cytokine is non-specific and mainly produced by macrophages and antigen presenting cells, rather than antigen-specific T cells. Animals immunized i.d. produced IL-1β in response to IpaB in levels comparable to those of the positive control group immunized i.n. (FIG. 29A-D). IL-1β responses to IpaD were also detected in the i.d. immunized mice but at levels much lower than those produced by the positive control group. Mice immunized i.d. produced IL-10, IL-4 and IL-5 in response to IpaB and IpaD (FIG. 30A-F). Interestingly, intradermal immunization led to higher levels of IpaB-induced IL-4 and IL-5 compared with intranasal immunization. This was also true for IpaD-induced IL-5.

When these animals were challenged with virulent organisms using the pulmonary challenge model, up to 70% protection was observed in mice immunized with the medium dosage level, as described in detail below. Surprisingly, no protection was seen in mice receiving the highest dose of IpaB and IpaD. These observations prompted us to perform a second experiment where we included groups receiving both the medium and the high doses of antigen used in the previous experiment. To confirm the immune enhancement effect of the dmLT, the proteins were given in the presence and absence of dmLT (FIG. 31). The IpaB protein used did not contain the IpgC chaperone. A total of 25 mice were included in each group to accommodate pulmonary challenge with both S. flexneri and S. sonnei and collection of tissue for immunological assays on day 35.

The kinetics of serum IgG specific for IpaB, IpaD and dmLT from the previous experiment is shown in FIG. 32A-C. Mice that received both the high and medium doses of IpaB and IpaD in the presence of dmLT had the highest responses to IpaB and these responses were similar to those observed in the positive control group immunized i.n. with IpaB, IpaD and dmLT. In the absence of dmLT, titers against IpaB were noticeably lower. Serum IgG responses against IpaD were also produced in all groups immunized i.d. and titers of higher magnitude were also observed in the presence of dmLT.

Mucosal ASC

To assess the induction of mucosal immunity, we measured the frequency of IgG and IgA ASC in the NALT, lungs and PP (FIGS. 33A-C, 34A-C and 35A-C). Different from the previous experiment, these measurements were performed on day 35 after immunization. In contrast to our previous findings from day 56, we were able to detect IpaB-, IpaD- and dmLT-specific ASC in the lungs of i.d. vaccinated mice, on day 35. IgA ASC responses to both IpaB and IpaD were noticeable in the group receiving the medium antigen dose in the presence of dmLT. This group also developed IgG and IgA ASC responses to dmLT IgG ASCs responses to both IpaB and IpaD were detected in the NALT of i.d. immunized mice.

For the most part, these responses were lower than those of mice immunized i.n. and did not follow a defined pattern. Detectable IgA and IgG ASC responses to both IpaB were observed in the Peyer's patches of i.d. immunized mice at levels comparable with those induced in the intranasal positive control. IpaD-specific IgG and IgA responses were seen in the i.d. vaccinated mice.

Systemic ASCs

IpaB and IpaD-specific IgG and IgA ASC responses were measured in the spleen and bone marrow tissue collected on day 35 (FIG. 36A-C). As observed for the ASC measured on day 56, IgG ASC responses to IpaB and IpaD were induced by i.d. immunization and these responses were similar to those of the positive control group. A difference with the control group was that the latter also developed high levels of IpaB and IpaD-specific IgA ASC that were much lower or absent in the i.d. vaccinated mice.

Antibodies in BAL

In agreement with the presence of IgG ASC in the lung tissue, we also detected IgG antibodies specific for IpaB and IpaD in bronchoalveolar lavages from mice immunized i.d. (FIG. 37A-C). The level of antibodies did not increase with the dose. Interestingly, we did not detect production of IgA antibodies against the Ipas in these lung lavages, despite the presence of ASCs in the lung tissue of these mice. Both IgA and IgG antibodies against dmLT were present in the bronchoalveolar lavages of i.d. vaccinated mice.

Conclusions: The results demonstrate that intradermal immunization of mice with IpaB and IpaD in the presence of dmLT, using the NanoPass MicronJet 600 microneedles, induce a very strong serum IgG and systemic IgG ASC response as well as Th1 and Th2 cytokine production.

Example 7

The Determination of Protective Efficacy for the Intradermally Administered IpaB/IpaD-dmLT Against *S. Flexneri* 2a and *S. Sonnei* Using the Mouse Pulmonary Lethal Challenge Model Survival Against Lethal Pulmonary *S. Flexneri* Challenge Mice were immunized with increasing doses of IpaB and IpaD along with dmLT on days 0, 14 and 28 as described for FIG. 23. On day 56 after the initial vaccination, mice were subjected to lethal pulmonary challenge with *Shigella flexneri* 2a. The challenge dose used was: $5.8\times10^7$ CFU of *S. flexneri* 2a in a 30 μl volume. FIG. 38 shows the survival curves for all immunized animals. Full (100%) protection was achieved in the group receiving IpaB and IpaD+dmLT i.n. Animals vaccinated i.d. with the medium dose, exhibited 70% protection; while the high and low doses ID groups resulted in 0% and 30% survival, respectively.

Survival Against Lethal Pulmonary *S. Flexneri* Challenge

High and medium doses of IpaB and IpaD, along with dmLT were included; 10 mice from each group were challenged with *S. flexneri* on day 56 after the initial immunization. The challenge doses used was $5.4\times10^7$ CFU in a 30 μl volume. The group receiving the medium dose+dmLT again showed 70% survival (FIGS. 39A and B). In the absence of dmLT the protection of the medium dose group dropped to 50%. The group immunized with the highest dose of IpA antigens alone had 40% survival and the presence of the dmLT in this group did not improve survival (30% survival).

Survival Against Lethal Pulmonary *S. Sonnei* Challenge

Another subgroup of 10 mice from each immunization group was challenged with *S. sonnei*. The challenge dose used was $1.35\times10^8$ CFU of *S. sonnei* in a 30 μl volume. The highest survival, 50%, was seen in the group immunized with the medium dose of proteins in the presence of dmLT (FIGS. 39A and B). The percent survival dropped to 20% when dmLT was absent. The high dose group+dmLT had only 10% survival. The presence of dmLT along with the high dose of IpA proteins did not improve survival; it actually reduced it in both experiments for reasons unknown (40% survival in the absence of dmLT). In both challenges, 100% protection was seen in the positive control group.

Example 8

Protective Efficacy Using Homologous and Heterologous *Shigella* Spp. in the Guinea Pig Model Microneedle and adapter devices were tested for use in the guinea pig. The adapter method was chosen since this device was readily available and i.d. injection was efficient using the adapter. The intradermal experiment was completed in which guinea pigs (Hartley strain), 10 per group, were immunized i.d. with the IpaB/D vaccine candidates and dmLT as described in Table 4. The doses chosen were based on results from mouse studies wherein optimal efficacy was achieved using the middle dose tested. The middle mouse doses were adjusted for body weight of guinea pigs. For intradermal inoculation 1.0 μg IpaB, 2.5 μg IpaD and 1.0 μg dmLT were used. For the repeated intranasal immunization (Group D) inoculation with 25 μg IpaB, 100 μg IpaD and 10 μg dmLT were used.

TABLE 4

Outline for Intradermal Immunization Experiment.

| Group | Day 1<br>Dose #1 | Day 28<br>Dose #2 | Day 56<br>Dose #3 | Day 84<br>Challenge |
|---|---|---|---|---|
| A (n = 10)<br>A1-A10 | IpaB + IpaD (ID) | IpaB + IpaD (ID) | IpaB + IpaD (ID) | *S. flex* 2a |
| B (n = 10)<br>B11-B20 | IpaB + IpaD + dmLT (ID) | IpaB + IpaD + dmLT (ID) | IpaB + IpaD + dmLT (ID) | *S. flex* 2a |
| C(n = 10)<br>C21-C30 | PBS | PBS | PBS | *S. flex* 2a |
| D (n = 10)<br>D31-D40 | IpaB + IpaD + dmLT (IN) | IpaB + IpaD + dmLT (IN) | IpaB + IpaD + dmLT (IN) | *S. flex* 2a |
| E(n = 5)<br>E41-E45 | CVD 1208S ($10^9$ CFU) | CVD 1208S ($10^9$ CFU) | CVD 1208S ($10^9$ CFU) | *S. flex* 2a |

Sera, tears (for measurement of secretory IgA) and fecal samples were collected prior to the first dose and 2 weeks following each dose to examine immune responses to each antigen included. Four weeks after the last immunization the guinea pigs were challenged intraocularly with *S. flexneri* 2a 2457T (1-5×10$^7$CFU).

Challenge results are shown in Table 5. 100% of animals immunized with the positive control strain CVD 1208S were protected against challenge. There was 100% attack rate in the negative control Group C immunized with PBS. Intradermal immunization with IpaB+IpaD+/−dmLT did not provide protection against challenge. Intranasal immunization with IpaB+IpaD+dmLT conferred 33% protection against challenge. However, the progression of disease in this group was slower than that in Groups A, B or C (FIG. 40).

TABLE 5

Protection Against Challenge Following Intradermal Immunization.

| Vaccination Group | #animals reaching an eye score of "4" at any time point post challenge/total #animals | Attack Rate | PE against PBS |
|---|---|---|---|
| A (n = 10) IpaB + IpaD (i.d.) | 10/10 | 100% | 0% |
| B (n = 10) IpaB + IpaD + dmLT (i.d.) | 10/10 | 100% | 0% |
| C (n = 9) PBS (i.d.) | 9/9 | 100% | 0% |
| D (n = 9) IpaB + IpaD + dmLT (i.n.) | 6/9 | 67% | 33% |
| E (n = 5) CVD 1208S (i.n.) | 0/5 | 0% | 100% |

Immunology data was compiled to assess serum IgG and mucosal (tears and fecal) IgA responses to each antigen. All animals that were immunized with IpaB (Groups A, B and D) responded with strong serum IgG anti-IpaB responses following 2 doses (FIGS. 41A and B). Neither the route of immunization, i.d. or i.n. nor the presence of dmLT affected the magnitude of serum anti-IpaB responses. Mucosal anti-IpaB IgA antibodies in tears were very high following i.n. immunization and moderate following i.d. immunization, but only in the presence of dmLT (Group B). Animals in Group E, immunized with CVD 1208S responded with strong anti-IpaB IgG and IgA titers. Serum IgG responses to IpaD were elicited in Groups A, B, and D at approximately equivalent levels. Anti-IpaD titers were 5 to 10-fold lower than titers to IpaB (FIGS. 42A and B).

Mucosal anti-IpaD IgA was only measured in Group D, immunized by the i.n. route. Immunization with CVD 1208S did not elicit serum or mucosal anti-IpaD responses. Serum anti-dmLT IgG responses were elicited in Groups B, and D (FIGS. 43A and B). Responses following i.n. immunization were significantly higher than those following i.d. immunization. Mucosal anti-dmLT IgA was only elicited in Group D following i.n. immunization. As expected serum and mucosal responses to *S. flexneri* 2a LPS were measured only in Group E, immunized with CVD 1208S (FIGS. 44A and B). Mucosal responses to LPS following intranasal inoculation with live attenuated strains are consistently strong responses Conclusions from Intradermal Immunization. Intradermal immunization was able to elicit serum anti-IpaB and anti-IpaD responses equivalent to those elicited by intranasal immunization. However, i.d. immunization did not stimulate mucosal IgA responses to IpaB, IpaD or dmLT.

Summary of Guinea Pig Studies. The guinea pig serves as an alternative model for assessing the immunogenicity and protective capacity of *Shigella* vaccines. The most protective regimen in these studies was i.n. immunization with IpaB+IpaD+dmLT. The combined efficacy of this regimen from the 2 experiments was 46%.

Example 9

Immunogenicity of *Shigella* IpaB/IpaD with dmLT Administered Intradermally to Piglets Due to the similarity of their immune response and skin thickness with humans, piglets were also chosen as an animal model. Piglets were immunized three times, two weeks apart either intradermally, sublingually or a combination of the two (Table 6).

TABLE 6

Immunogenicity of *Shigella* IpaB/IpaD with dmLT administered intradermally to piglets.

| Group | Pigs | | Description |
|---|---|---|---|
| 84-A-SL + ID | 1 | 338 | Sublingual, PBS; Intradermal, PBS |
| 84-B-ID | 2 | 328, 329 | Intradermal, IpaB 250 ug + IpaD 250 ug (High Dose) |
| 84-C-ID | 2 | 330, 331 | Intradermal, IpaB 25 ug + IpaD 25 ug + dmLT 10 ug (Low Dose) |
| 84-D-ID | 2 | 332, 333 | Intradermal, IpaB 250 ug + IpaD 250 ug + dmLT 10 ug (High Dose) |
| 84-E-SL | 2 | 334, 335 | Sublingual, IpaB 2.5 mg + IpaD 2.5 mg + dmLT 30 ug |
| 84-F-SL + ID | 2 | 336, 337 | Sublingual, IpaB 2.5 mg + IpaD 2.5 mg + dmLT 30 ug; Intradermal, IpaB 250 ug + IpaD 250 ug + dmLT 30 ug (High Dose) |
| Total | 11 | | |

Immune responses were measured at the time of immunization and two weeks after the last immunization. Although a serum IgG response was elicited by IpaB+IpaD alone, the highest response was seen after admixing dmLT (FIG. 45). Interestingly, the dose of IpaB did not impact serum IgG. In contrast, a 10-fold increase in IpaD lead to an increase is anti-IpaD IgG. Sublingual administration did not induce a serum IgG response against either IpaB or IpaD, but the response could be boosted to the sublingual level after sublingual immunization. IgA titers were assessed in serum, vaginal washes and saliva (FIG. 46).

Example 10

Protection Studies of the Fusion Protein in Mice

Figure 47B:
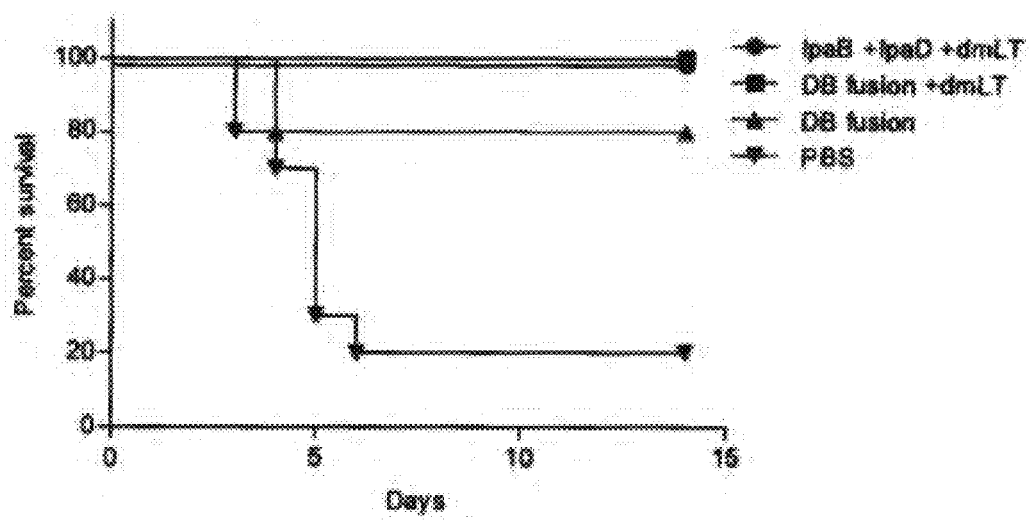

The protective efficacy of the fusion protein was tested using DB fusion or DB fusion plus dmLT, in comparison to vehicle (PBS) and IPAB+IpaD+dmLT. The results are shown in FIG. 47. As can be seen, mice which received the DB fusion together with dmLT had a greater than 70% survival rate when challenged with *S flexneri* and near 100% survival rate when challenged with *S. sonnei*. These results demonstrate cross-species protection against challenge by vaccination with the DB fusion protein.

While the invention has been described in terms of its preferred embodiments, those skilled in the art will recognize that the invention can be practiced with modification within the spirit and scope of the appended claims. Accord-

What is claimed is:

1. A cross-protective, O-serotype independent vaccine against *Shigella* in a form suitable for administration to an animal, comprising at least one fusion protein comprising IpaB and IpaD, wherein said vaccine is free of *Shigella* lipopolysaccharide (LPS).

2. The cross-protective, O-serotype independent vaccine of claim 1, wherein said vaccine comprises a complex of i) said fusion protein comprising IpaB and IpaD; and ii) IpgC.

3. The vaccine of claim 1, wherein said fusion protein is or includes SEQ ID NO:4.

4. A fusion protein that is or includes SEQ ID NO:4.

5. A cross-protective, O-serotype independent vaccine against *Shigella* that is comprised of a fusion protein of IpaB and IpaD, wherein said vaccine is free of *Shigella* lipopolysaccharide (LPS).

6. The vaccine of claim 5, wherein said fusion protein is or includes SEQ ID NO:4.

* * * * *

SEQUENCE LISTING

<160> NUMBER OF SEQ ID NOS: 4

<210> SEQ ID NO 1
<211> LENGTH: 580
<212> TYPE: PRT
<213> ORGANISM: Shigella flexneri

<400> SEQUENCE: 1

```
Met His Asn Val Ser Thr Thr Thr Gly Phe Pro Leu Ala Lys Ile
1               5                   10                  15

Leu Thr Ser Thr Glu Leu Gly Asp Asn Thr Ile Gln Ala Ala Asn Asp
                20                  25                  30

Ala Ala Asn Lys Leu Phe Ser Leu Thr Ile Ala Asp Leu Thr Ala Asn
                35                  40                  45

Gln Asn Ile Asn Thr Thr Asn Ala His Ser Thr Ser Asn Ile Leu Ile
    50                  55                  60

Pro Glu Leu Lys Ala Pro Lys Ser Leu Asn Ala Ser Ser Gln Leu Thr
65                  70                  75                  80

Leu Leu Ile Gly Asn Leu Ile Gln Ile Leu Gly Glu Lys Ser Leu Thr
                85                  90                  95

Ala Leu Thr Asn Lys Ile Thr Ala Trp Lys Ser Gln Gln Gln Ala Arg
                100                 105                 110

Gln Gln Lys Asn Leu Glu Phe Ser Asp Lys Ile Asn Thr Leu Leu Ser
            115                 120                 125

Glu Thr Glu Gly Leu Thr Arg Asp Tyr Glu Lys Gln Ile Asn Lys Leu
    130                 135                 140

Lys Asn Ala Asp Ser Lys Ile Lys Asp Leu Glu Asn Lys Ile Asn Gln
145                 150                 155                 160

Ile Gln Thr Arg Leu Ser Asn Leu Asp Pro Glu Ser Pro Glu Lys Lys
                165                 170                 175

Lys Leu Ser Arg Glu Glu Ile Gln Leu Thr Ile Lys Lys Asp Ala Ala
            180                 185                 190

Val Lys Asp Arg Thr Leu Ile Glu Gln Lys Thr Leu Ser Ile His Ser
            195                 200                 205

Lys Leu Thr Asp Lys Ser Met Gln Leu Glu Lys Glu Ile Asp Ser Phe
    210                 215                 220

Ser Ala Phe Ser Asn Thr Ala Ser Ala Glu Gln Leu Ser Thr Gln Gln
225                 230                 235                 240

Lys Ser Leu Thr Gly Leu Ala Ser Val Thr Gln Leu Met Ala Thr Phe
                245                 250                 255

Ile Gln Leu Val Gly Lys Asn Asn Glu Glu Ser Leu Lys Asn Asp Leu
            260                 265                 270

Ala Leu Phe Gln Ser Leu Gln Glu Ser Arg Lys Thr Glu Met Glu Arg
        275                 280                 285

Lys Ser Asp Glu Tyr Ala Ala Glu Val Arg Lys Ala Glu Glu Leu Asn
    290                 295                 300

Arg Val Met Gly Cys Val Gly Lys Ile Leu Gly Ala Leu Leu Thr Ile
305                 310                 315                 320

Val Ser Val Val Ala Ala Ala Phe Ser Gly Gly Ala Ser Leu Ala Leu
```

```
                    325                 330                 335
Ala Ala Val Gly Leu Ala Leu Met Val Thr Asp Ala Ile Val Gln Ala
                340                 345                 350

Ala Thr Gly Asn Ser Phe Met Glu Gln Ala Leu Asn Pro Ile Met Lys
            355                 360                 365

Ala Val Ile Glu Pro Leu Ile Lys Leu Leu Ser Asp Ala Phe Thr Lys
        370                 375                 380

Met Leu Glu Gly Leu Gly Val Asp Ser Lys Lys Ala Lys Met Ile Gly
385                 390                 395                 400

Ser Ile Leu Gly Ala Ile Ala Gly Ala Leu Val Leu Ala Ala Val
                405                 410                 415

Val Leu Val Ala Thr Val Gly Lys Gln Ala Ala Lys Leu Ala Glu
                420                 425                 430

Asn Ile Gly Lys Ile Ile Gly Lys Thr Leu Thr Asp Leu Ile Pro Lys
                435                 440                 445

Phe Leu Lys Asn Phe Ser Ser Gln Leu Asp Asp Leu Ile Thr Asn Ala
            450                 455                 460

Val Ala Arg Leu Asn Lys Phe Leu Gly Ala Ala Gly Asp Glu Val Ile
465                 470                 475                 480

Ser Lys Gln Ile Ile Ser Thr His Leu Asn Gln Ala Val Leu Leu Gly
                485                 490                 495

Glu Ser Val Asn Ser Ala Thr Gln Ala Gly Gly Ser Val Ala Ser Ala
            500                 505                 510

Val Phe Gln Asn Ser Ala Ser Thr Asn Leu Ala Asp Leu Thr Leu Ser
            515                 520                 525

Lys Tyr Gln Val Glu Gln Leu Ser Lys Tyr Ile Ser Glu Ala Ile Glu
            530                 535                 540

Lys Phe Gly Gln Leu Gln Glu Val Ile Ala Asp Leu Leu Ala Ser Met
545                 550                 555                 560

Ser Asn Ser Gln Ala Asn Arg Thr Asp Val Ala Lys Ala Ile Leu Gln
                565                 570                 575

Gln Thr Thr Ala
            580

<210> SEQ ID NO 2
<211> LENGTH: 332
<212> TYPE: PRT
<213> ORGANISM: Shigella flexneri

<400> SEQUENCE: 2

Met Asn Ile Thr Thr Leu Thr Asn Ser Ile Ser Thr Ser Ser Phe Ser
1               5                   10                  15

Pro Asn Asn Thr Asn Gly Ser Ser Thr Glu Thr Val Asn Ser Asp Ile
            20                  25                  30

Lys Thr Thr Thr Ser Ser His Pro Val Ser Ser Leu Thr Met Leu Asn
        35                  40                  45

Asp Thr Leu His Asn Ile Arg Thr Thr Asn Gln Ala Leu Lys Lys Glu
    50                  55                  60

Leu Ser Gln Lys Thr Leu Thr Lys Thr Ser Leu Glu Glu Ile Ala Leu
65                  70                  75                  80

His Ser Ser Gln Ile Ser Met Asp Val Asn Lys Ser Ala Gln Leu Leu
                85                  90                  95

Asp Ile Leu Ser Arg Asn Glu Tyr Pro Ile Asn Lys Asp Ala Arg Glu
            100                 105                 110
```

Leu Leu His Ser Ala Pro Lys Glu Ala Glu Leu Asp Gly Asp Gln Met
            115                 120                 125

Ile Ser His Arg Glu Leu Trp Ala Lys Ile Ala Asn Ser Ile Asn Asp
    130                 135                 140

Ile Asn Glu Gln Tyr Leu Lys Val Tyr Glu His Ala Val Ser Ser Tyr
145                 150                 155                 160

Thr Gln Met Tyr Gln Asp Phe Ser Ala Val Leu Ser Ser Leu Ala Gly
                165                 170                 175

Trp Ile Ser Pro Gly Gly Asn Asp Gly Asn Ser Val Lys Leu Gln Val
            180                 185                 190

Asn Ser Leu Lys Lys Ala Leu Glu Glu Leu Lys Glu Lys Tyr Lys Asp
        195                 200                 205

Lys Pro Leu Tyr Pro Ala Asn Asn Thr Val Ser Gln Glu Gln Ala Asn
210                 215                 220

Lys Trp Leu Thr Glu Leu Gly Gly Thr Ile Gly Lys Val Ser Gln Lys
225                 230                 235                 240

Asn Gly Gly Tyr Val Val Ser Ile Asn Met Thr Pro Ile Asp Asn Met
                245                 250                 255

Leu Lys Ser Leu Asp Asn Leu Gly Gly Asn Gly Glu Val Val Leu Asp
            260                 265                 270

Asn Ala Lys Tyr Gln Ala Trp Asn Ala Gly Phe Ser Ala Glu Asp Glu
        275                 280                 285

Thr Met Lys Asn Asn Leu Gln Thr Leu Val Gln Lys Tyr Ser Asn Ala
    290                 295                 300

Asn Ser Ile Phe Asp Asn Leu Val Lys Val Leu Ser Ser Thr Ile Ser
305                 310                 315                 320

Ser Cys Thr Asp Thr Asp Lys Leu Phe Leu His Phe
                325                 330

<210> SEQ ID NO 3
<211> LENGTH: 155
<212> TYPE: PRT
<213> ORGANISM: Shigella flexneri

<400> SEQUENCE: 3

Met Ser Leu Asn Ile Thr Glu Asn Glu Ser Ile Ser Thr Ala Val Ile
1               5                   10                  15

Asp Ala Ile Asn Ser Gly Ala Thr Leu Lys Asp Ile Asn Ala Ile Pro
            20                  25                  30

Asp Asp Met Met Asp Asp Ile Tyr Ser Tyr Ala Tyr Asp Phe Tyr Asn
        35                  40                  45

Lys Gly Arg Ile Glu Glu Ala Glu Val Phe Phe Arg Phe Leu Cys Ile
50                  55                  60

Tyr Asp Phe Tyr Asn Val Asp Tyr Ile Met Gly Leu Ala Ala Ile Tyr
65                  70                  75                  80

Gln Ile Lys Glu Gln Phe Gln Gln Ala Ala Asp Leu Tyr Ala Val Ala
                85                  90                  95

Phe Ala Leu Gly Lys Asn Asp Tyr Thr Pro Val Phe His Thr Gly Gln
            100                 105                 110

Cys Gln Leu Arg Leu Lys Ala Pro Leu Lys Ala Lys Glu Cys Phe Glu
        115                 120                 125

Leu Val Ile Gln His Ser Asn Asp Glu Lys Leu Lys Ile Lys Ala Gln
    130                 135                 140

Ser Tyr Leu Asp Ala Ile Gln Asp Ile Lys Glu
145                 150                 155

<210> SEQ ID NO 4
<211> LENGTH: 914
<212> TYPE: PRT
<213> ORGANISM: Artificial Sequence
<220> FEATURE:
<223> OTHER INFORMATION: Synthetic chimeric protein

<400> SEQUENCE: 4

```
Met Asn Ile Thr Thr Leu Thr Asn Ser Ile Ser Thr Ser Ser Phe Ser
1               5                   10                  15

Pro Asn Asn Thr Asn Gly Ser Ser Thr Glu Thr Val Asn Ser Asp Ile
            20                  25                  30

Lys Thr Thr Thr Ser Ser His Pro Val Ser Ser Leu Thr Met Leu Asn
        35                  40                  45

Asp Thr Leu His Asn Ile Arg Thr Thr Asn Gln Ala Leu Lys Lys Glu
    50                  55                  60

Leu Ser Gln Lys Thr Leu Thr Lys Thr Ser Leu Glu Glu Ile Ala Leu
65                  70                  75                  80

His Ser Ser Gln Ile Ser Met Asp Val Asn Lys Ser Ala Gln Leu Leu
                85                  90                  95

Asp Ile Leu Ser Arg Asn Glu Tyr Pro Ile Asn Lys Asp Ala Arg Glu
            100                 105                 110

Leu Leu His Ser Ala Pro Lys Glu Ala Glu Leu Asp Gly Asp Gln Met
        115                 120                 125

Ile Ser His Arg Glu Leu Trp Ala Lys Ile Ala Asn Ser Ile Asn Asp
    130                 135                 140

Ile Asn Glu Gln Tyr Leu Lys Val Tyr Glu His Ala Val Ser Ser Tyr
145                 150                 155                 160

Thr Gln Met Tyr Gln Asp Phe Ser Ala Val Leu Ser Ser Leu Ala Gly
                165                 170                 175

Trp Ile Ser Pro Gly Gly Asn Asp Gly Asn Ser Val Lys Leu Gln Val
            180                 185                 190

Asn Ser Leu Lys Lys Ala Leu Glu Glu Leu Lys Glu Lys Tyr Lys Asp
        195                 200                 205

Lys Pro Leu Tyr Pro Ala Asn Asn Thr Val Ser Gln Glu Gln Ala Asn
    210                 215                 220

Lys Trp Leu Thr Glu Leu Gly Gly Thr Ile Gly Lys Val Ser Gln Lys
225                 230                 235                 240

Asn Gly Gly Tyr Val Val Ser Ile Asn Met Thr Pro Ile Asp Asn Met
                245                 250                 255

Leu Lys Ser Leu Asp Asn Leu Gly Gly Asn Gly Glu Val Val Leu Asp
            260                 265                 270

Asn Ala Lys Tyr Gln Ala Trp Asn Ala Gly Phe Ser Ala Glu Asp Glu
        275                 280                 285

Thr Met Lys Asn Asn Leu Gln Thr Leu Val Gln Lys Tyr Ser Asn Ala
    290                 295                 300

Asn Ser Ile Phe Asp Asn Leu Val Lys Val Leu Ser Ser Thr Ile Ser
305                 310                 315                 320

Ser Cys Thr Asp Thr Asp Lys Leu Phe Leu His Phe Leu Glu Met His
                325                 330                 335

Asn Val Ser Thr Thr Thr Thr Gly Phe Pro Leu Ala Lys Ile Leu Thr
            340                 345                 350

Ser Thr Glu Leu Gly Asp Asn Thr Ile Gln Ala Ala Asn Asp Ala Ala
        355                 360                 365
```

```
Asn Lys Leu Phe Ser Leu Thr Ile Ala Asp Leu Thr Ala Asn Gln Asn
    370                 375                 380

Ile Asn Thr Thr Asn Ala His Ser Thr Ser Asn Ile Leu Ile Pro Glu
385                 390                 395                 400

Leu Lys Ala Pro Lys Ser Leu Asn Ala Ser Ser Gln Leu Thr Leu Leu
                405                 410                 415

Ile Gly Asn Leu Ile Gln Ile Leu Gly Glu Lys Ser Leu Thr Ala Leu
            420                 425                 430

Thr Asn Lys Ile Thr Ala Trp Lys Ser Gln Gln Ala Arg Gln Gln
        435                 440                 445

Lys Asn Leu Glu Phe Ser Asp Lys Ile Asn Thr Leu Leu Ser Glu Thr
    450                 455                 460

Glu Gly Leu Thr Arg Asp Tyr Glu Lys Gln Ile Asn Lys Leu Lys Asn
465                 470                 475                 480

Ala Asp Ser Lys Ile Lys Asp Leu Glu Asn Lys Ile Asn Gln Ile Gln
                485                 490                 495

Thr Arg Leu Ser Asn Leu Asp Pro Glu Ser Pro Glu Lys Lys Lys Leu
            500                 505                 510

Ser Arg Glu Glu Ile Gln Leu Thr Ile Lys Lys Asp Ala Ala Val Lys
    515                 520                 525

Asp Arg Thr Leu Ile Glu Gln Lys Thr Leu Ser Ile His Ser Lys Leu
    530                 535                 540

Thr Asp Lys Ser Met Gln Leu Glu Lys Glu Ile Asp Ser Phe Ser Ala
545                 550                 555                 560

Phe Ser Asn Thr Ala Ser Ala Glu Gln Leu Ser Thr Gln Gln Lys Ser
                565                 570                 575

Leu Thr Gly Leu Ala Ser Val Thr Gln Leu Met Ala Thr Phe Ile Gln
            580                 585                 590

Leu Val Gly Lys Asn Asn Glu Glu Ser Leu Lys Asn Asp Leu Ala Leu
        595                 600                 605

Phe Gln Ser Leu Gln Glu Ser Arg Lys Thr Glu Met Glu Arg Lys Ser
    610                 615                 620

Asp Glu Tyr Ala Ala Glu Val Arg Lys Ala Glu Glu Leu Asn Arg Val
625                 630                 635                 640

Met Gly Cys Val Gly Lys Ile Leu Gly Ala Leu Leu Thr Ile Val Ser
                645                 650                 655

Val Val Ala Ala Ala Phe Ser Gly Gly Ala Ser Leu Ala Leu Ala Ala
            660                 665                 670

Val Gly Leu Ala Leu Met Val Thr Asp Ala Ile Val Gln Ala Ala Thr
        675                 680                 685

Gly Asn Ser Phe Met Glu Gln Ala Leu Asn Pro Ile Met Lys Ala Val
    690                 695                 700

Ile Glu Pro Leu Ile Lys Leu Leu Ser Asp Ala Phe Thr Lys Met Leu
705                 710                 715                 720

Glu Gly Leu Gly Val Asp Ser Lys Lys Ala Lys Met Ile Gly Ser Ile
                725                 730                 735

Leu Gly Ala Ile Ala Gly Ala Leu Val Leu Val Ala Ala Val Val Leu
            740                 745                 750

Val Ala Thr Val Gly Lys Gln Ala Ala Ala Lys Leu Ala Glu Asn Ile
        755                 760                 765

Gly Lys Ile Ile Gly Lys Thr Leu Thr Asp Leu Ile Pro Lys Phe Leu
    770                 775                 780
```

-continued

```
Lys Asn Phe Ser Ser Gln Leu Asp Asp Leu Ile Thr Asn Ala Val Ala
785                 790                 795                 800

Arg Leu Asn Lys Phe Leu Gly Ala Ala Gly Asp Glu Val Ile Ser Lys
                805                 810                 815

Gln Ile Ile Ser Thr His Leu Asn Gln Ala Val Leu Leu Gly Glu Ser
            820                 825                 830

Val Asn Ser Ala Thr Gln Ala Gly Gly Ser Val Ala Ser Ala Val Phe
        835                 840                 845

Gln Asn Ser Ala Ser Thr Asn Leu Ala Asp Leu Thr Leu Ser Lys Tyr
    850                 855                 860

Gln Val Glu Gln Leu Ser Lys Tyr Ile Ser Glu Ala Ile Glu Lys Phe
865                 870                 875                 880

Gly Gln Leu Gln Glu Val Ile Ala Asp Leu Leu Ala Ser Met Ser Asn
                885                 890                 895

Ser Gln Ala Asn Arg Thr Asp Val Ala Lys Ala Ile Leu Gln Gln Thr
            900                 905                 910

Thr Ala
```